US009605038B2

(12) United States Patent
Kang et al.

(10) Patent No.: US 9,605,038 B2
(45) Date of Patent: Mar. 28, 2017

(54) FUSION PEPTIDE COMPRISING DHFAS-1 DOMAIN AND MMP SUBSTRATE AND USE THEREOF FOR PREVENTING AND TREATING RHEUMATOID ARTHRITIS

(71) Applicant: Kyungpook National University Industry-Academic Cooperation Foundation, Daegu (KR)

(72) Inventors: Young Mo Kang, Daegu (KR); In San Kim, Daegu (KR); Jin Hee Kang, Daegu (KR); Keum Hee Sa, Daegu (KR)

(73) Assignee: Kyungpook National University Industry—Academic Cooperation Foundation, Daegu (KR)

(*) Notice: Subject to any disclaimer, the term of this patent is extended or adjusted under 35 U.S.C. 154(b) by 148 days.

(21) Appl. No.: 13/907,327

(22) Filed: May 31, 2013

(65) Prior Publication Data

US 2014/0147453 A1 May 29, 2014

Related U.S. Application Data

(63) Continuation of application No. PCT/KR2011/009318, filed on Dec. 2, 2011.

(30) Foreign Application Priority Data

Dec. 2, 2010 (KR) ........................ 10-2010-0121894

(51) Int. Cl.

| | |
|---|---|
| ***A61K 38/00*** | (2006.01) |
| ***C07K 14/435*** | (2006.01) |
| ***C07K 14/475*** | (2006.01) |

(52) U.S. Cl.

CPC .......... *C07K 14/435* (2013.01); *C07K 14/475* (2013.01); *A61K 38/00* (2013.01); *C07K 2319/50* (2013.01); *C07K 2319/74* (2013.01)

(58) Field of Classification Search

None

See application file for complete search history.

(56) References Cited

U.S. PATENT DOCUMENTS

| | | | |
|---|---|---|---|
| 7,919,464 | B2 | 4/2011 | Nam et al. |
| 2004/0087533 | A1 | 5/2004 | Dieckmann et al. |
| 2009/0035314 | A1 | 2/2009 | Kim et al. |

FOREIGN PATENT DOCUMENTS

| | | | |
|---|---|---|---|
| KR | 10-0804166 B1 | 2/2008 | |
| KR | WO 2009064051 A1 * | 5/2009 | ......... A61K 38/1709 |

OTHER PUBLICATIONS

Visse et al. Matrix Metalloproteinases and Tissue Inhibitors of Metalloproteinases Structure, Function, and Biochemistry. Circulation Research. 2003; 92: 827-839.*

Park et al. Peptide Substrate Specificities and Protein Cleavage Sites of Human Endometase/Matrilysin-2/Matrix Metalloproteinase-26*. Journal of Biological Chemistry. 277(38): 35168-35175.*

Bowie et al. Deciphering the Message in Protein Sequences: Tolerance to Amino Acid Substitutions. Science, 1990, 247:1306-1310.*

Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990.*

Lazar et al. Transforming Growth Factor alpha: Mutation of Aspartic Acid 47 and Leucine 48 Results in Different Biological Activities. Mol. Cell. Biol., 8:1247-1252, 1988.*

Bork. Powers and Pitfalls in Sequence Analysis: The 70% Hurdle. Genome Research, 2000,10:398-400.*

Nam et al. Up-regulated transforming growth factor β-inducible gene h3 in rheumatoid arthritis mediates adhesion and migration of synoviocytes through αvβ3 integrin: Regulation by cytokines. Arthritis & Rheumatism, 2006, 54(9), 2734-2744.*

* cited by examiner

*Primary Examiner* — Vanessa L Ford
*Assistant Examiner* — Sandra Dillahunt
(74) *Attorney, Agent, or Firm* — Mintz Levin Cohn Ferris Glovsky and Popeo, P.C.; Kongsik Kim; Richard B. Emmons

(57) ABSTRACT

The present invention relates to a fusion peptide comprising dhFas-1 domain and MMP substrate and use thereof. More specifically, the present invention relates to a fusion peptide, comprising a) a dhFas-1 domain which is the fourth fas-1 domain of βig-h3 lacking H1 and H2 regions; b) a MMP (Matrix metalloproteinase) substrate; and c) a peptide comprising RGD motif and an use thereof for preventing and treating inflammatory disease. The fusion peptide of the present invention inhibits expension of rheumatoid arthritis by adhesion and migration of sinoviocytes and may be used for preventing or treating inflammatory disease by inhibiting infiltration of immune cells.

8 Claims, 61 Drawing Sheets

Nde I

5' catatgcaagccatgcctccagaagaactgaacaaactcttggcaaatgccaaggaacttaccaacatcctgaagtaccacattggtgatgaaatcctggt
tagcgggggcatcggggccctggtgcggctgaagtctctccaaggggacaaactggaagtcagctcgaaaaacaatgtagtgagtgtcaataaggagc
ctgttgccgaaaccgacatcatggaattcggaccactgggaatagcaggagtcgacggacaagaacgaggagattctctggcaggactcgag 3'

Xho I

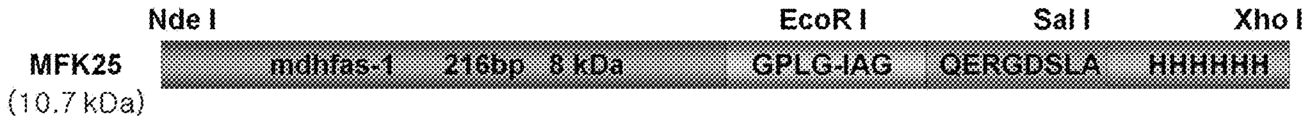

FIGURE 9A

FIGURE 10A
MFK23 (ug)
MMP 1 (ng)
3 3 3 3
— 5 10 50
Ab-Histidine 1:2000
Ab-bigh3 1:2000
normalized ratio (Histidine/big-h3)
1.2
0.9
0.6
0.3
MFK23(ug)
MMP 1(ng)
3 3 3 3
— 5 10 50

10mg/kg
1mg/kg
0.1mg/kg
Control

H&E

FUSION PEPTIDE COMPRISING DHFAS-1 DOMAIN AND MMP SUBSTRATE AND USE THEREOF FOR PREVENTING AND TREATING RHEUMATOID ARTHRITIS

CROSS-REFERENCE TO RELATED APPLICATIONS

This is a continuation of International Application No. PCT/KR2011/009318 filed on Dec. 2, 2011, which claims priority to Korean Application No. 10-2010-0121894 filed on Dec. 2, 2010, which applications are incorporated herein by reference.

TECHNICAL FIELD

The present invention relates to a fusion peptide comprising dhFas-1 domain and MMP substrate and use thereof for preventing and treating inflammatory disease. More specifically, the present invention relates to a fusion peptide, comprising a) a dhFas-1 domain which is the fourth fas-1 domain of βig-h3 lacking H1 and H2 regions; b) a MMP (Matrix metalloproteinase) substrate; and c) a peptide comprising RGD motif and an use thereof for preventing and treating inflammatory disease.

BACKGROUND ART

Inflammatory reactions result from tissue (cell) injury or infection by foreign pathogens and show a series of complex physiological responses such as enzyme activation, inflammation mediator release, body fluid infiltration, cell movement and tissue destruction, and external symptoms such as erythema, edema, pyrexia, pain and etc., in which various inflammation-mediating factors and immune cells in local blood vessels and body fluids are involved. Also, in some cases, these inflammation reactions result in acute inflammation, granuloma, and chronic inflammations such as rheumatoid arthritis (Goodwin J. S. et al., J. Clin. Immunol., 9: 295-314, 1989).

Rheumatoid arthritis (RA) is an autoimmune disease causing chronic inflammation in the whole body including articulations, and occurs more frequently in women than in men. Its cause has not been clearly known yet, but is assumed to be caused by genetic factors and environmental factors. Accordingly, many researches for finding out the cause of rheumatoid arthritis have been performed. Meanwhile, it has been recently reported that genetic factors play an important role in susceptibility and prognosis prediction of rheumatoid arthritis, and imbalance of epigenetic control on an overall immune response causes an autoimmune disease including rheumatoid arthritis (Richardson B. et al., Clin Immunol, 109, 72-79, 2003).

In rheumatoid arthritis, inflammation mainly occurs in synovial membrane of articulations within a body, and especially, is continued for 6 weeks or more. At the onset of rheumatoid arthritis, a lump ('Pannus') including various inflammatory cells is formed from blood of a synovial tissue, which destroys cartilage, erodes the bone around the articulation and causes deformities of in articulations. As a result of joint inflammation, articulation becomes swollen and painful, a movement range of an articulation is limited, and joint becomes red and warm to the touch.

This disease is caused by a disorder in a body immune system. Normally, an immune system within a body performs a role of defending the body against foreign substances such as bacteria. However, the disease is caused by a malfunction of the immune system that attacks the body itself due to unknown factors. Such a state refers to 'autoimmunity', in which based on the above described principle, symmetrical inflammation occurs in various joint, especially hand joint, resulting in gradual destruction of articulations for several years to several tens of years. Sometimes, the inflammation may invade other organs (such as lung, heart, eyes, blood vessel, nerves) as well as articulations. Also, the disease causes a disorder in a body function mainly in the prime of lifetime (around one's thirties), and thereby reduces the quality of life and the work efficiency, resulting in a great economic loss.

To date, although many researches on the cause of rheumatoid arthritis have been conducted, the exact cause of rheumatoid arthritis has not been known yet. However, various clinical therapeutic methods on rheumatoid arthritis have been developed, which are divided into a general conservative treatment, a drug therapy, an operation treatment, etc. Because the disease causes joint pain due to chronic inflammation, and deformation and dysfunction in the joint, the goal of treatment of rheumatoid arthritis is to inhibit pain and inflammation, and to minimize the dysfunction of articulations so that a patient can return to a normal life. At present, the most frequently used therapeutic method is a drug therapy. For the drug therapy, according to symptoms, aspirin & non-steroidal anti-inflammatory drugs, a low dose oral steroid, disease modifying anti-rheumatic drugs (DMARDs) (such as an antimalarial drug, sulfasalazine, gold compounds, penicillamine, immunosuppressive drugs (methotrexate (MTX), Immuran), etc.), intra-articular steroid injections and biologicals (such as tumor necrosis factor blocker (etanercept, infliximab, adalimumab), an interleukin-1 receptor antagonist (anakinra), and an anti-CD20 antibody (rituximab)) are used. However, such a drug therapy has a disadvantage in that it may cause side effects such as gastrointestinal disorders, hepatopathy, renal failure, and infection. Accordingly, it is urgently required to develop advanced therapeutic agents with reduced side effects, which can improve manifestations of rheumatoid arthritis, such as inflammation, edema, abnormal neovascularization, bone and cartilage destruction.

Collagen-induced arthritis (CIA) has been used as an animal model of T lymphocytic rheumatoid arthritis (Autoimmunity to Type II collagen: Experimental model of arthritis, J. Exp. Med. 146; 857-868 (1977)). When an experimental mouse susceptible to arthritis is injected with collagen II, arthritis is caused together with formation of pannus and erosion of bones and cartilage within 2 weeks. Like rheumatoid arthritis, collagen-induced arthritis (CIA) also causes a humoral/cellular immune response to collagen.

Meanwhile, a extracellular matrix protein is a constituent playing an important role in tissue frame configuration, and has been reported to perform an important role in maintaining and controlling the shape and function of a tissue through many researches. TGF-β-inducible gene-h3 (βig-h3), a matrix protein induced by transforming growth factor-β (TGF-β), is a protein with a recently known molecular structure, and performs an important role in the control of cellular functions such as adhesion, migration, differentiation and proliferation.

βig-h3 known as a gene related to TGF-β was originally identified by Skonier, et al. It was identified in an A549 cell line (human lung adenocarcinoma cell line) treated with TGF-β1 during in cDNA selection, and was reported to be increased to 20 times or more for 2 days from treatment with TGF-β1 (Stonier, J. et al., DNA cell Biol. 11, 511, 1992). Through DNA sequence analysis of βig-h3, it was found that a βig-h3 protein includes 683 amino acids with an amino-terminal secretory sequence, and a carboxy-terminal Arg-Gly-Asp (RGD) sequence ligand-recognizable by integrins.

SUMMARY

When the inventors of the present invention have researched on the function of βig-h3, they have confirmed that a fusion peptide comprising dhFas-1 domain which is the fourth fas-1 domain of βig-h3 lacking H1 and H2 regions (hereinafter, referred to as 'dhFas-1'; human dhFas-1: 'hsd-hFas-1', mouse dhFas-1: 'mdhFas-1'), more specifically, a fusion peptide comprising a dhFas-1 domain which is the fourth fas-1 domain of βig-h3 lacking H1 and H2 regions, a MMP (Matrix metalloproteinase) substrate, and a peptide comprising RGD, has an effect on inflammatory disease, and then completed this invention based on the finding.

Accordingly, an object of the present invention is to provide a fusion peptide, comprising a) a dhFas-1 domain which is the fourth fas-1 domain of βig-h3 lacking H1 and H2 regions; b) a MMP (Matrix metalloproteinase) substrate; and c) a peptide comprising RGD motif.

Another object of the present invention is to provide polynucleotide encoding the fusion peptide.

Still another object of the present invention is to provide a vector comprising a promoter and the polynucleotide operably linked to the promoter.

Still another object of the present invention is to provide a host cell transformed with the vector.

Still another object of the present invention is to provide a pharmaceutical composition for preventing and treating inflammatory disease, which comprises the peptide as an active ingredient.

Still another object of the present invention is to provide a pharmaceutical composition for preventing and treating inflammatory disease, which comprises the vector as an active ingredient.

Still another object of the present invention is to provide a method for preventing and treating inflammatory disease comprising administering to a subject in need thereof an effective amount of a fusion peptide, comprising a) a dhFas-1 domain which is the fourth fas-1 domain of βig-h3 lacking H1 and H2 regions; b) a MMP (Matrix metalloproteinase) substrate; and c) a peptide comprising RGD motif.

Still another object of the present invention is to provide a method for preventing and treating inflammatory disease comprising administering to a subject in need thereof an effective amount of a vector comprising a promoter and a polynucleotide operably linked to the promoter, wherein the polynucleotide encodes a fusion peptide, comprising a) a dhFas-1 domain which is the fourth fas-1 domain of βig-h3 lacking H1 and H2 regions; b) a MMP (Matrix metalloproteinase) substrate, and an MMP consensus substrate; and c) a peptide comprising RGD motif.

Still another object of the present invention is to provide the use of a fusion peptide, comprising a) a dhFas-1 domain which is the fourth fas-1 domain of βig-h3 lacking H1 and H2 regions; b) a MMP (Matrix metalloproteinase) substrate, and an MMP consensus substrate; and c) a peptide comprising RGD motif.

Still another object of the present invention is to provide the use of a vector for preparing an agent for preventing and treating inflammatory disease, wherein the vector comprises a promoter and a polynucleotide operably linked to the promoter, wherein the polynucleotide encodes a fusion peptide, comprising a) a dhFas-1 domain which is the fourth fas-1 domain of βig-h3 lacking H1 and H2 regions; b) a MMP (Matrix metalloproteinase) substrate, and an MMP consensus substrate; and c) a peptide comprising RGD motif.

To achieve the above object, the present invention provides a fusion peptide, comprising a) a dhFas-1 domain which is the fourth fas-1 domain of βig-h3 lacking H1 and H2 regions; b) a MMP (Matrix metalloproteinase) substrate; and c) a peptide comprising RGD motif.

To achieve another object, the present invention provides polynucleotide encoding the peptide.

To achieve still another object, the present invention provides a vector comprising a promoter and the polynucleotide operably linked to the promoter.

To achieve still another object, the present invention provides a host cell transformed with the vector.

To achieve still another object, the present invention provides a pharmaceutical composition for preventing and treating inflammatory disease, which comprises the peptide as an active ingredient.

To achieve still another object, the present invention provides a pharmaceutical composition for preventing and treating inflammatory disease, which comprises the vector as an active ingredient.

To achieve still another object, the present invention provides a method for preventing and treating inflammatory disease comprising administering to a subject in need thereof an effective amount of a fusion peptide, comprising a) a dhFas-1 domain which is the fourth fas-1 domain of βig-h3 lacking H1 and H2 regions; b) a MMP (Matrix metalloproteinase) substrate; and c) a peptide comprising RGD motif.

To achieve still another object, the present invention provides a method for preventing and treating inflammatory disease comprising administering to a subject in need thereof an effective amount of a vector comprising a promoter and a polynucleotide operably linked to the promoter, wherein the polynucleotide encodes a fusion peptide, comprising a) a dhFas-1 domain which is the fourth fas-1 domain of βig-h3 lacking H1 and H2 regions; b) a MMP (Matrix metalloproteinase) substrate; and c) a peptide comprising RGD motif.

To achieve still another object, the present invention provides the use of a fusion peptide for preparing an agent for preventing and treating inflammatory disease, wherein the fusion peptide, comprising a) a dhFas-1 domain which is the fourth fas-1 domain of βig-h3 lacking H1 and H2 regions; b) a MMP (Matrix metalloproteinase) substrate; and c) a peptide comprising RGD motif.

To achieve still another object, the present invention provides the use of a vector for preparing an agent for preventing and treating inflammatory disease, wherein the vector comprises a promoter and a polynucleotide operably linked to the promoter, wherein the polynucleotide encodes a fusion peptide, comprising a) a dhFas-1 domain which is the fourth fas-1 domain of βig-h3 lacking H1 and H2 regions; b) a MMP (Matrix metalloproteinase) substrate; and c) a peptide comprising RGD motif.

Accordingly, the fusion peptide of the present invention inhibits expension of rheumatoid arthritis by adhesion and migration of sinoviocytes and may be used for preventing or treating inflammatory disease by inhibiting infiltration of immune cells.

BRIEF DESCRIPTION OF DRAWINGS

FIG. 15C is a result graph of a comparative experiment on the inhibition extent of NIH3T3 cell line adhesion by MFK24, and mixed compositions of dhFas-1 peptide and RGDSP peptide, and dhFas-1 peptide and RGDSP (SEQ ID NO: 91 peptide (Adhesion(%): cell adherence(relative adherence with respect to 100% of control group), Migration(%): cell migration (relative migration respect to 100% of control group), Concentration(uM): concentration of added peptide, MFK24: concentration of added MFK24, dhfas-1: concentration of added dhfas-1, RGDSP (SEQ ID NO: 9): concentration of added peptide including an amino acid sequence of RGDSP) (SEQ ID NO: 9).

groups administered with MFK23 in amounts of 1 mg/kg, 10 mg/kg, and 30 mg/kg per day; H&E: photograph showing the result of hematoxylin, eosin stain; CD31: a photograph showing the result of an immunohistochemistry test using anti-CD31 antibody as an endothelial cell marker; ICAM-1: a photograph showing the result of an immunohistochemistry test using an anti-ICAM-1 (intercellular adhesion molecule-1) antibody).

Figure 19:
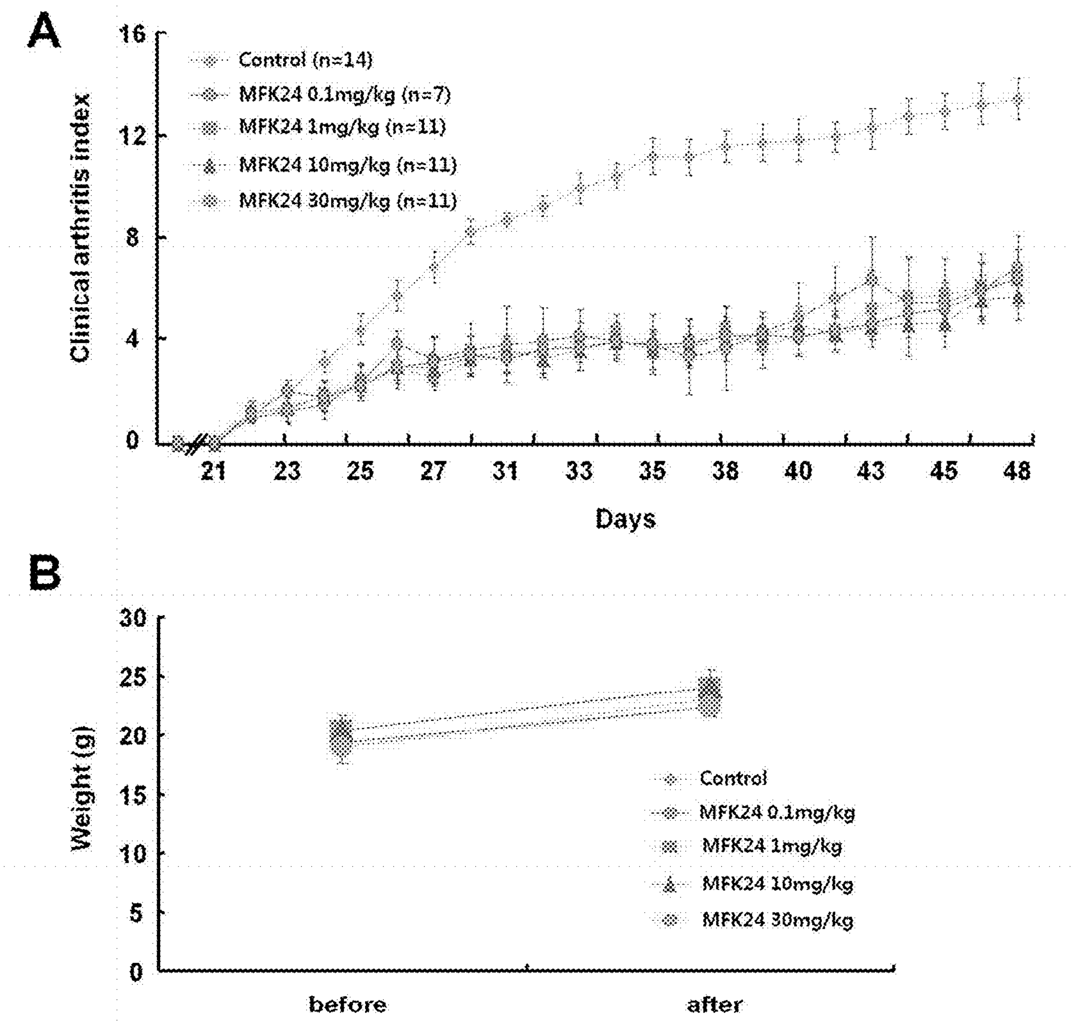

FIG. 19 shows the measurement result (A) of an arthritis inhibiting effect by MFK24 by a clinical arthritis index in a mouse CIA model, and the measurement result (B) of the weight of the experimental mouse (Clinical Arthritis Index: Clinical Arthritis Index; Days: days since administration of collagen injection for arthritis induction; Control: control group administered with PBS instead of peptide; MFK24 0.1 mg/kg, MFK24 1 mg/kg, MFK24 10 mg/kg, MFK24 30 mg/kg: groups administered with MFK24 in amounts of 0.1 mg/kg, 1 mg/kg, 10 mg/kg, and 30 mg/kg per day; weight (g): body weight(g); before: before administration of peptide (on 22nd day); after: after administration of peptide (on 48th day)).

Figure 20:
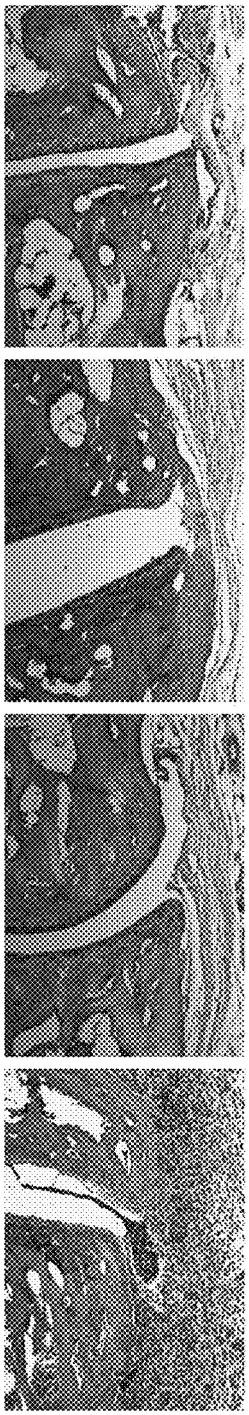

FIG. 20 shows a Synovial membrane tissue of a CIA mouse model treated with MFK24, which was observed through HEstain (control: control group administered with PBS instead of peptide; 0.1 mg/kg, 1 mg/kg, 10 mg/kg: groups administered with MFK24 in amounts of 0.1 mg/kg, 1 mg/kg 10 mg/kg per day; H&E: a photograph showing the result of hematoxylin, eosin stain).

Figure 21:
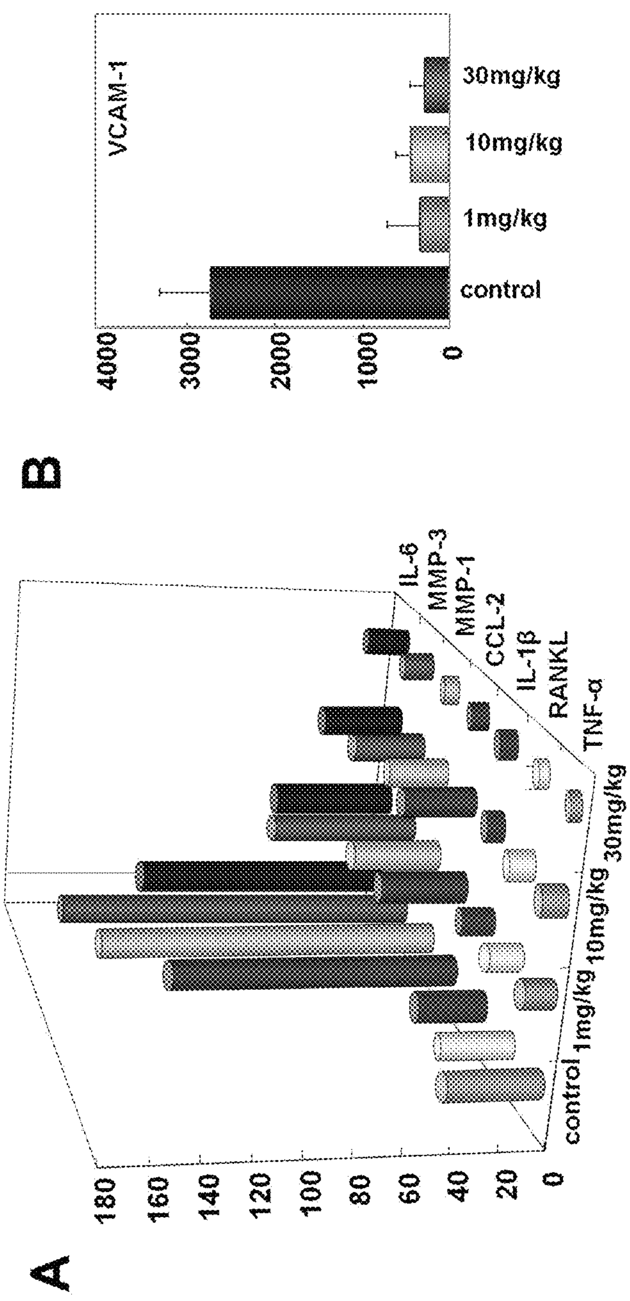

FIG. 21 shows the number of transcripts of inflammatory mediators in a CIA mouse model articulation tissue treated with MFK24 (control: control group administered with PBS instead of peptide; 1 mg/kg, 10 mg/kg, 30 mg/kg: groups administered with MFK24 in amounts of 1 mg/kg, 10 mg/kg 30 mg/kg per day; TNF-a: tumor necrosis factor alpha; RANKL: Receptor Activator for Nuclear Factor κ B Ligand; IL-1β: interleukin 1beta; CCL-2: chemokine (C-C motif) ligand 2; MMP-1: matrix metalloproteinase-1; MMP-3: matrix metalloproteinase-3; IL-6: interleukin6; VCAM-1: vascular cell adhesion molecule-1).

Figure 22:
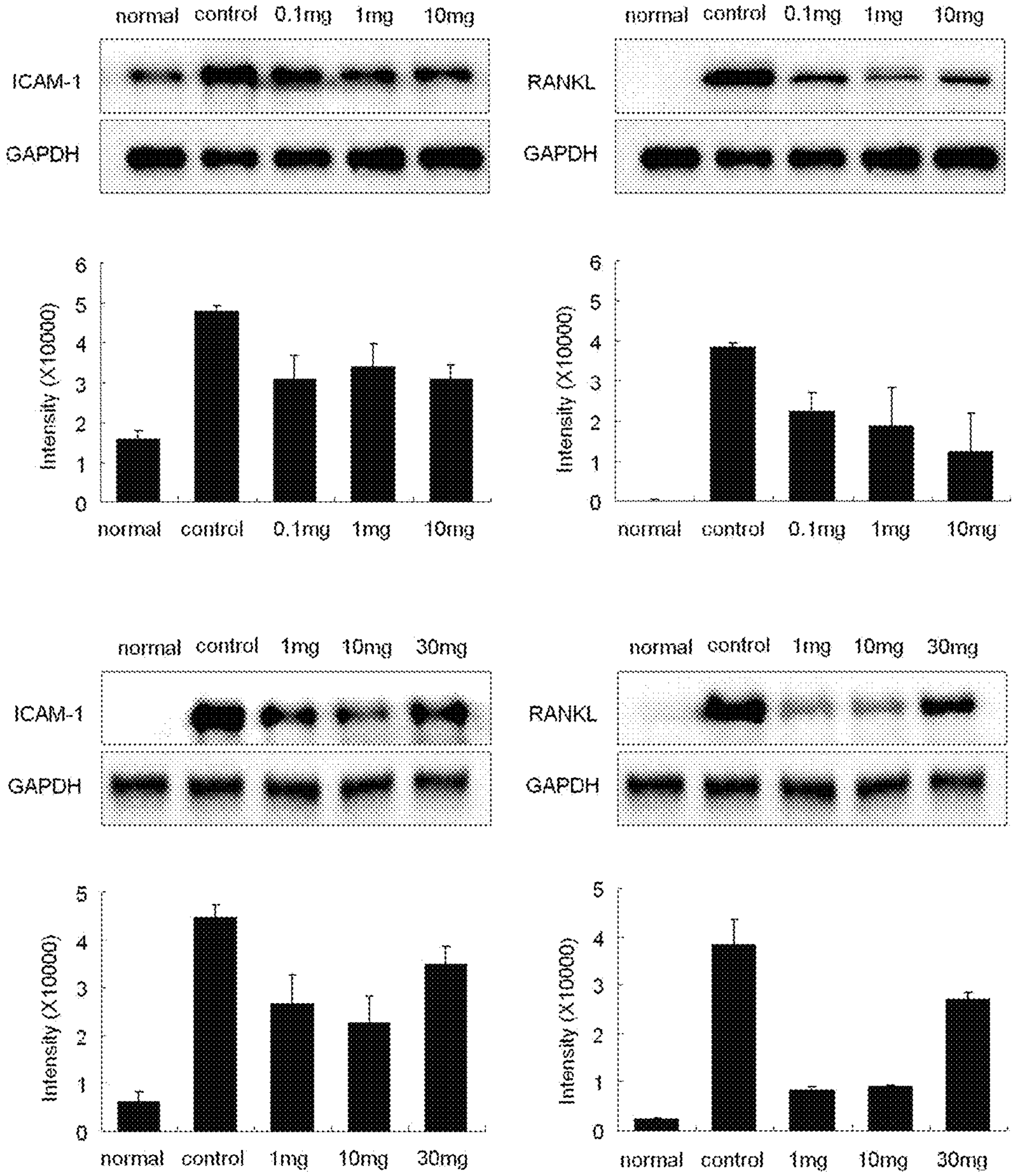

FIG. 22 is the result of immunoblot, which shows that the expression of ICAM-1 and RANKL was inhibited dependently on the treatment concentrations in a CIA mouse model treated with MFK24 (normal: a group in which arthritis was not induced; control: control group administered with PBS instead of peptide; 1 mg/kg, 10 mg/kg, 30 mg/kg: groups administered with MFK24 in amounts of 1 mg/kg, 10 mg/kg 30 mg/kg per day; RANKL: Receptor Activator for Nuclear Factor κ B Ligand; ICAM-1: intercellular adhesion molecule-1; GAPDH: Glyceraldehyde 3-phosphate dehydrogenase).

Figure 23:
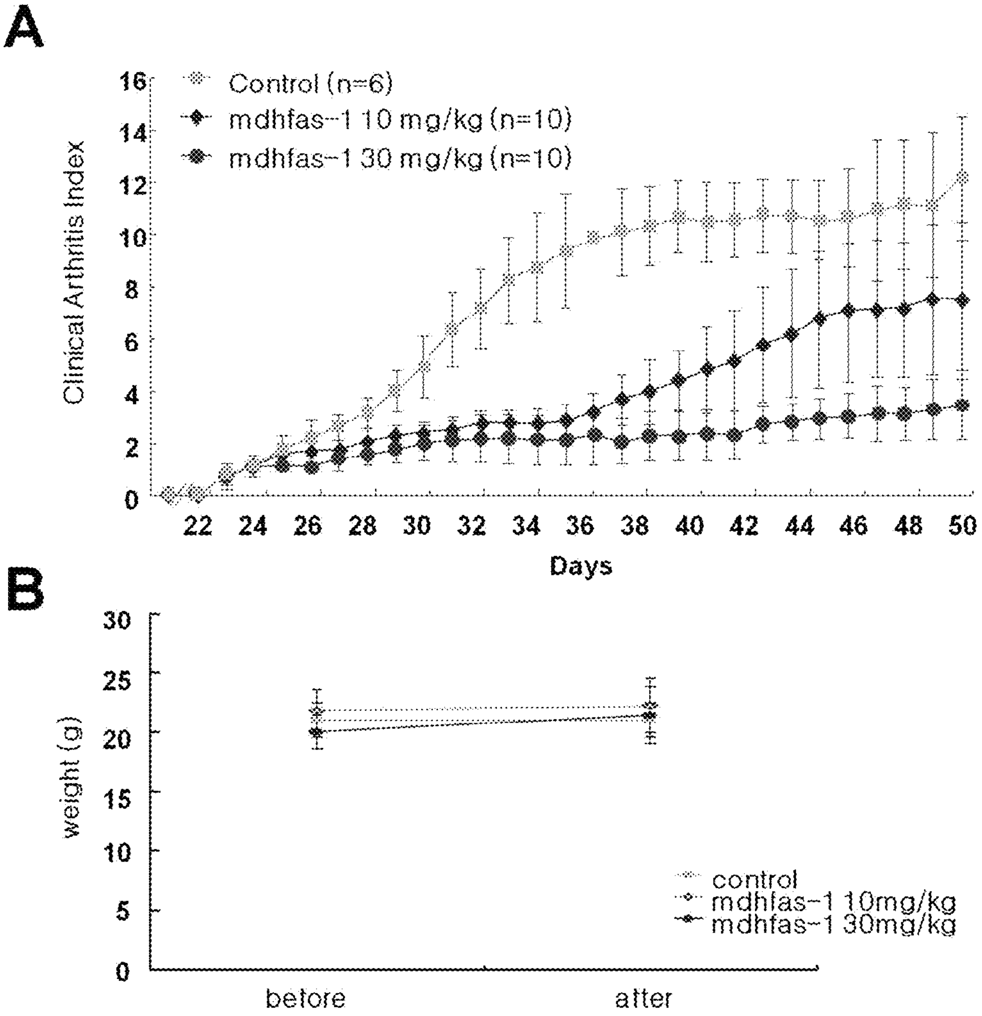

FIG. 23 shows the measurement result (A) of an arthritis inhibiting effect by mdhFas-1 by a clinical arthritis index in a mouse CIA model, and the measurement result (B) of the weight of the experimental mouse (Clinical Arthritis Index: clinical arthritis index; Days: days since administration of collagen injection for arthritis induction; Control: control group administered with PBS instead of peptide; mdhfas-1 10 mg/kg, mdhfas-1 30 mg/kg: groups administered with mdhfas-1 in amounts of 10 mg/kg, and 30 mg/kg per day; weight(g): body weight(g); before: before administration of peptide (on 22nd day); after: after administration of peptide (on 48th day)).

Figure 24:
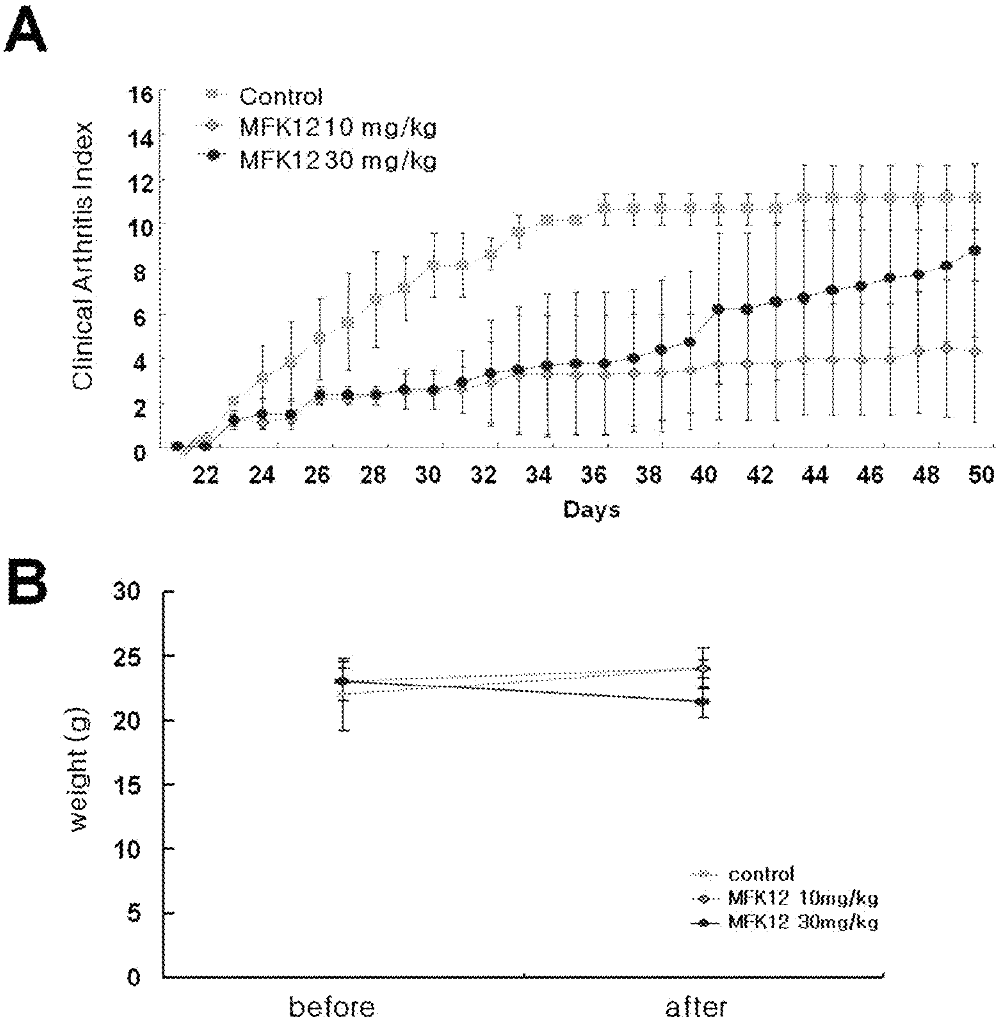

FIG. 24 shows the measurement result (A) of an arthritis inhibiting effect by MFK12 by a clinical arthritis index in a mouse CIA model, and the measurement result (B) of the weight of the experimental mouse (Clinical Arthritis Index: clinical arthritis index; Days: days since administration of collagen injection for arthritis induction; Control: control group administered with PBS instead of peptide; MFK12 10 mg/kg, MFK12 30 mg/kg: groups administered with MFK12 in amounts of 10 mg/kg, 30 mg/kg per day; weight (g): body weight(g); before: before administration of peptide (on 22nd day); after: after administration of peptide (on 48th day)).

Figure 25:
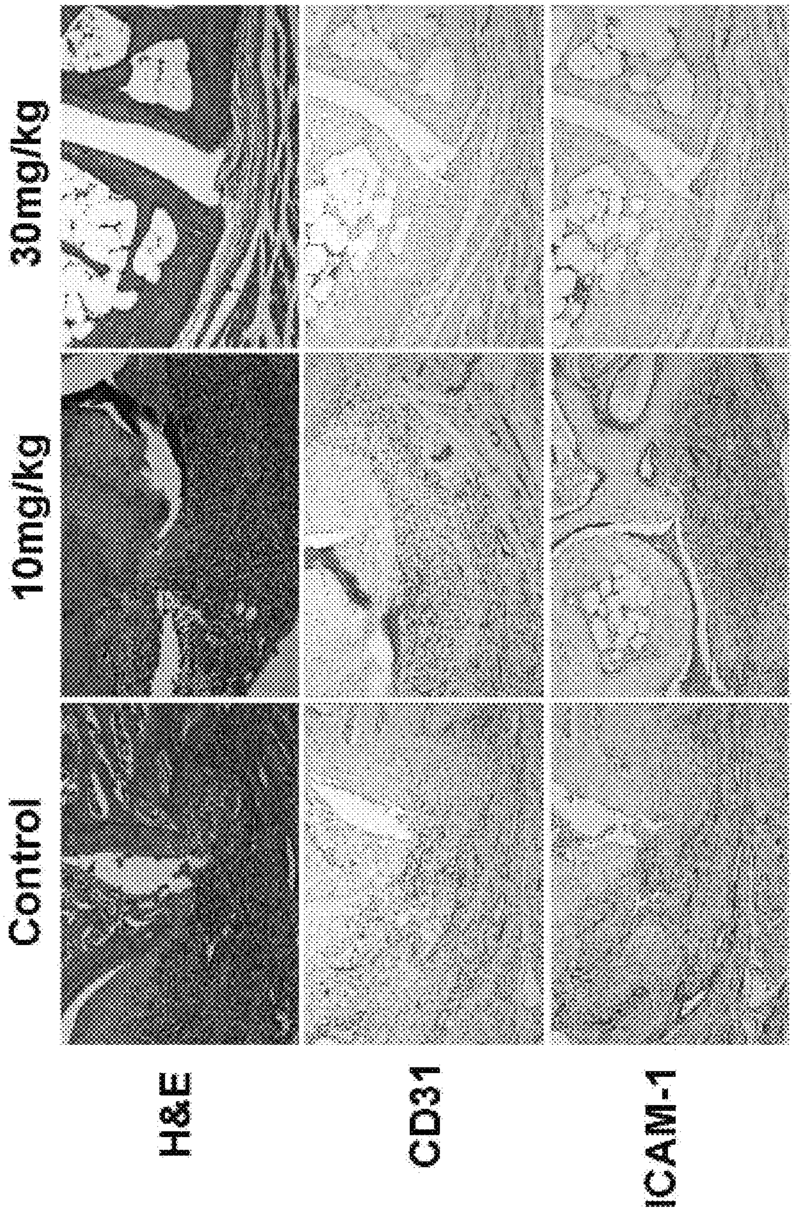

FIG. 25 shows a Synovial membrane tissue of a CIA mouse model treated with MFK12, which was observed through HEstain (Control: control group administered with PBS instead of peptide; 10 mg/kg, 30 mg/kg: groups administered with MFK12 in amounts of 10 mg/kg, 30 mg/kg per day; H&E: a photograph showing the result of hematoxylin, eosin stain; CD31: a photograph showing the result of an immunohistochemistry test using anti-CD31 antibody as an endothelial cell marker; ICAM-1: a photograph showing the result of an immunohistochemistry test using an anti-ICAM-1 (intercellular adhesion molecule-1) antibody).

Figure 26:
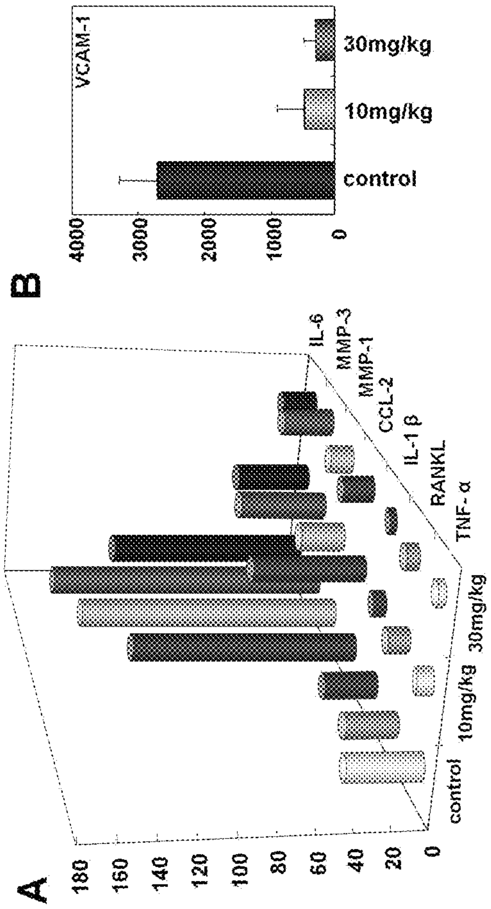

FIG. 26 shows the number of transcripts of inflammatory mediators in a CIA mouse model articulation tissue treated with MFK12 (control: control group administered with PBS instead of peptide; 10 mg/kg, 30 mg/kg: groups administered with MFK12 in amounts of 10 mg/kg 30 mg/kg per day; TNF-a: tumor necrosis factor alpha; RANKL: Receptor Activator for Nuclear Factor κ B Ligand; IL-1β: interleukin) beta; CCL-2: chemokine (C-C motif) ligand 2; MMP-1: matrix metalloproteinase-1; MMP-3: matrix metalloproteinase-3; IL-6: interleukin6; VCAM-1: vascular cell adhesion molecule-1).

Figure 27:
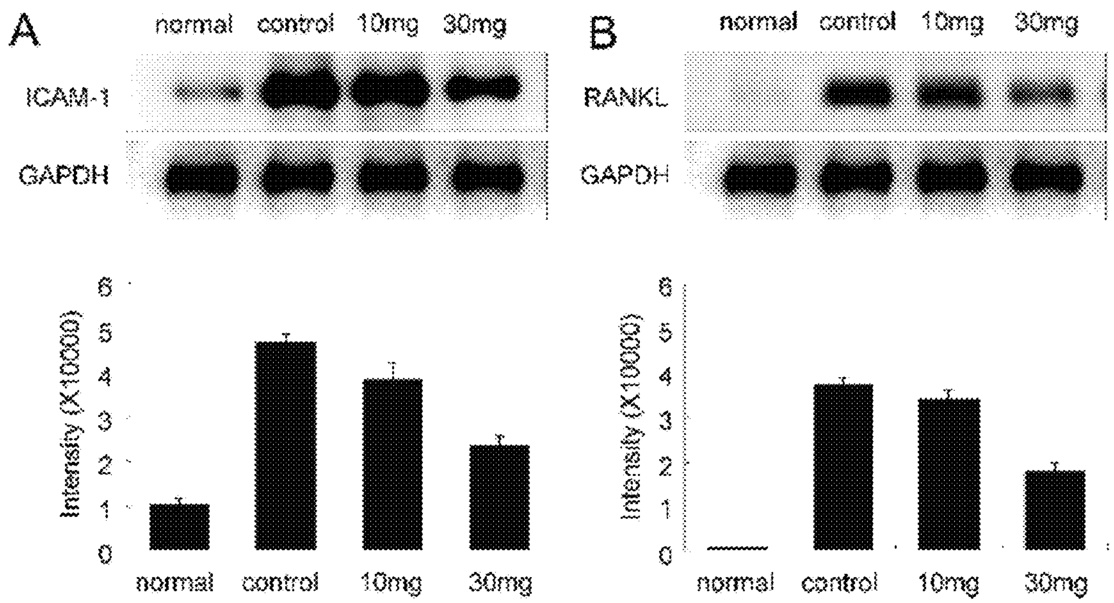

FIG. 27 is the result of immunoblot, which shows that the expression of ICAM-1 and RANKL was inhibited dependently on the treatment concentrations in a CIA mouse model treated with MFK12 (normal: a group in which arthritis was not induced; control: control group administered with PBS instead of peptide; 10 mg/kg, 30 mg/kg: groups administered with MFK12 in amounts of 10 mg/kg 30 mg/kg per day; RANKL: Receptor Activator for Nuclear Factor κ B Ligand; ICAM-1: intercellular adhesion molecule-1; GAPDH: Glyceraldehyde 3-phosphate dehydrogenase).

Figure 28A:
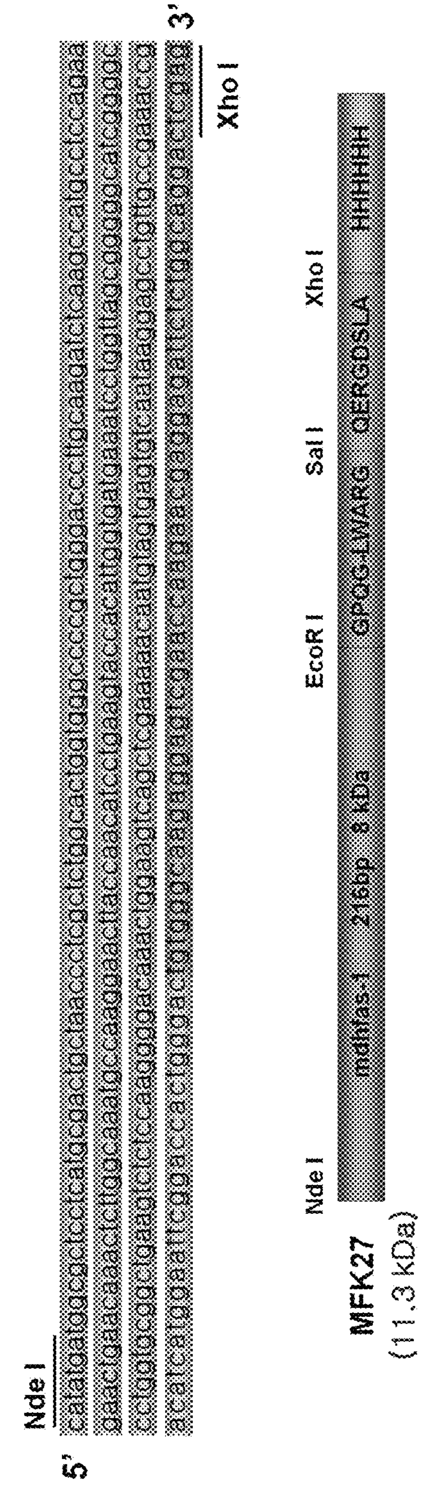
Figure 28B:
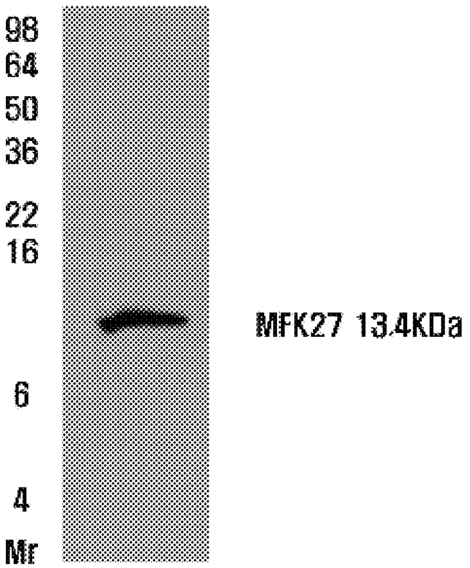

FIG. 28 shows a sequence of an MFK27 peptide, in which mdhFas-1 as a basic structure is linked to an MMP 3 substrate peptide and a QERGDSLA (SEQ ID NO: 10) peptide.

Figure 29A:
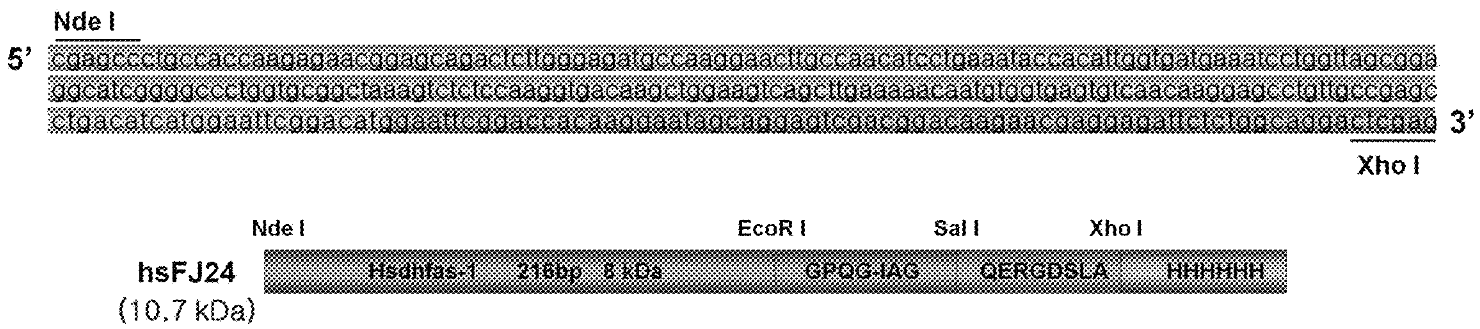
Figure 29B:
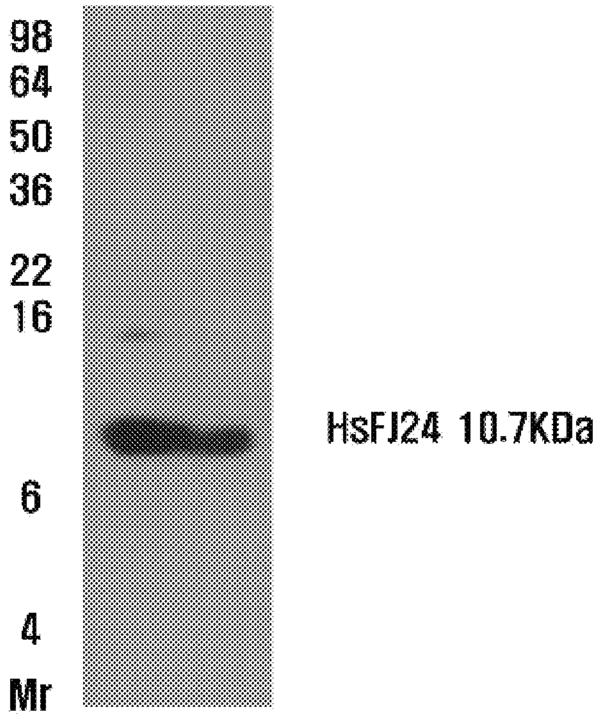

FIG. 29 shows a sequence of an hsFJ24 peptide, in which hsdhFas-1 as a basic structure is linked to an MMP1 substrate peptide and a QERGDSLA (SEQ ID NO: 10) peptide.

Figure 30A:
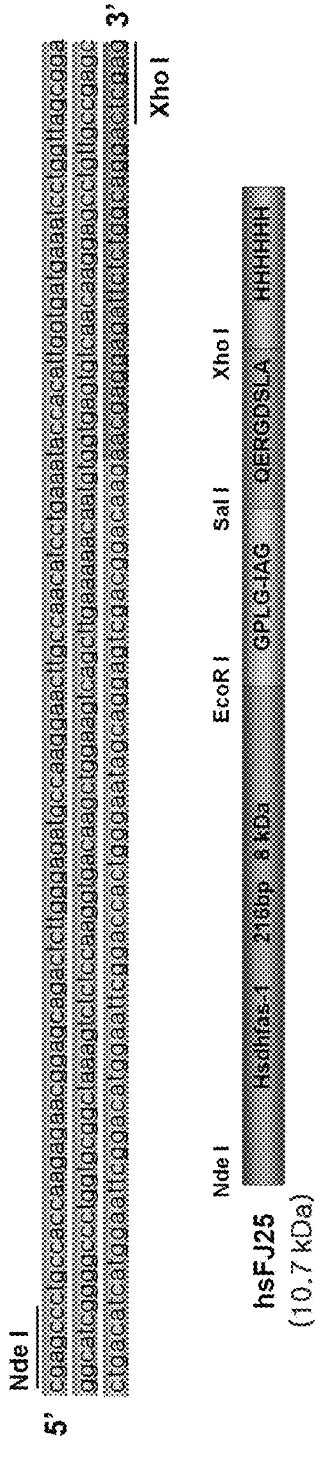
Figure 30B:
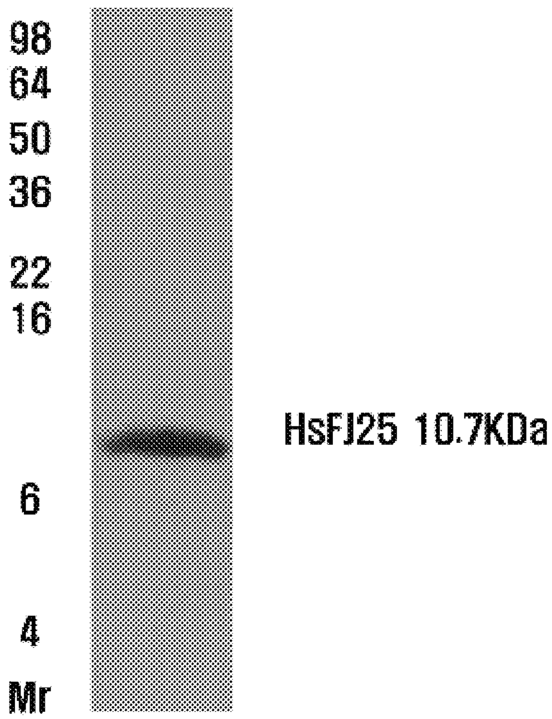

FIG. 30 shows a sequence of an hsFJ25 peptide, in which hsdhFas-1 as a basic structure is linked to an MMP consensus substrate peptide and a QERGDSLA (SEQ ID NO: 10) peptide.

Figure 31A:
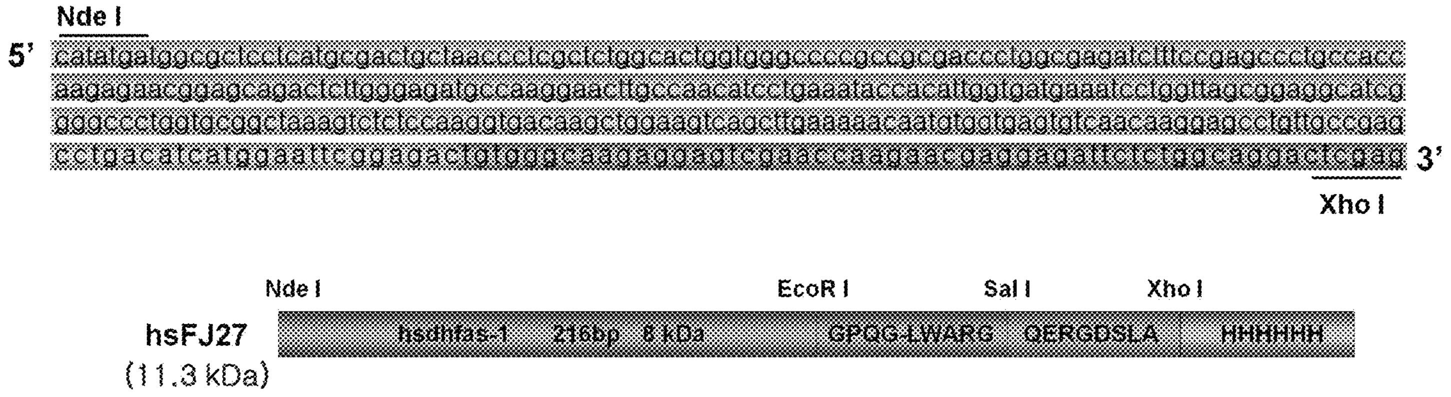
Figure 31B:
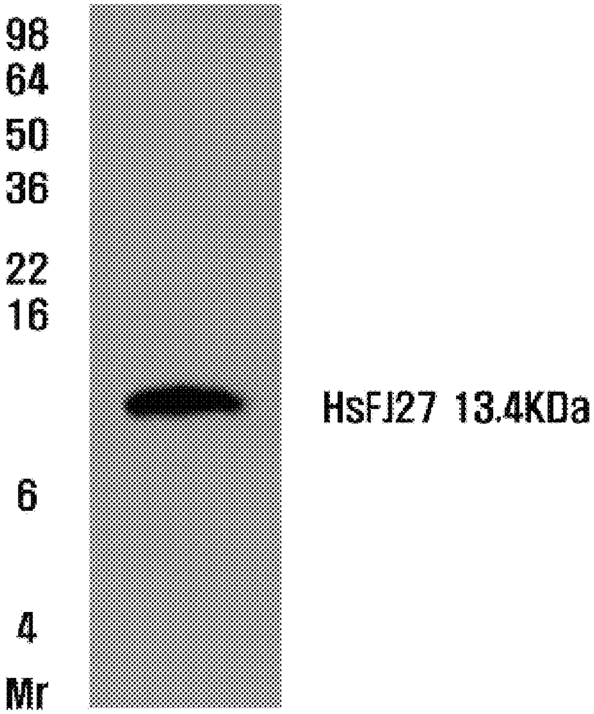

FIG. 31 is the result of immunoblot, which shows a sequence of HsFJ27, and the expression of HsFJ27 recombinant peptide.

Figure 32:
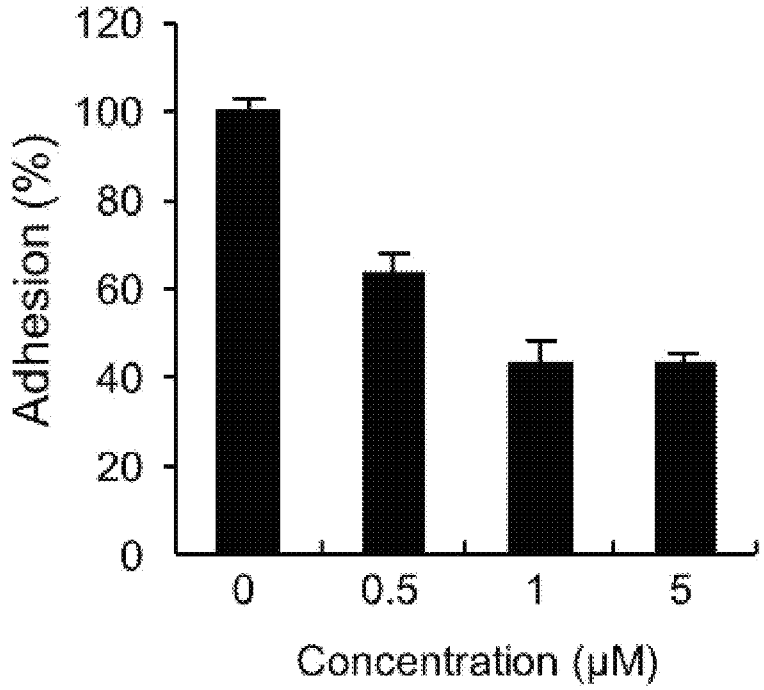

FIG. 32 is the result showing that adhesion of βig-h3-mediated NIH3T3 cell line were concentration-dependently inhibited by MFK27 (Adhesion(%): cell adherence (relative adherence with respect to 100% of control group).

Figure 33:
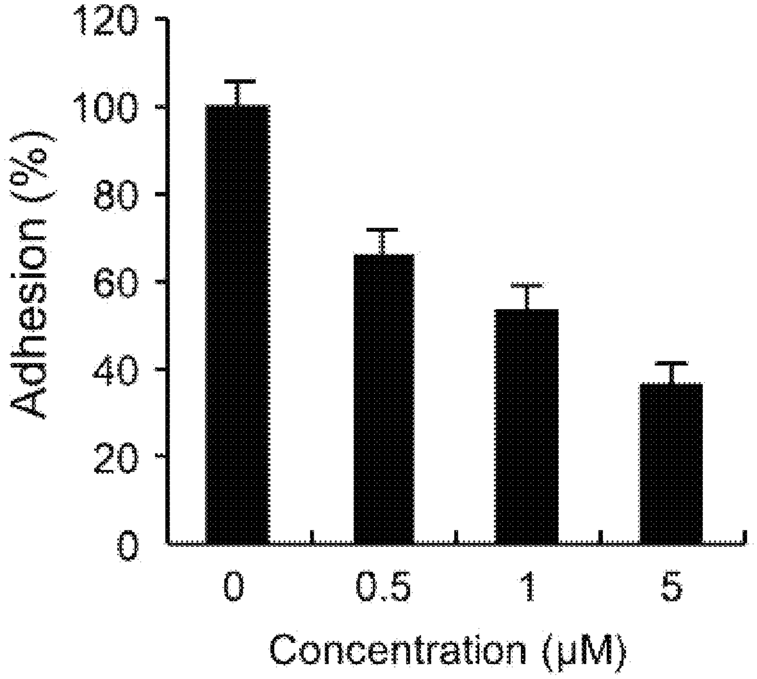

FIG. 33 is the result showing that adhesion of βig-h3-mediated FLS cell line were concentration-dependently inhibited by HsFJ24 (Adhesion(%): cell adherence (relative adherence with respect to 100% of control group).

Figure 34:
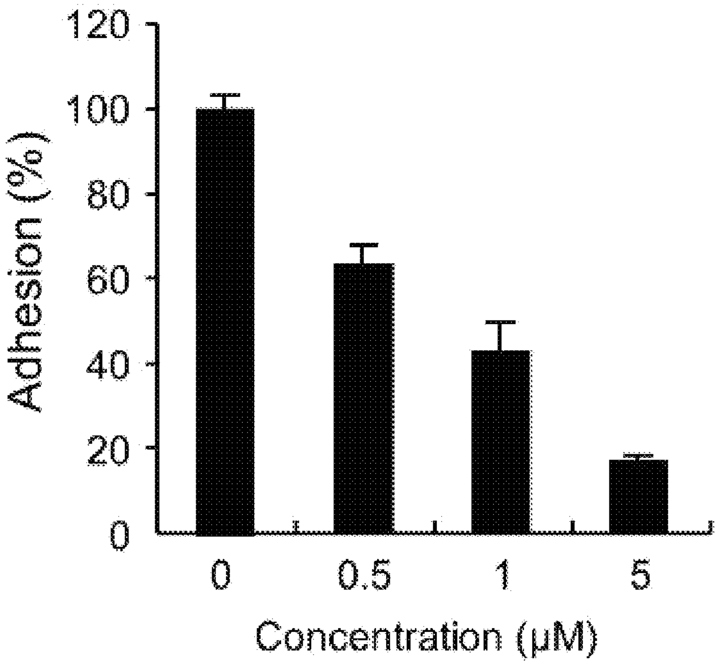

FIG. 34 is the result showing that adhesion of βig-h3-mediated FLS cell line were concentration-dependently inhibited by HsFJ25 (Adhesion(%): cell adherence (relative adherence with respect to 100% of control group).

Figure 35:
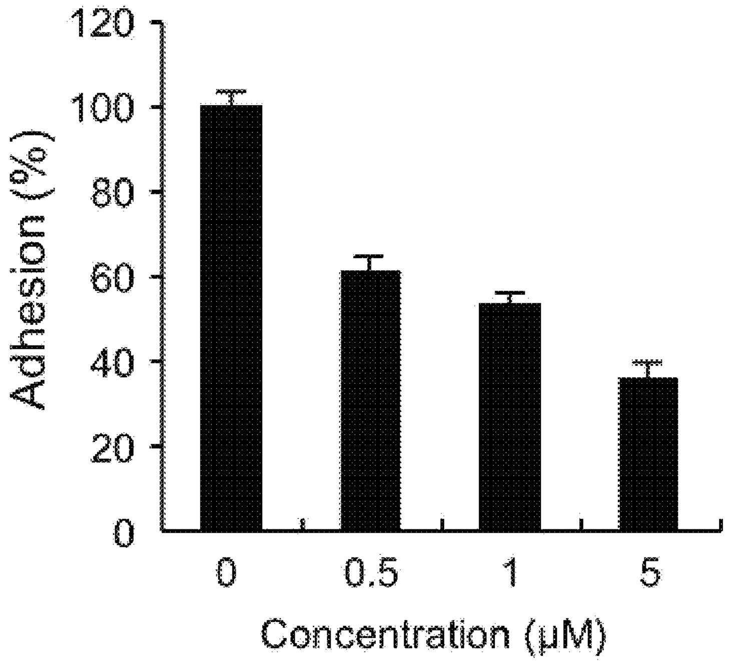

FIG. 35 is the result showing that adhesion of βig-h3-mediated FLS cell line were concentration-dependently inhibited by HsFJ27 (Adhesion(%): cell adherence (relative adherence with respect to 100% of control group).

DETAILED DESCRIPTION

The present invention provides a fusion peptide, comprising a) a dhFas-1 domain which is the fourth fas-1 domain of βig-h3 lacking H1 and H2 regions; b) a MMP (Matrix metalloproteinase) substrate; and c) a peptide comprising RGD motif.

The inventors of the present invention have researched the method for increasing the therapeutic efficiency of dhFas-1. Then, they found when a dhFas-1 fragment was fused to a peptide comprising RGD motif, the effect was not significantly increased. However, when the dhfas-1 domain and the peptide comprising RGD motif were connected by MMP (Matrix metalloproteinase) substrates, therapeutic effect for inflammatory disease was significantly increased.

The fusion peptide of the present invention is characterized in that it the peptide comprising a) a dhFas-1 domain which is the fourth fas-1 domain of βig-h3 lacking H1 and H2 regions; b) a MMP (Matrix metalloproteinase) substrate; and c) a peptide comprising RGD motif is sequentially linked.

βig-h3 is an extracellular matrix protein induced by TGF-β in various kinds of cells including human melanoma cells, mammary epithelial cells, keratinocytes and lung fibroblasts (Skonier, J. et al., DNA Cell Biol., 13, 571, 1994) and fibroblast-like synoviocyte (Nam, E. J. et al., Arthritis Rheum., 54, 2734, 2006). βig-h3 includes 4 repetitive homologous internal domains together with an RGD motif. The domain is found as a highly conservative sequence in a secreted protein or a membrane protein of various species including mammalia, insect, sea urchin, plant, yeast and bacteria. It was found that proteins comprising the conservative sequence include periostin, fasciclin I, seaurchin HLC-2, Algal-CAM and mycobacterium MPB70, etc. (Kawamoto, T. et al., Biochem. Biophys. Acta., 1395, 288, 1998). The homologous domains (referred to as fas-1 domain) conservatively found in these proteins include 110 to 140 amino acids, and especially include two branches (H1 and H2) including about 10 highly homologous amino acids.

dhFas-1 refers to an amino acid chain prepared by removing H1 and H2 regions from the fourth fas-1 domain of βig-h3. A βig-h3 protein includes an RGD motif as a ligand recognition site, and fas-1 domains as 4 repetitive internal domains. The fourth fas-1 domain includes a motif interacting with a 3β1 integrin, and an YH motif that includes a tyrosin-histidine amino acid sequence, and mediates the adhesion of a fibroblast. Furthermore, within the fourth fas-1 domain, H1 and H2 consisting of about 10 very highly homologous amino acids exist.

In the present invention, as dhFas-1, any amino acid chain may be used as long as it is prepared by removing H1 and H2 regions from the fourth fas-1 domain of known βig-h3. Preferably, it may be mouse-derived dhFas-1 (mdhFas-1) or human-derived dhFas-1 (hsdhFas-1). More preferably, it may be an amino acid sequence represented by SEQ ID NO: 1 or SEQ ID NO: 3. Also, dhFas-1 may be prepared by a conventional method (Korean Patent Publication 10-2004-0086708).

In the present invention, as an amino acid chain comprising RGD, any amino acid chain may be used as long as it comprises an RGD (arginine-glycine-aspartic acid) sequence capable of blocking integrin. Preferably, it may be an amino acid sequence represented by SEQ ID NO: 9 or SEQ ID NO: 10.

An MMP substrate refers to a short amino acid chain decomposed by matrix metalloproteinase (MMP).

It is known that in rheumatoid arthritis, a synovial membrane cell destroys a cartilage matrix through secretion of enzymes such as MMP and cathepsin. In synovial tissues of rheumatoid arthritis, MMP-1 and MMP-3 was highly expressed and are activated state and along with MMPs were also upregulated in expression. Such MMP includes about 19 kinds of various enzymes, and is largely divided into 4 types of MMPs, that is, collagenase, gelatinase, stromelysin, and membrane types of MMPs (MT-MMP). Especially, collagenase-1 (MMP-1), collagenase-2 (MMP-8), and collagenase-3 (MMP-13) are known as main collagenases destroying original collagen.

The different MMPs are involved in inflammatory disease. MMP-9 expression is associated with endotoxin shock, a kind of acute inflammatory disease, MMP-2 and MMP-9 are associated with multiple sclerosis, a kind of inflammatory disease, MMP-2, MMP-3, MMP-7, MMP-9, MMP-12 and MMP-13 are associated with atherosclerosis including stroke and cardia infarction. And MMP-2 and MMP-9 are associated with mitral stenosis, MMP-8 and MMP-9 are associated with periodontitis and peri-implantitis, MMP-12 is associated with chronic obstructive pulmonary disease, MMP-2, MMP-8, and MMP-9 are associated with asthma, MMP-7 and MMP-12 are associated with pulmonary fibrosis, MMP-2, MMP-3, MMP-8 and MMP-9 are associated with hepatitis, MMP-2, MMP-8, and MMP-9 are associated with pancreatitis and meningitis (Jialiang Hu. et al., *Nat. Rev. Drug. Discov.* 6:480-498, 2007). Therefore, MMP substrate may be different depending on disorder type. Thus, MMP substrate of the present invention may comprise a diverse type.

MMP substrate of the present invention refers to a short peptide degraded by MMP, but not limited thereto, specifically, MMP-1 substrate, MMP-2 substrate, MMP-3 substrate, MMP-7 substrate, MMP-8 substrate, MMP-9 substrate, MMP-12 substrate, MMP-13 substrate and MMP consensus substrate. The MMP1 substrate refers to a short amino acid chain decomposed by MMP-1. The MMP-2 substrate refers to a short amino acid chain decomposed by MMP-2. The MMP-3 substrate refers to a short amino acid chain decomposed by MMP-3. The MMP-7 substrate refers to a short amino acid chain decomposed by MMP-7. The MMP-8 substrate refers to a short amino acid chain decomposed by MMP-8. The MMP-9 substrate refers to a short amino acid chain decomposed by MMP-9. The MMP-12 substrate refers to a short amino acid chain decomposed by MMP-12. The MMP-13 substrate refers to a short amino acid chain decomposed by MMP-13. The MMP consensus substrate refers to a short amino acid chain decomposed by MMP-1, MMP-2 and MMP-3.

In the present invention, as the MMP substrate, any amino acid chain may be used as long as it exists between the dhFas-1 and an amino acid chain containing RGD capable of blocking integrin, and increases the adhesion efficiency of the dhFas-1 and the RGD-containing amino acid chain by being decomposed at the start point of the progress of inflammation. Preferably, it may be an amino acid chain comprising an amino acid sequence represented by LGVR (SEQ ID NO: 69), QGIA (SEQ ID NO: 70), LGLW (SEQ ID NO: 71) or LGIA (SEQ ID NO: 72). More preferably, it may be an amino acid chain comprising an amino acid sequence represented by GPLGVRG (SEQ ID NO: 5), GPQGIAG (SEQ ID NO: 6), GPLGLWARG (SEQ ID NO: 8) or GPLGIAG (SEQ ID NO 7). Most preferably, it may be an amino acid chain represented by an amino acid sequence of SEQ ID NOs: 5 to 8.

In the fusion peptide comprising a) a dhFas-1 domain which is the fourth fas-1 domain of βig-h3 lacking H1 and H2 regions ; b) a MMP(Matrix metalloproteinase) substrate; and c) a peptide comprising RGD motif (hereinafter, referred to as 'dhFas-1-MMP substrate-RGD structural peptide', and also, a fusion peptide having sequential links of mdhFas-1, MMP2 substrate, and a peptide comprising RGD motif: MFK23; 'dhFas-1-MMP substrate-RGD structural peptide', and also, a fusion peptide having sequential links of mdhFas-1, MMPI substrate, and a peptide comprising RGD motif: MFK24; a fusion peptide having sequential links of mdhFas-1, MMP3 substrate, and a peptide comprising RGD motif: MFK27; a fusion peptide having sequential links of mdhFas-1, MMP consensus substrate, and a peptide comprising RGD motif: MFK25; a fusion peptide having sequential links of hsdhFas-1, MMPI substrate, and a peptide comprising RGD motif: hsFJ24; a fusion peptide having sequential links of hsdhFas-1, MMP3 substrate, and a peptide comprising RGD motif: hsFJ27; a fusion peptide having sequential links of hsdhFas-1, MMP consensus substrate, and a peptide comprising RGD motif: hsFJ25), preferably, the a peptide comprising RGD motif may be a an amino acid chain comprising a sequence of RGDSP (SEQ ID NO: 9) or QERGDSLA (SEQ ID NO: 10), or the MMP substrate may be an amino acid chain comprising a sequence of GPQGIAG (SEQ ID NO: 6), GPLGLWARG (SEQ ID NO: 8) or GPLGIAG (SEQ ID NO 7).

The dhFas-1-MMP substrate-RGD structural peptide of the present invention preferably may be a peptide comprising a dhFas-1 domain which is the fourth fas-1 domain of βig-h3 lacking H1 and H2 regions, MMP substrate and a linker peptide consisting of 1 to 5 amino acids between them; or a peptide comprising MMP substrate, the RGD and a linker peptide consisting of 1 to 5 amino acids between them.

The linker peptide of the present invention between the a dhFas-1 domain which is the fourth fas-1 domain of βig-h3 lacking H1 and H2 regions and MMP substrate consists of 1 to 5 amino acids. And the linker is a short peptide linking between the dhFas-1 domain the MMP substrate and preferably, but not limited thereto, it may be VD (valine-aspartic acid) or VDG (valine-aspartic acid-glycine).

In addition, the linker peptide of the present invention between MMP substrate and a peptide comprising RGD motifs, consists of 1 to 5 amino acids. And the linker is a short peptide linking between the MMP substrate and the peptide comprising RGD motifs and preferably, but not limited thereto, it may be LE (leucine-glutamic acid) or EF (leucine-phenylalanine).

The dhFas-1-MMP substrate RGD structural peptide of the present invention may more preferably be the RGD peptide consisting of an amino acid sequence represented by RGDSP (SEQ ID NO: 9) or QERGDSLA (SEQ ID NO: 10), or the MMP substrate consisting of an amino acid sequence represented by GPLGVRG (SEQ ID NO: 5), GPQGIAG (SEQ ID NO: 6), GPLGLWARG (SEQ ID NO: 8) or GPLGIAG (SEQ ID NO: 7). Most preferably, it may be a peptide having an amino acid sequence represented by SEQ ID NOs: 11 to 17.

A dhFas-1-MMP substrate-RGD structural peptide of the present invention may be a functional equivalent to a fusion peptide comprising a dhFas-1; an MMP substrate; and a peptide comprising RGD motif and preferably it comprises a peptide having amino acid sequences of SEQ ID NO: 11 to SEQ ID NO:17 and its functional equivalent. The term "functional equivalent" refer to peptides which have at least 60%, preferably 70%, more preferably 80% and most preferably 90% amino acid sequence homology with the dhFas-1-MMP substrate-RGD structural peptide, preferably amino acid sequences of SEQ ID NO: 11 to SEQ ID NO: 17 and it refers a peptide showing equivalent activities with a dhFas-1-MMP substrate-RGD structural peptide of the present invention preferably having amino acid sequences of SEQ ID NO: 11 to 17. The term "substantial equivalent physiological activities" refer to the activities of preventing and inhibiting rheumatoid arthritis. The said functional equivalents may comprise, for example, dhFas-1-MMP substrate-RGD structural peptide, preferably amino acid sequence variants produced by as a result of addition, substitution or deletion of amino acid sequence of the peptides having amino acid sequence of SEQ ID NO: 11 to 17. Preferably, the substitution of amino acid is conservative substitution. Examples of conservative substitution of naturally existing amino acids may be substitution of amino acid of each amino acid groups of aliphatic amino acids group (Gly, Ala, Pro), hydrophobic amino acids group (Ile, Leu, Val), aromatic amino acids group (Phe, Tyr, Trp), acidic amino acids group (Asp, Glu), basic amino acids group (His, Lys, Arg, Gln, Asn) and sulfur containing amino acids group within the same amino acids group. Deletion of amino acids preferably refers to deletion of dhFas-1-MMP substrate-RGD structural peptide of the present invention, more preferably deletion of amino acid region which is not related to activities of the peptide having amino acid sequence of SEQ ID NO: 11 to 17. Addition of amino acid refers to addition of amino acid within the range that does not effect on activities of peptides comprising histidine tag for peptide purification or restriction enzyme sites for genetic engineering.

In addition, the range of functional equivalents comprises the peptide derivatives modified their partial chemical structure of dhFas-1-MMP substrate-RGD structural peptide of the present invention, preferably the peptide having amino acid sequence of SEQ ID NO: 11 to 17 while maintaining the back bone and the physiological activities thereof. For example, it may comprise fusion proteins which is manufactured by fusion of other protein such as GFP while maintaining structural change for changing the stability, preservability, volatility or solubility peptide of the present invention and the physiological activities thereof.

The gene for producing the peptide of the present invention may be isolated from genomic DNA of any origins or cDNA libraries and preferably it may be isolated from genomic DNA or cDNA of human or mouse. General method for producing the gene encoding the peptide of the present invention is describe well in the art (Sambrook, Fitsch & Manatis, Molecular Cloning: A Laboratory Manual, Second Edition (1989)). In addition, any animal cell could be provided as a source of amino acid for molecular cloning of the gene encoding the peptide of the present invention. DNA could be obtained from cloned DNA by skills well known in the art and it may be obtained from cDNA library prepared from cells expressing protein highly preferably by the method of chemical synthesis or cDMA cloning or cloning of genomic DNA or fragments thereof or cloning of isolated fragment of certain cells (Sambrook et al., 1989, supra: Glover, D. M. (ed). 1985, DNA Cloning; A practical Approach. MRL Press. Ltd., Oxford. U.K. Vol. I, II). Cloned gene from genomic DNA comprises regulatory region and intron region as well as encoding region.

The peptides of the present invention may be prepared by skilled person in the art with the method well known in the art. These peptides usually express a polynucleotide encoding the peptide sequence of the present invention as a part of larger polypeptide and can be prepared in prokaryotic cells or eukaryotic cells. As other methods, these peptides may be prepared by chemical synthesis. Expression of xenoproteins in recombinant hosts, chemical synthesis of polypeptides and a method of transcription in test tube are well known in the art and they are well described in the followed references: Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11:255; Kaiser et al. (1989) Ann. Rev. Biochem. 57:957; and Offord, R. E. (1980) Semisynthetic Proteins, Wiley Publishing.

Meanwhile, the present invention provides a polynucleotide encoding a dhFas-1-MMP substrate-RGD structural peptide comprising a) a dhFas-1 domain; b) a MMP (Matrix metalloproteinase) substrate, and an MMP consensus substrate; and c) a peptide comprising RGD motif.

The polynucleotide may be not limited as long as a polynucleotide encodes the dhFas-1-MMP substrate-RGD structural peptide of the present invention and comprise DNA, cDAN and RNA. Preferably, the RGD structure may be a peptide consisting of an amino acid sequence comprising RGDSP (SEQ ID NO: 9) or QERGDSLA (SEQ ID NO: 10) and more preferably, it may be a peptide consisting of an amino acid sequence consisting RGDSP (SEQ ID NO: 9) or QERGDSLA (SEQ ID NO: 10). The MMP1 substrate is, but not limited thereto, a MMP substrate which is cleaved by MMP-1, the MMP2 substrate is a MMP substrate which is cleaved by MMP-2, the MMP3 substrate is a MMP substrate which is cleaved by MMP-3, the MMPI substrate is a MMP substrate which is cleaved by MMP-7, the MMP8 substrate is a MMP substrate which is cleaved by MMP-8, the MMP9 substrate is a MMP substrate which is cleaved by MMP-9, the MMP12 substrate is a MMP substrate which is cleaved by MMP-12, the MMP13 substrate is a MMP substrate which is cleaved by MMP-13 and MMP consensus substrate is a MMP substrate which is cleaved by MMP1, 2 and 3.

In the present invention, as the MMPI substrate, the MMP3 substrate, or the MMP consensus substrate, any amino acid chain may be used as long as it exists between the dhFas-1 and an amino acid chain containing RGD capable of blocking integrin, and increases the adhesion efficiency of the dhFas-1 and the peptide comprising RGD motif by being degraded at the starting point of the progress of inflammation. Preferably, it may include an amino acid sequence represented by LGVR (SEQ ID NO: 69), QGIA (SEQ ID NO: 70), LGLW (SEQ ID NO: 71) or LGIA (SEQ ID NO: 72). More preferably, it may include an amino acid sequence represented by GPLGVRG (SEQ ID NO: 5), GPQGIAG (SEQ ID NO: 6), GPLGLWARG (SEQ ID NO: 8) or GPLGIAG (SEQ ID NO: 7).

Most preferably, the polynucleotide may include a base sequence represented by SEQ ID NOs: 18 to 24.

The polynucleotide may be separated from natural sources or may be prepared by a genetic engineering method known in the art.

Meanwhile, the present invention provides a vector including a promoter and a polynucleotide operably linked to the promoter, wherein the polynucleotide encodes a peptide (dhFas-1-MMP substrate-RGD structural peptide) comprising a) a dhFas-1 domain; b) a MMP (Matrix metalloproteinase) substrate selected from the group consisting of an MMP1 substrate, an MMP3 substrate, and an MMP consensus substrate; and c) a peptide comprising RGD motif.

In the present invention, "vector" refers to a DNA construct containing a DNA sequence which is operably linked to a suitable control sequence capable of effecting the expression of the DNA in a suitable host. The vector may be a plasmid, a phage particle or simply a potential genomic insert. Once transformed into a suitable host, the vector may replicate and function independently of the host genome, or may in some cases, integrate into the genome itself. In the present specification, "plasmid" and "vector" are sometimes used interchangeably as the plasmid is the most commonly used form of vector at present. For the purpose of the present invention, a plasmid vector is preferably used. A typical plasmid vector used for the purpose has a structure including: (a) a replication origin for effective replication to have several hundreds of plasmid vectors in one host cell; (b) an antibiotic-resistance gene for selecting a host cell transformed with the plasmid vector; and (c) a restriction enzyme cleavage site into which a foreign DNA fragment is capable of being inserted. Although there is no suitable restriction enzyme cleavage site, the vector may be easily ligated with a foreign DNA using a synthetic oligonucleotide adaptor or a linker according to a conventional method.

The "promoter" means a DNA sequence regulating the expression of nucleic acid sequence operably linked to the promoter in a specific host cell, and the term "operably linked" means that one nucleic acid fragment is linked to other nucleic acid fragment so that the function or expression thereof is affected by the other nucleic acid fragment. Additionally, the promoter may include a operator sequence for controlling transcription, a sequence encoding a suitable mRNA ribosome-binding site, and sequences controlling the termination transcription and translation. As a promoter, it may be constitutive promoter which constitutively induces the expression of a target gene, or inducible promoter which induces the expression of a target gene at a specific site and a specific time.

Examples of the vector of the present invention include a plasmid vector, a cosmid vector, a bacteriophage vector and a viral vector, but are not limited thereto. The preferred expression vector includes regulatory elements for gene expression such as a promoter, operator, an initiation codon, a stop codon, a polyadenylation signal, and an enhancer, and a variety of vectors can be prepared according to the purpose. A vector of the present invention is a method for delivering nucleic acid encoding the peptide of the present invention into host cells and the preferable viral vectors are viral vectors such as retrovirus, herpes virus, adenovirus, and adenovirus related virus. Accordingly, the gene encoding the peptide of the present invention is introduced in vivo, ex vivo and in vitro by using viral vectors or direct introduction of DNA. The expression in the target tissue may be performed by targeting a mutant vector to specific cells using viral vector or receptor ligand or by using tissue-specific promoter or both.

For DNA viral vector, it may comprise attenuated or defective DNA virus, for example, but not limited thereto, herpes simplex virus, papilloma virus, Epstein-Bar virus, adeno virus, adeno-associated virus, vaccinia virus. Preferably, it may be defective virus which is deleted all or most of viral genes. Because the defective virus does not have replication ability, it cannot induce viral infection when it is introduced into a cell. Accordingly, if the defective viral vector is used, it may be administered without worry about it may infect other cells. Therefore, a certain tissue can be targeted.

Meanwhile, standard recombinant DNA and molecular cloning technique used in the present invention are well known in the art and disclosed the reference as follows: (Sambrook, J., Fritsch, E. F. and Maniatis, T., Molecular Cloning: A Laboratory Manual, 2nd ed., Cold Spring Harbor Laboratory: Cold Spring Harbor, N.Y. (1989); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience (1987)).

Meanwhile, the present invention provides a host cell transformed by a vector of the present invention.

The host cell may be selected from those regulate expression of inserted sequence or progress preferred genetic procedures. Different host cell has specific mechanism regarding translation of proteins and post-translational processing and modifications. For appropriated cell lines or host cell system, it may be selected from those produce preferable modification and processing of xenoproteins. Expression in the yeast can produce biologically active products. Expression in eukaryotic cells may increase possibility of "natural" folding.

Any host cell well known in the art can be used as ling as it can clone and express a vector of the present invention with stable and continous and for example, *E. coli* JM109, *E. coli* BL21DE, *E. coli* DH5a, *E. coli* RR1, *E. coli* LE392, *E. coli* B, *E. coli* X 1776, *E. coli* W3110 can be used. In addition, agrobacteria such as agrobacteria A4, bacilli such as *bacillus subtilis*, enterobacteria such as *Salmonella typhimurium* or *Serratia marcescens* and various *Pseudomonas* species can be used.

In addition, in case of transforming eukaryotic cell with a vector of the present invention, for host cells, yeast (*saccharomyces cerevisiae*), insect cells and human cells (e.g. CHO cell line (Chinese hamster ovary), W138, BHK, COS-7, 293, HepG2, 3T3, RIN and MDCK cell line) may be used.

A host cell of the present invention preferably may be *E. coli*.

Any method for transforming a host cell by introducing a vector into the host cell may be used and not limited. For example, the transformation may be performed by calcium phosphate precipitation, DEAE-dextran method, electroporation, direct microinjection, DNA loaded liposome, liofectamine-DNA complex, cell sonication, gene bombardment using high velocity microprojectile, polycation and receptor-mediated transfection. Some of these technologies may be modified for use in vivo or in vitro.

The vector introduced into a host cell can be expressed and in this case large quantity of recombinant peptide or protein can be obtained. For example, in case that a vector comprise lac promoter, the gene expression may be induced by treating IPTG with the host cell.

In the method of the present invention, the culturing of a transformed host cell may be carried out by using a culture medium conventionally used in the art. For example, when a transformant is a procaryotic cell (e.g., *E. coli*), the transformant may be cultured by using LB (Luria-Bertani) culture medium. When a transformant is an animal cell, for example, the transformant may be cultured by using Eagles's MEM (Eagle's minimum essential medium, Eagle, H. Science 130:432 (1959)).

Various culturing methods of a transformant are well known to the person skilled in the art, and disclosed in Sambrook et al., Molecular Cloning, A Laboratory Manual, Cold Spring Harbor Laboratory Press (2001), which is incorporated into the present disclosure by reference.

The fusion peptide of the present invention has an effect on inflammatory disease. The inflammatory disease of the invention may include, but are not limited to, common inflammatory symptoms such as edema, inflammatory bowel disease, peritonitis, osteomyelitis, cellulitis, pancreatitis, trauma causing shock, bronchial asthma, allergic rhinitis, cystic fibrosis, acute bronchitis, chronic bronchitis, acute bronchiolitis, chronic bronchiolitis, osteoarthritis, gout, spondyloarthropathy, ankylosing spondylitis, Reiter's syndrome, psoriatic arthropathy, spondylitis associated with inflammatory bowel disease, juvenile arthropathy, juvenile ankylosing spondylitis, reactive arthropathy, infectious arthritis, post-infectious arthritis, gonococcal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Wegener's granulomatosis, polymyalgia rheumatica, giant cell arteritis, calcium crystal deposition arthropathris, pseudo gout, non-articular rheumatism, bursitis, tenosynomitis, epicondylitis (tennis elbow), neuropathic joint disease, hemarthrosis (hemarthrosic), Henoch-Schonlein Purpura, multicentric reticulohistiocytosis, hemoglobinopathy, familial Mediterranean fever, Behcet's disease, systemic lupus erythematosus, multiple sclerosis, septicemia, septic shock, acute respiratory distress syndrome, multiple organ failure, chronic obstructive pulmonary disease, rheumatoid arthritis, acute lung injury. Also, examples of the inflammatory disease include inflammatory skin diseases, such as acute and chronic eczema, atopic dermatitis, contact dermatitis, dermatitis seborrheica, dermatitis exfoliativa, solar dermatitis and psoriasis. Preferably, the inflammatory disease of the invention may be rheumatoid arthritis.

The characteristic of the composition of the present invention is described through Examples.

In one embodiment of the present invention, the mdhFas-1-MMP substrate-RGD structural peptides (MKF23, MFK24, and MFK25), mdhFas-1, and hsdhFas-1 and mdhFas-1-RGD structural peptides (MFK12) were prepared, and an inhibition effect on adhesion and migration of a synovial membrane cell was measured.

As a result, it was found that MFK23, MFK24 and MFK25 showed a significantly high inhibiting effect on cell adhesion and migration as compared to a conventional YH18 motif, mdhFas-1, and the mdhFas-1 structure modified peptide. Also, when mdhFas-1 and RGDSP (SEQ ID NO: 9), alone or in combination, were used in the same cell adhesion test, it was found that MFK24 showed the highest cell adhesion inhibiting effect compared to mdhFas-1 and RGDSP (SEQ ID NO: 9) (see Example 3, and Comparative Examples 1 and 2).

In another embodiment of the present invention, in a collagen-induced arthritis (CIA) mouse model, it was found that the peptide of the present invention shows an arthritis therapeutic effect.

The peptide of the present invention was administered for a predetermined period while an arthritis index was measured and was compared to a control group. As a result, it was found that the peptide of the present invention including an MMP1 substrate decomposed by MMP-1 showed a high arthritis inhibiting effect even in a group administered in a dose of 0.1 mg/kg and the effect was maintained, while a control group administered with mdhFas-1 or MFK12 in a dose of 30 mg/kg showed an arthritis inhibiting effect.

Also, when a foot tissue of the experimental mouse was examined, it was observed that in the group administered with the peptide of the present invention, even in a group administered in a dose of 0.1 mg/kg, the proliferation of a synovial membrane cell was inhibited and the deformation of cartilage and bones was reduced. Also, when the amount of inflammatory mediators was measured, it was found that the group administered with the peptide of the present invention (even the group administered in a dose of 0.1 mg/kg) effectively inhibited inflammatory mediators.

In a case of MFK12, in the group administered in a dose of 10 mg/kg, it was observed that the articulation region was destroyed, and a synovial membrane cell was hyper-proliferated, and it was found that the vascularization induction and the cell adhesion protein expression were increased as much as that in the control group. Meanwhile, the group administered in a dose of 30 mg/kg showed a therapeutic effect to some extent. Also, through the measurement of inflammatory mediators, it was found that there is no significant difference in an inflammatory mediators expression level between the group administered with MFK12 in a dose of 10 mg/kg and the control group, while the group administered in a dose of 30 mg/kg showed a reduced expression level (see Example 4, and Comparative Examples 3 and 4).

Accordingly, it was determined that the peptide of the present invention has a very high arthritis therapeutic effect, which is 100 times or more as high as a conventional peptide.

Accordingly, it was determined that the dhFas-1-MMP-substrate-RGD structural peptide of the present invention, even in a very low dose, shows a high effect on rheumatoid arthritis compared to dhFas-1 and MFK12.

Accordingly, the present invention provides a pharmaceutical composition for preventing and treating inflammatory disease comprising the dhFas-1-MMP substrate-RGD structural peptide as an active ingredient.

The composition of the present invention includes, as an active ingredient, a fusion peptide, comprising a) a dhFas-1 domain which is the fourth fas-1 domain of βig-h3 lacking H1 and H2 regions; b) a MMP (Matrix metalloproteinase) substrate, and an MMP consensus substrate; and c) a peptide comprising RGD motif.

MMP substrate of the present invention refers to a short peptide degraded by MMP, but not limited thereto, specifically, MMP-1 substrate, MMP-2 substrate, MMP-3 substrate, MMP-7 substrate, MMP-8 substrate, MMP-9 substrate, MMP-12 substrate, MMP-13 substrate and MMP consensus substrate. In the present invention, the MMP substrate may be preferably an amino acid chain comprising an amino acid sequence represented by LGVR (SEQ ID NO: 69), QGIA (SEQ ID NO: 70), LGLW (SEQ ID NO: 71) or LGIA (SEQ ID NO: 72). More preferably, it may be an amino acid chain comprising an amino acid sequence represented by GPLGVRG (SEQ ID NO: 5), GPQGIAG (SEQ ID NO: 6), GPLGLWARG (SEQ ID NO: 8) or GPLGIAG (SEQ ID NO: 7).

In the pharmaceutical composition of the present invention for preventing and treating inflammatory disease, the amino acid chain comprising RGD may be an amino acid chain comprising an amino acid sequence represented by RGDSP (SEQ ID NO: 9) or QERGDSLA (SEQ ID NO: 10). More preferably, the peptide may have an amino acid sequence represented by a SEQ ID NOs: 11 to 17, and comprise its functional equivalent. When the dhFas-1-MMP substrate-RGD structural peptide of the present invention is used, it is possible to show higher efficacy even in a low dose, compared to that in dhFas-1. Also, since its fragment is relatively short, proteins do not clump together. Thus, in its formulation process, the regulation is further easy, and also it is advantageous in view of drug delivery.

Also, through in vivo expression inflammatory disease of a vector including polynucleotide encoding the dhFas-1-MMPsubstrate-RGD structural peptide, it is possible to produce a material effective in prevention and treatment. Thus, the present invention provides a pharmaceutical composition for preventing and treating inflammatory disease, which comprise a vector comprising polynucleotide encoding the dhFas-1-MMPsubstrate-RGD structural peptide as an active ingredient.

The applicable disease for the composition of the present invention is inflammatory disease, preferably, rheumatoid arthritis.

A pharmaceutical composition of the present invention may comprise dhFas-1-MMP substrate-RGD structural peptide, or a vector comprising a polynucleotide encoding the dhFas-1-MMP substrate-RGD structural peptide alone or together with one or more pharmaceutically acceptable carrier additionally.

A pharmaceutically acceptable carrier, for example, carriers for the parenteral or oral preparations may be included. The carriers for the oral preparations may comprise lactose, starch, cellulose derivatives, magnesium stearate, stearic acid. In addition, they may comprise various drug delivery materials for oral administration of peptide agents. In addition, the carriers for the parenteral preparations may comprise water, oil, saline, aqueous glucose and glycol, and stabilizers and preservatives. The examples of the stabilizers may be antioxidant such as sodium hydrogen sulfite, sodium sulfite, and ascorbic acid. The examples of the preservatives may be benzalkonium chloride, methyl- or propyl-paraben, and chlorobutanol. The list of pharmaceutically acceptable carriers are disclosed in Remington's Pharmaceutical Sciences, 19th ed., Mack Publishing Company, Easton, Pa., 1995.

As used herein, the term "effective amount" refers to an amount showing a treating effect against the relevant disease in a subject and the "subject" refers to a mammal and, preferably, it refers to mammals comprising human. The subject may be a patient who needs treatment of disease.

A pharmaceutical composition of the present invention may be administered by various routes to mammals comprising human. For parenteral administration, but not limited thereto, it may be administered by intravenous, intramuscular, intraarterial, intramarrow, subdural, intracardiac, intracutaneous, subcutaneous, intraperitoneal, intranasal, gastrointestinal tracts, parenteral, sublingual or rectum.

A pharmaceutical composition of the present invention may be formulated into oral preparations or parenteral preparations according to the administration routes as mentioned above.

In case of the formulation for oral administration, the composition of the present invention may be formulated with a proper carrier for oral administration into powders, granules, tablets, pills, and sugar-coated tablets, capsules, liquids, gels, syrups, slurries, and emulsions by using the method known in the art. For example, an oral preparation of tablets of sugar-coated tablets may be obtained by mixing an active ingredient with solid excipient, griding, adding appropriate adjuvants and process into granular mixture. For examples of appropriate carriers, it may comprise sugars comprising lactose, dextrose, sucrose, sorbitol, mannitol, xylitol, erythritol and maltitol, starches comprising corn starch, wheat starch, rice starch and potato starch, celluloses comprising cellulose, methyl cellulose, sodium carboxymethylcellulose and hydroxypropylmethylcellulose, and fillers comprising gelatin and polyvinylpyrrolidone. And, if desired, it may comprise cross-linked polyvinylpyrrolidone, agar, alginic acid or sodium alginate as a solutionizer. Further, a pharmaceutical composition of the present invention may comprise anti-coaglutinating agent, lubricant, wetting agents, flavors, emulsifying agents and antiseptics.

For parenteral preparations, it may be prepared into injections, creams, lotions, ointments, oils, humectants, gels, aerosols and nasal inhalants according to the skills well known in the art. These preparations are disclosed in the reference of Remington's Pharmaceutical Science, 15th Edition, 1975. Mack Publishing Company, Easton, Pa. 18042, Chapter 87: Blaug, Seymour.

Total effective amount of the dhFas-1-MMP substrate-RGD structural peptide in a composition of the present invention may be administered to a patient with a single dose, or may be administered with multiple doses by fractionated treatment protocol. The pharmaceutical compositions of the present invention may contain variable amount of effective ingredient according to the administration purpose. However, preferably, it may be administered a day with amount of 0.01 ug to 1,000 mg/kg body weight/day and most preferably, 0.1 ug to 100 mg/kg body weight/day. However, the dose may be suitably determined by considering various factors, such as age, body weight, health condition, sex, disease severity, diet and excretion of a subject in need of treatment, as well as administration time and administration route. Therefore, when those are considered, skilled person in the art may determine appropriate dose of the dhFas-1-MMP substrate-RGD structural peptide for preventing or treating rheumatoid arthritis. A pharmaceutical composition of the present invention may not limit formulations, administration routes, and administration methods as long as they show the effect of the present invention.

EXAMPLES

Hereinafter, the present invention will be described in detail with reference to Examples. However, the following Examples illustrate the invention and are not intended to limit the same.

Comparative Example 1

Figure 1A:
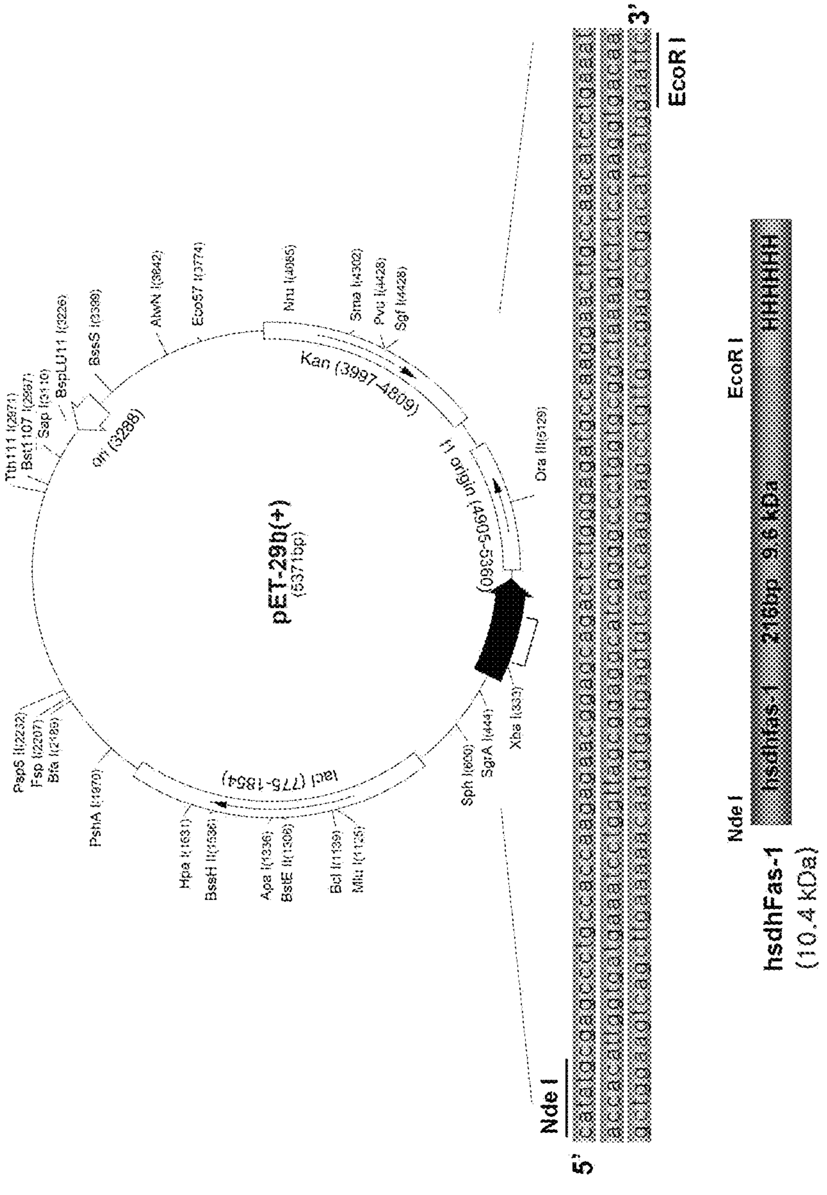
FIG. 1 is the result of immunoblot, which shows a sequence of hsdhFas-1 (structurally modified peptide of fas-1 domain of human βig-h3), and the expression of an hsdhFas-1 recombinant peptide.
Figure 1B:
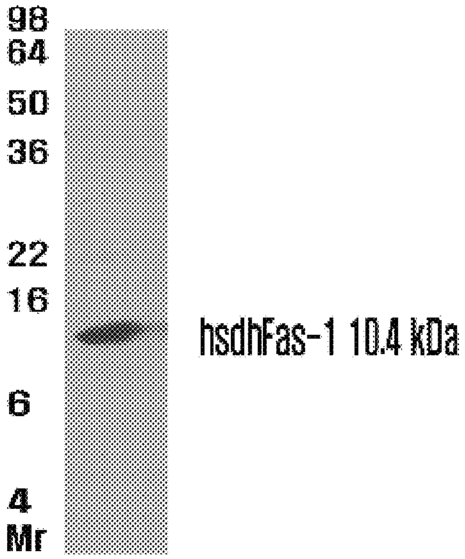

Examination of dhFas-1 Peptide's Effect on the Adhesion and Migration of a Cell A structurally modified peptide of a fas-1 domain of human βig-h3 was synthesized as a recombinant peptide (hereinafter, referred to as 'hsdhFas-1 peptide') (see FIG. 1).

Human βig-h3 was introduced into a 96-well plate at a concentration of 5 ug/ml, and coated for 14 hours at 4° C. In DMEM+0.5% BSA (Bovine Serum Albumin) culture medium, human fibroblast (NIH3T3) was introduced, and hsdhFas-1 peptide at concentrations was injected thereto, followed by mixing. The resultant mixture was cultured at 37° C. for 30 minutes, and plated on a coated well. It was cultured for 2 hours, and washed with PBS (phosphate buffered saline) so as to remove unattached cells, and then added with a substrate (4-Nitrophenyl N-acetyl-β-D-glucosaminide, Sigma, U.S.) to be activated by β-N-acetylglucosaminidase within the cell, followed by culturing at 37° C. for 1 hour. Then, a glycine EDTA solution (0.5M EDTA, 50 mM glycine, pH 10.4) was added thereto, and the coloring extent according to the number of attached cells was measured by absorbance.

Figure 3:
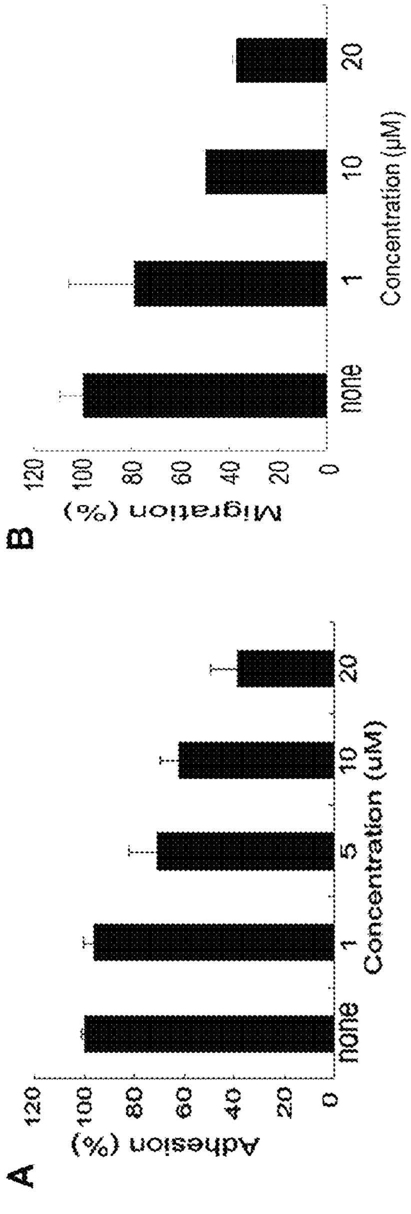
FIG. 3 is the result of immunoblot, which shows that adhesion (A) and migration (B) of βig-h3-mediated NIH3T3 cell line were concentration-dependently inhibited by hsdhFas-1 (Adhesion(%): cell adherence (relative adherence with respect to 100% of control group), Migration(%): cell migration (relative migration respect to 100% of control group), Concentration(uM): concentration of added peptide).

When the inhibiting effect by hsdhFas-1 peptide on adhesion and migration of a Synovial membrane cell was examined, it was found that as shown in FIG. 3, in a human Synovial membrane cell, the βig-h3-mediated adhesion was concentration-dependently inhibited.

Figure 2A:
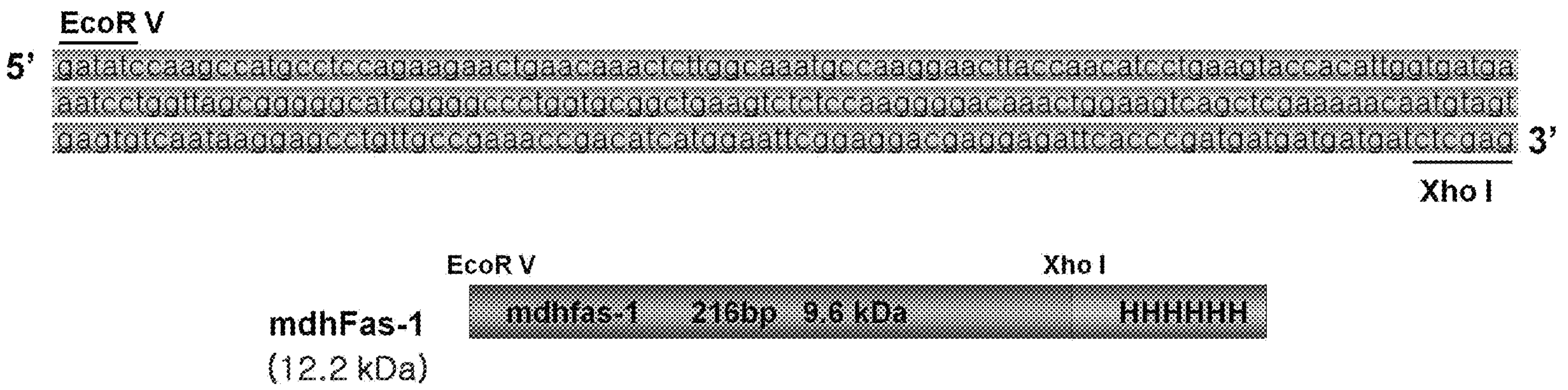
FIG. 2 is the result of immunoblot, which shows a sequence of mdhFas-1 (structurally modified peptide of fas-1 domain of mouse βig-h3), and the expression of an mdhFas-1 recombinant peptide.
Figure 2B:
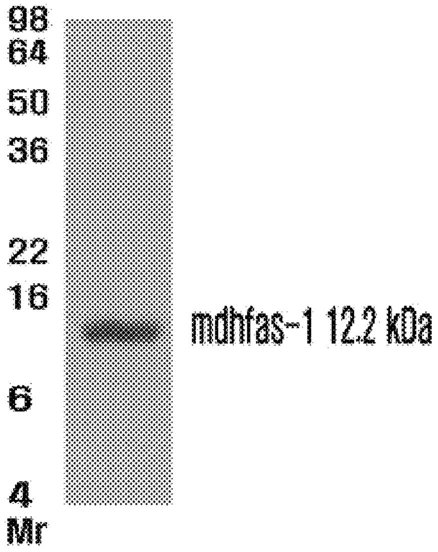

Also, a structurally modified peptide of a fas-1 domain of mouse βig-h3 was synthesized as a recombinant peptide (hereinafter, referred to as 'mdhFas-1peptide', see FIG. 2), and a mouse cell line, that is, NIH3T3 cell line, was used to test the inhibiting effect by mdhFas-1 peptide on adhesion and migration of a Synovial membrane cell in the same manner as that in the test using human βig-h3.

Figure 4:
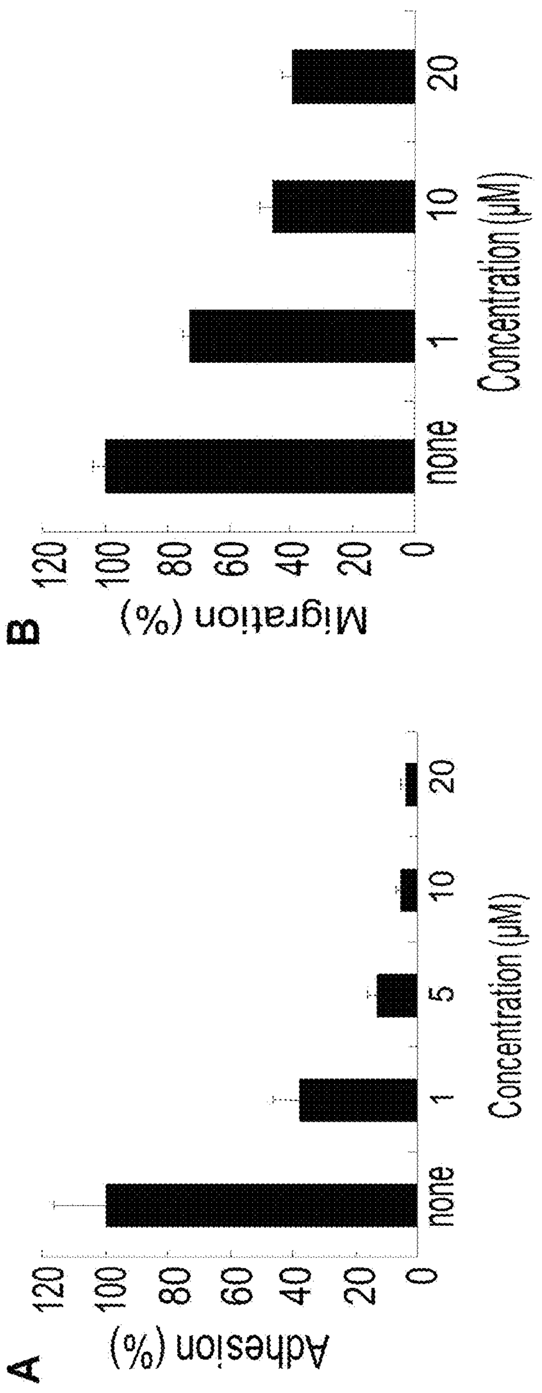
FIG. 4 is the result of immunoblot, which shows that adhesion (A) and migration (B) of βig-h3-mediated NIH3T3 cell line were concentration-dependently inhibited by mdhFas-1 (Adhesion(%): cell adherence (relative adherence with respect to 100% of control group), Migration(%): cell migration (relative migration respect to 100% of control group), Concentration(uM): concentration of added peptide).

As a result, as shown in FIG. 4, it was found that like hsdhFas-1, mdhFas-1 concentration-dependently inhibited βig-h3-mediated adhesion/migration.

Comparative Example 2

Figure 5A:
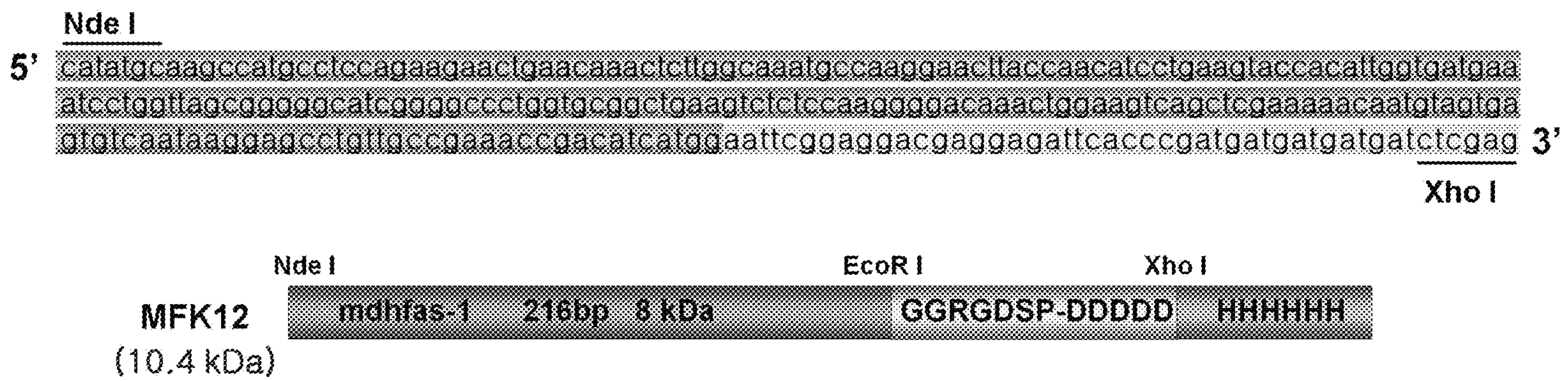
FIG. 5 is the result of immunoblot, which shows that a sequence of peptide (MFK12) including mdhFas-1 linked to an amino acid sequence RGDSP (SEQ ID NO: 9), and the expression of an MFK12 recombinant peptide.
Figure 5B:
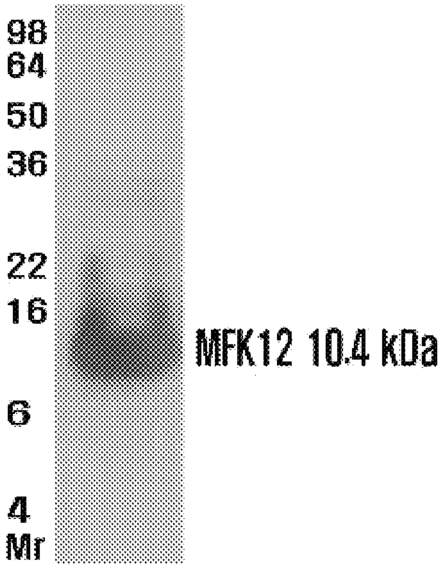

Examination of MFK12 Peptide's Effect on the Adhesion and Migration of a Cell Based on the result that in mdhFas-1 treatment concentration-dependently inhibits the activity of arthritis in a mouse CIA model, in order to design a peptide capable of showing a high therapeutic effect through low dose administration, a peptide having mdhFas-1 (as a basic structure) linked to an RGDSP (SEQ ID NO: 9) peptide was prepared (hereinafter, referred to as 'MFK12 peptide')(see FIG. 5).

The mdhFas-1-RGD structural peptide was cloned into a pET29b expression vector, and then transformed into *E. coli* BL21 (DE3), BL21(DE3)pLyss or Rosetta(DE3). The transformed *E. coli* was cultured so as to express an mdhFas-1-RGD structural peptide.

A gene, which encodes a peptide prepared by removing H1 and H2 regions from the fourth fas-1 domain of mouse βig-h3 (that is, mdhFas-1), was PCR amplified by using mouse βig-h3 (NM_009369) as a template, and primers (forward 5'-TATCATATGCAAGCCATGCC-3' (SEQ ID NO: 27), reverse 5'-TCACCGAATTCCATGATGTC-3' (SEQ ID NO: 28)). The amplified product was cloned into pET 29b expression vector by using restriction enzymes Nde I and EcoR I. Also, in the RGDSP peptide, primers (forward 5'-AATTCGGAGGACGAGGAGATTCACCCGATGATGATGATGATC-3' (SEQ ID NO: 29), reverse 5'-TCGAGATCATCATCATCATCGGGTGAATCTCCTCGTCCTCCG-3' (SEQ ID NO: 30)) were complimentarily bound to the template, and then, inserted into restriction enzymes EcoR I and Xho I on pET 29b expression vector containing dhFas-1-sequence. Then, the vector was transformed into *E. coli* BL21DE.

TABLE 1

| Primers for vector | | |
|---|---|---|
| Name of Primer | SEQ ID NO: | sequence (5'-3') |
| mdhFas-1-forward | 27 | TATCATATGCAAGCCATGCC |
| mdhFas-1-reverse | 28 | TCACCGAATTCCATGATGTC |
| RGDSP (SEQ ID NO: 9)-forward | 29 | AATTCGGAGGACGAGGAGATTCACCCGATG ATGATGATGATC |
| RGDSP (SEQ ID NO: 9)-reverse | 30 | TCGAGATCATCATCATCATCGGGTGAATCT CCTCGTCCTCCG |

A test of an MFK12 peptide's effect on the adhesion and migration of a mouse fibroblast, that is, NIH3T3 cell, was carried out in the same manner as that in Comparative Example 1.

Figure 6:
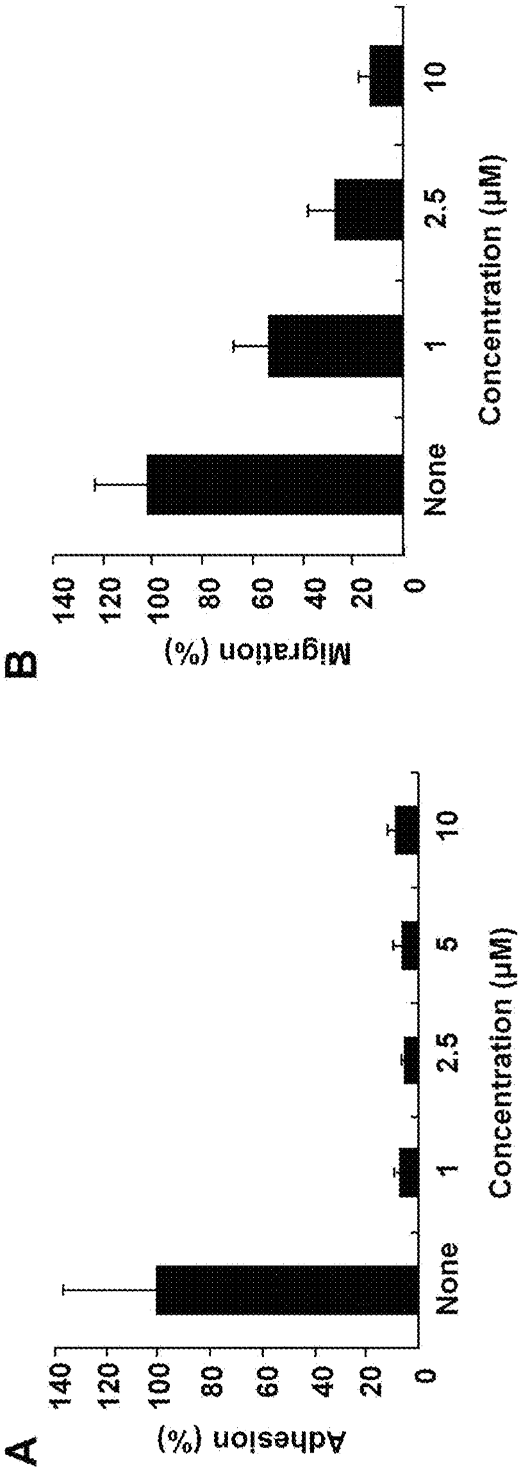
FIG. 6 is the result showing that adhesion (A) and migration (B) of βig-h3-mediated NIH3T3 cell line were concentration-dependently inhibited by MFK12 (Adhesion (%): cell adherence (relative adherence with respect to 100% of control group), Migration(%): cell migration (relative migration respect to 100% of control group), Concentration (uM): concentration of added peptide).

As a result, as shown in FIG. 6, it was found that MFK12 inhibited the adhesion and migration of a cell even at a lower concentration than that in Comparative Example 1.

Example 1

Preparation and Separation of dhFas-1-MMPsubstrate-RGD Structural Peptide

Figure 7A:
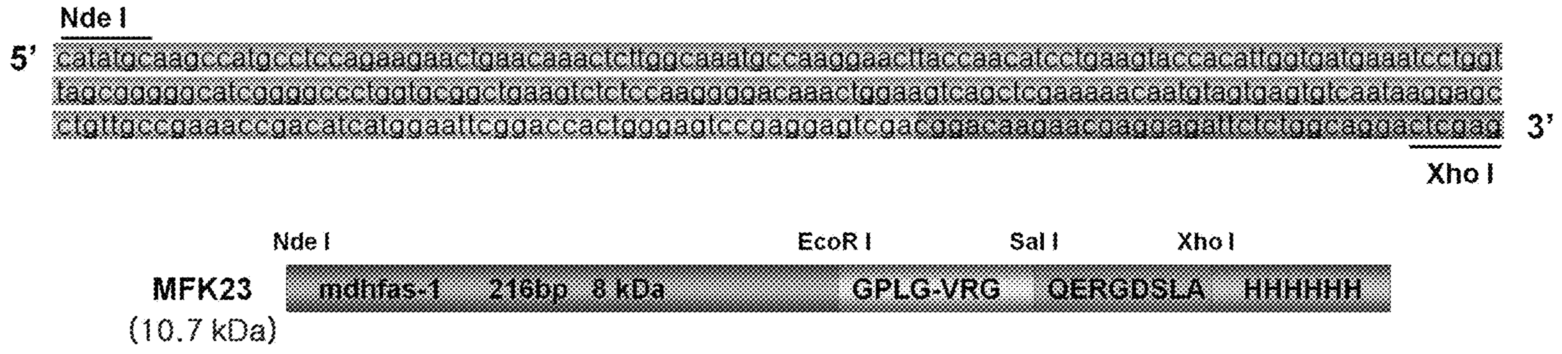
FIG. 7 is the result of immunoblot, which shows a sequence of MFK23, and the expression of MFK23 recombinant peptide.
Figure 7B:
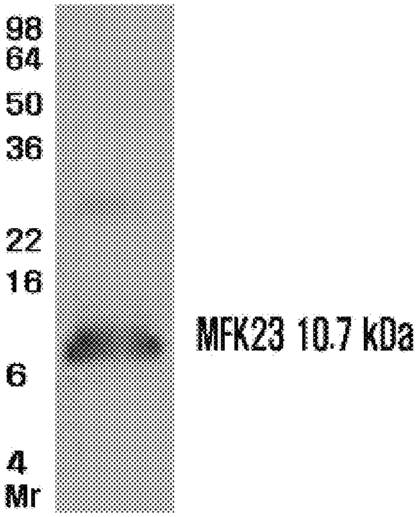
Figure 8A:
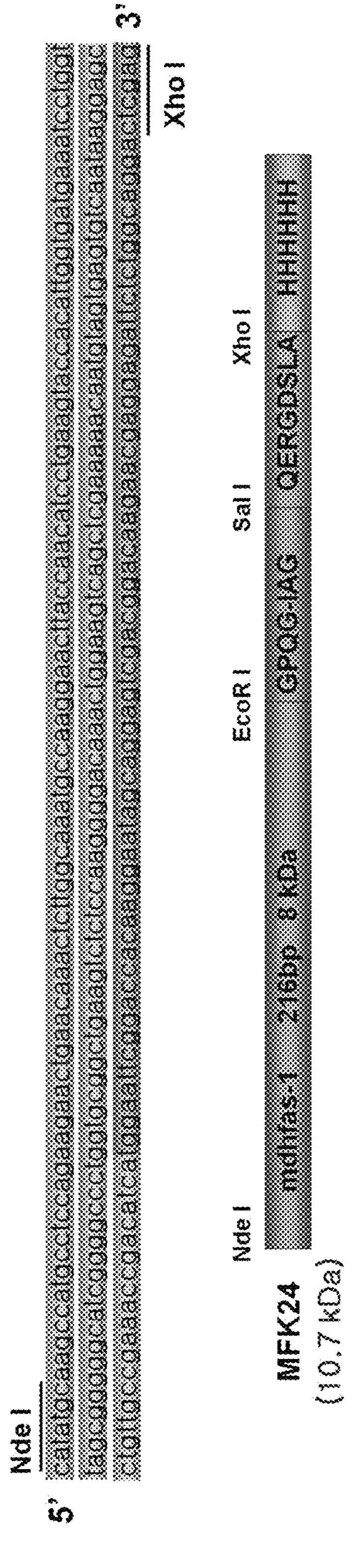
FIG. 8 is the result of immunoblot, which shows a sequence of MFK24, and the expression of MFK24 recombinant peptide.
Figure 8B:
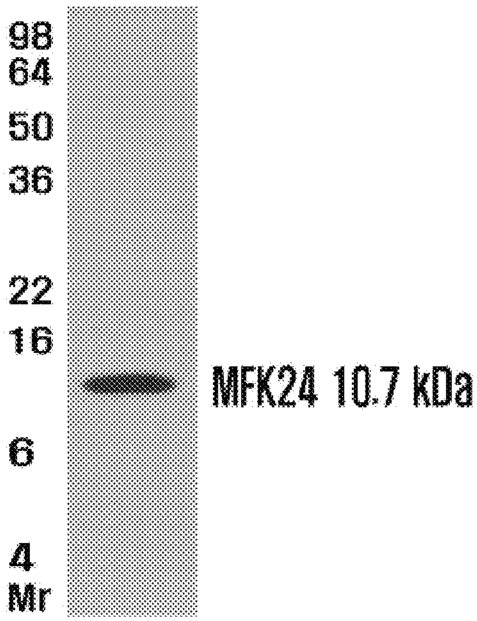
Figure 9B:
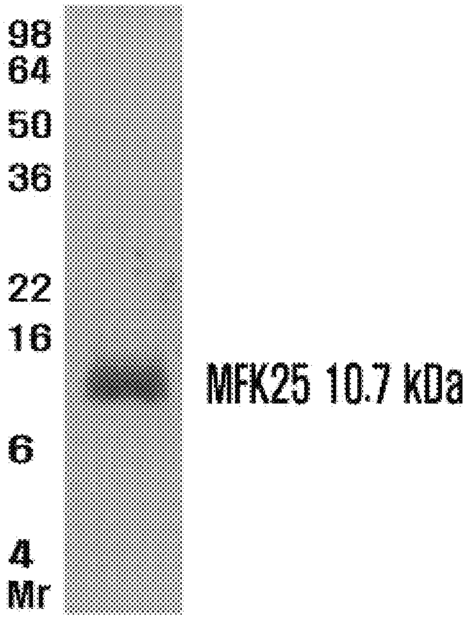
FIG. 9 is the result of immunoblot, which shows a sequence of MFK25, and the expression of MFK25 recombinant peptide.
Figure 10A:
FIG. 10 is the result of an enzymatic digestion test of MMP-1, -2, and -3 and Cathepsin K, L, and D on an MFK23 peptide having an MMP-2 substrate (MFK23(ug): an amount (ug) of administered MFK23 peptide; MMP1(ng), MMP2(ng), MMP3(ng): an amount of MMP (matrix metalloproteinase) 1, MMP2 or MMP3 used in the digestive enzyme test; Cathepsin D(ng), Cathepsin L(ng), Cathepsin K(ng): an amount of cathepsin D, L or cathepsin K used in the digestive enzyme test; Ab-histidine: an amount of a peptide bound to an anti-histidine antibody; Ab-bigh3: an amount of a peptide bound to an anti-Bigh3 antibody; normalized ratio (histidine/big-h3): an amount of histidine/ an amount of big-h3).
Figure 10B:
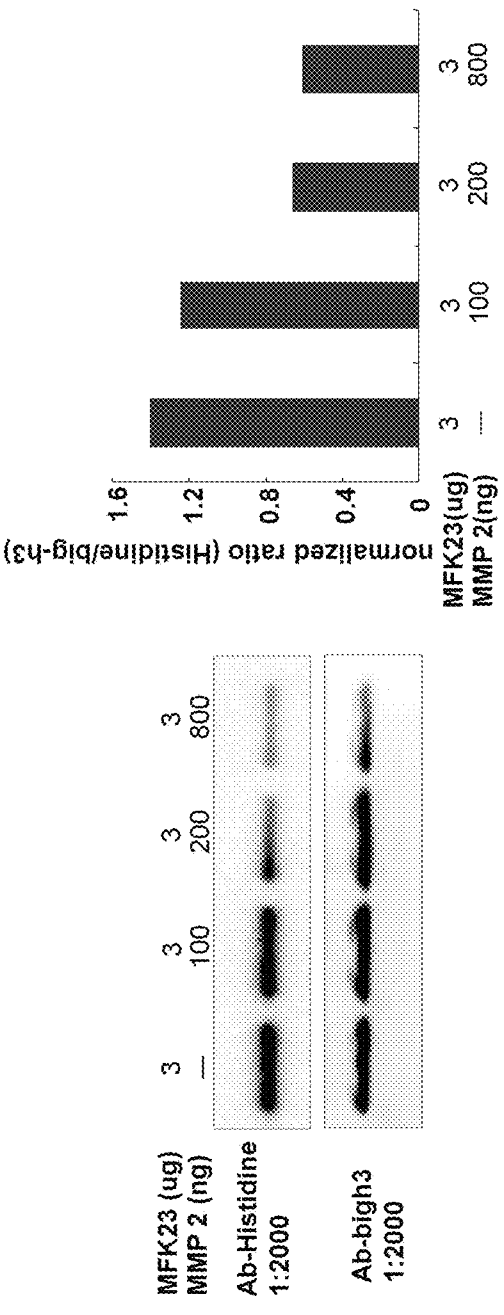
Figure 10C:
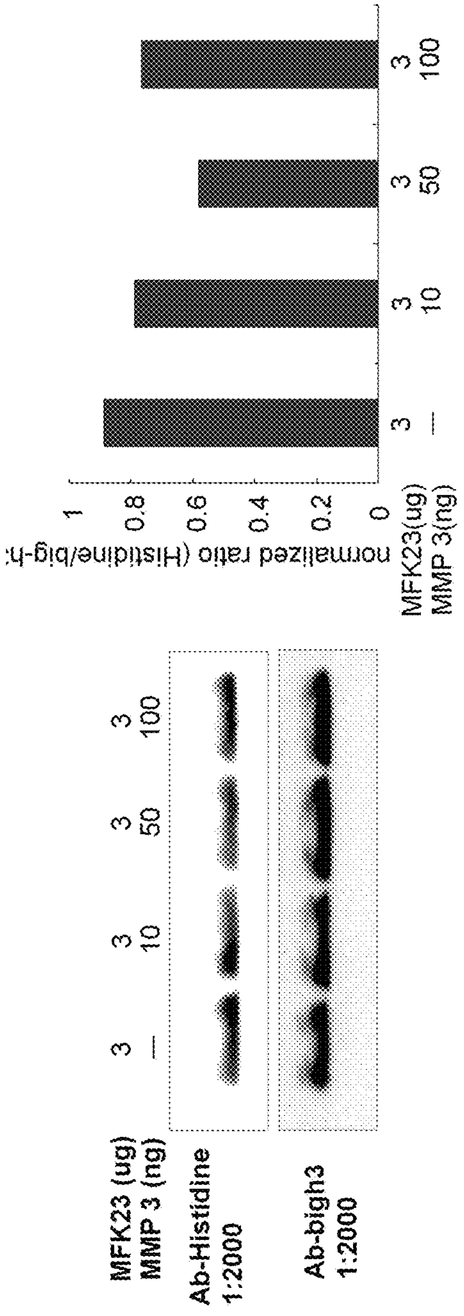
Figure 10D:
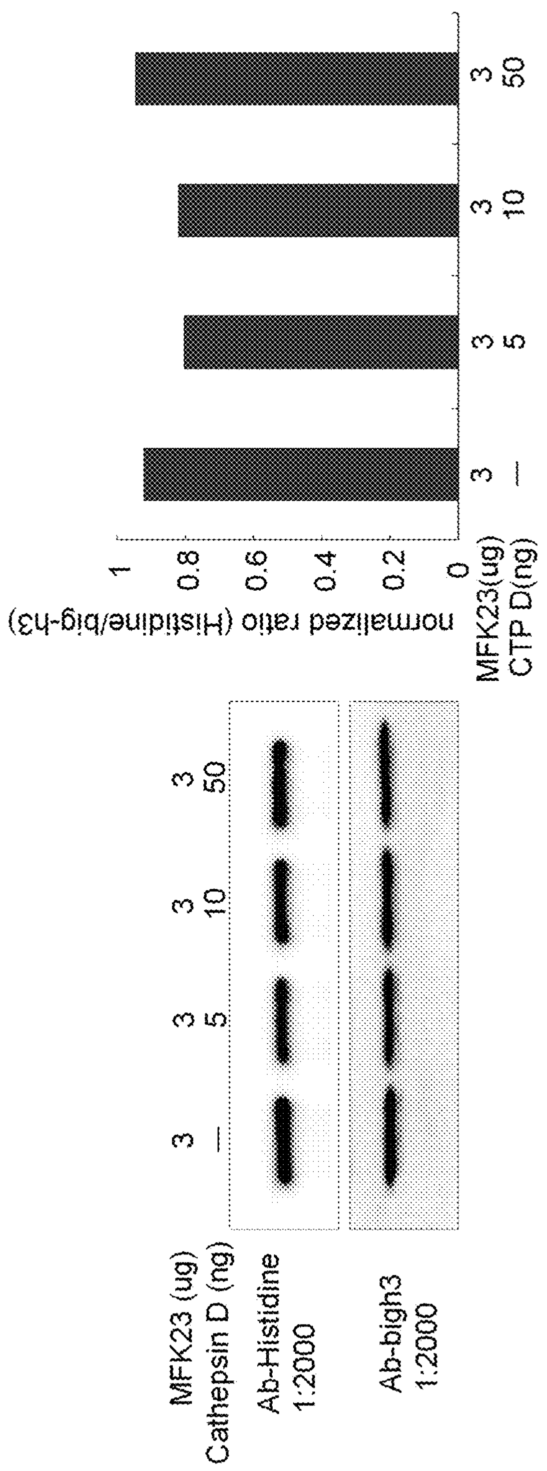
Figure 10E:
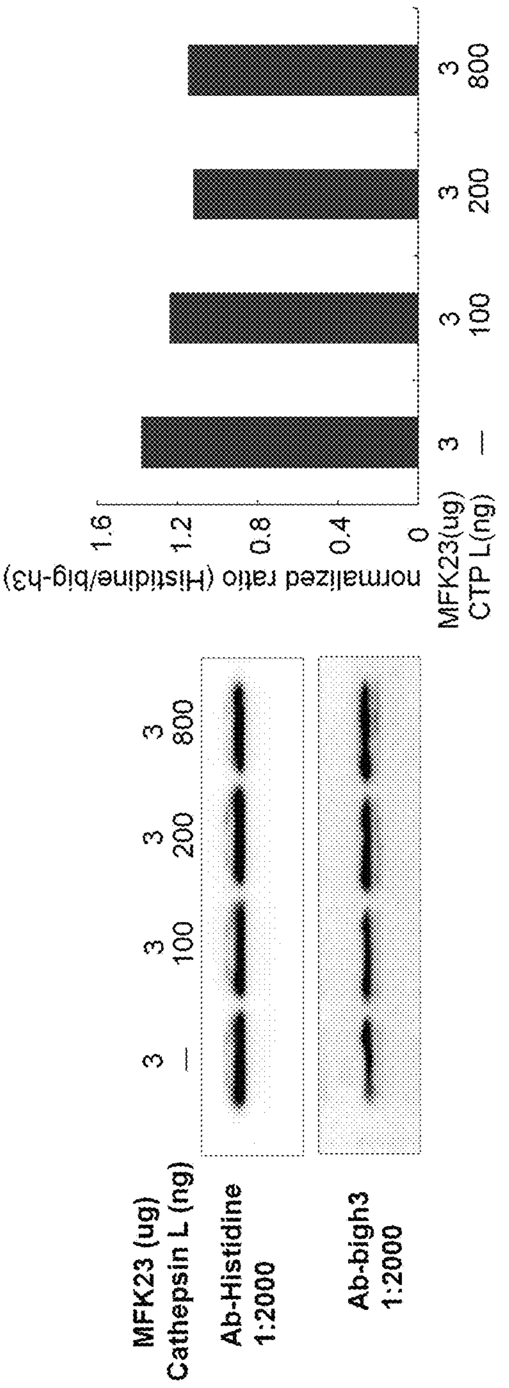
Figure 10F:
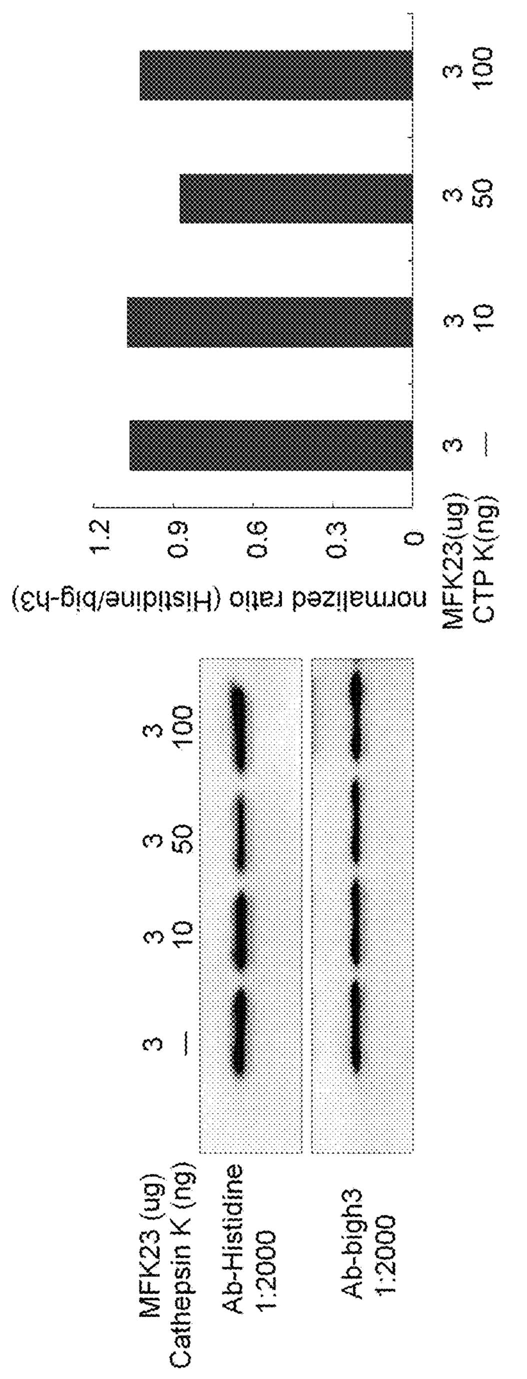
Figure 11A:
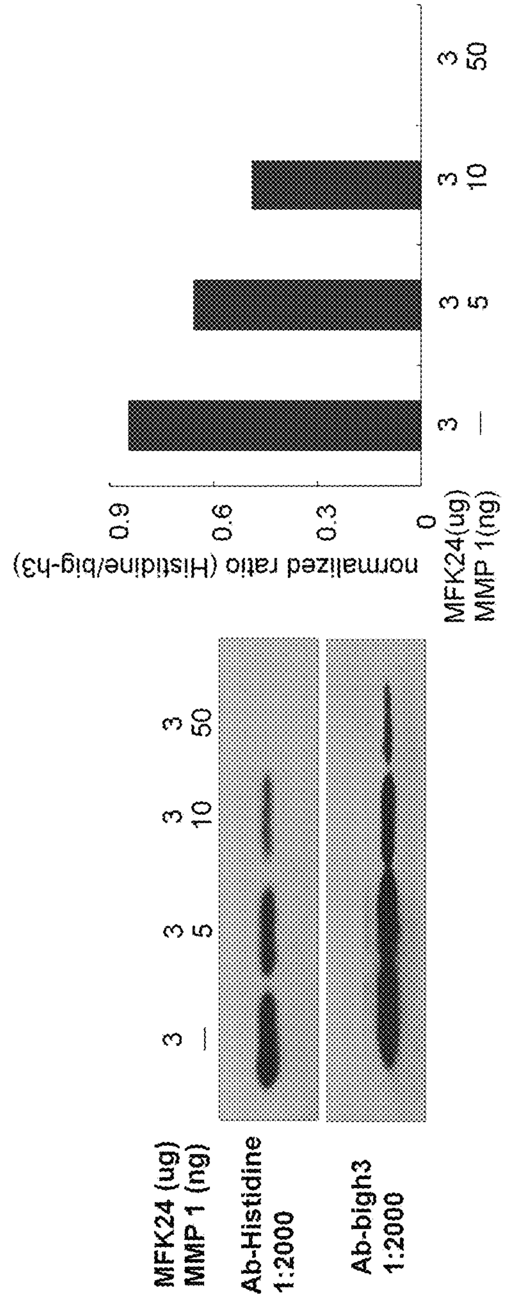
FIG. 11 is the result of an enzymatic digestion test of MMP-1, -2, and -3 and Cathepsin K, L, and D on an MFK24 peptide having an MMP-1 substrate (MFK24(ug): an amount (ug) of administered MFK24 peptide; MMP1(ng), MMP2(ng), MMP3(ng): an amount of MMP1, MMP2 or MMP3 used in the digestive enzyme test; Cathepsin D(ng), Cathepsin L(ng), Cathepsin K(ng): an amount of cathepsin D, L or cathepsin K used in the digestive enzyme test; Ab-histidine: an amount of a peptide bound to an anti-histidine antibody; Ab-bigh3: an amount of a peptide bound to an anti-Bigh3 antibody; normalized ratio (histidine/big-h3): an amount of histidine/an amount of big-h3).
Figure 11B:
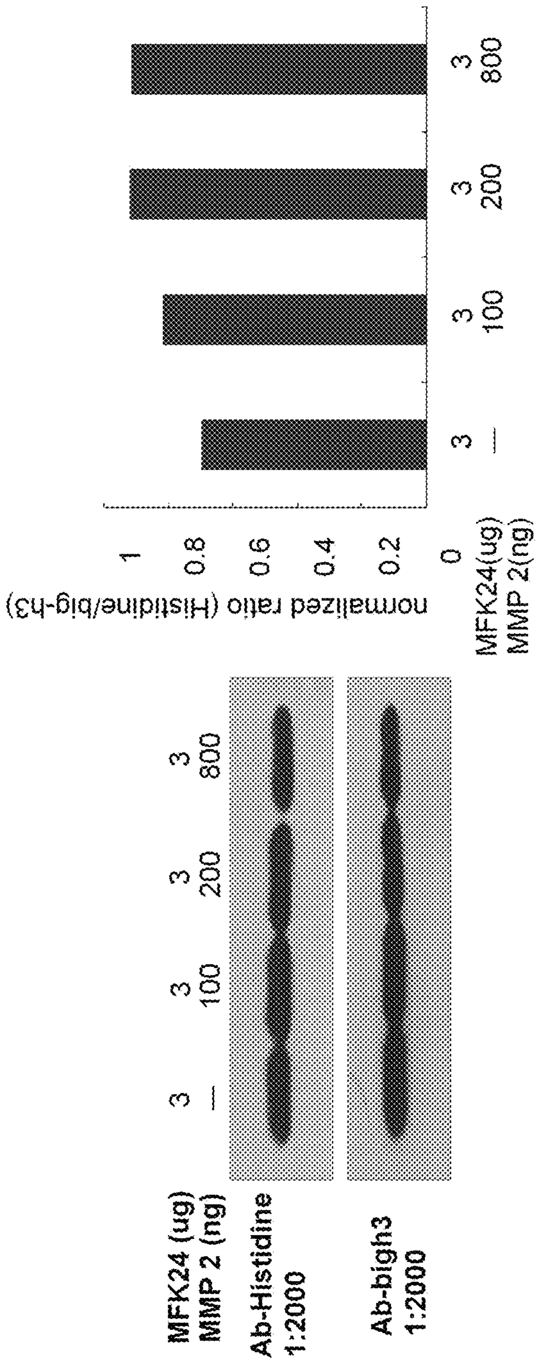
Figure 11C:
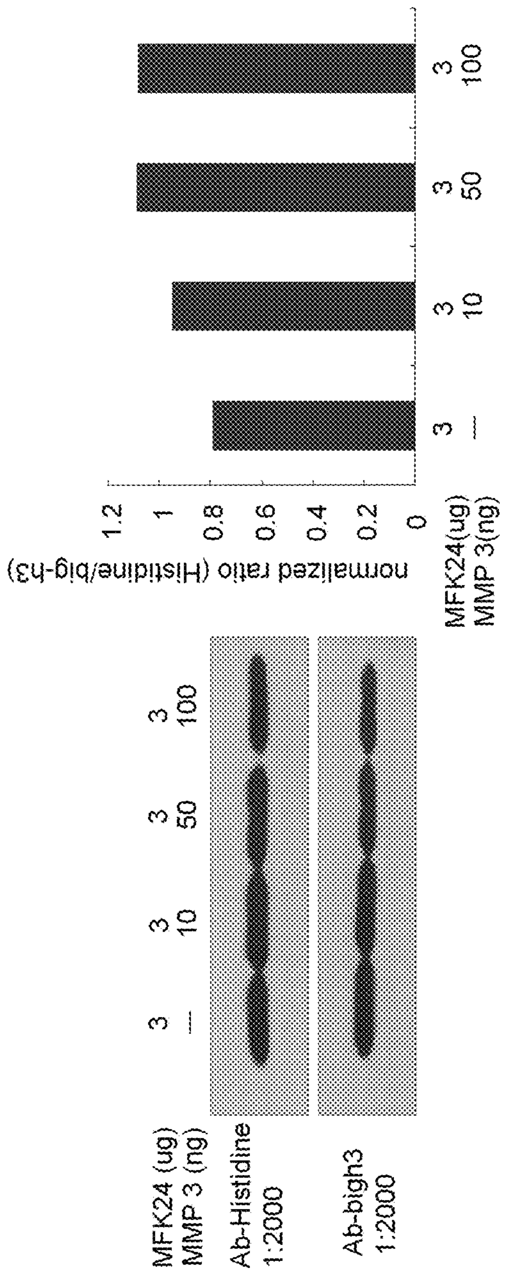
Figure 11D:
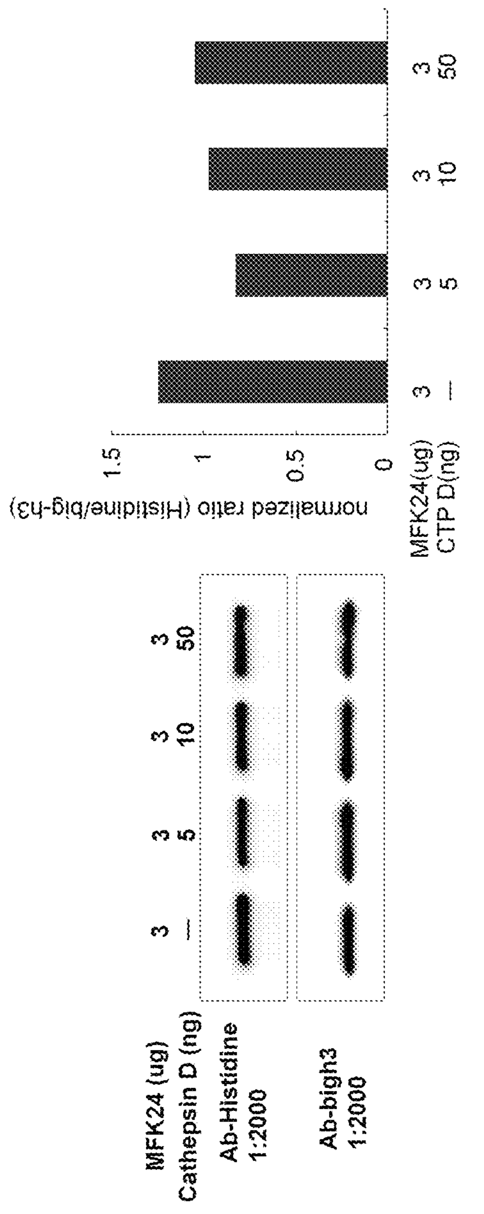
Figure 11E:
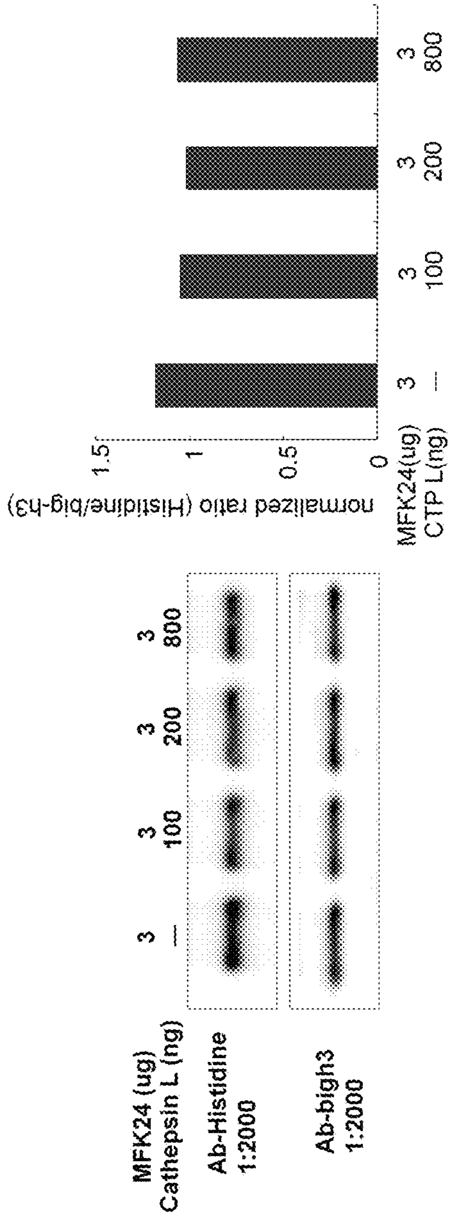
Figure 11F:
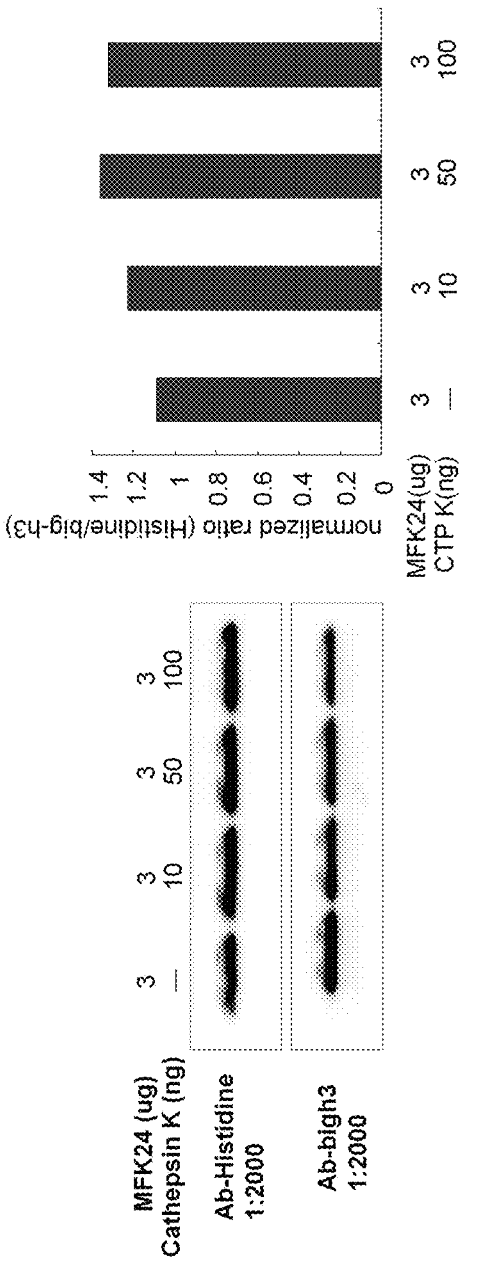
Figure 12A:
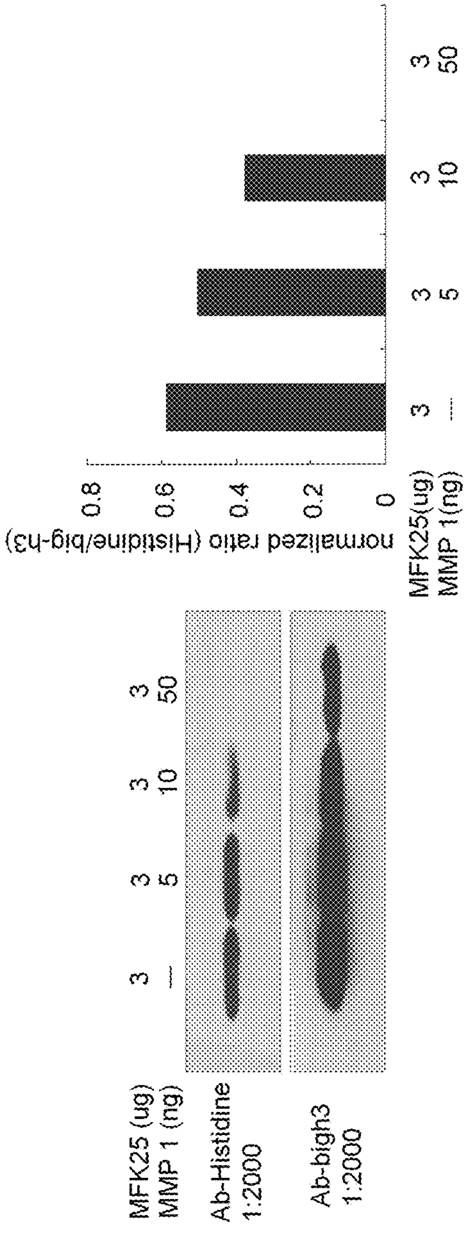
FIG. 12 is the result of an enzymatic digestion test of MMP-1, -2, and -3 and Cathepsin K, L, and D on an MFK25 peptide having an MMP-consensus substrate (MFK25(ug): an amount (ug) of administered MFK25 peptide; MMP1 (ng), MMP2(ng), MMP3(ng): an amount of MMP 1, MMP2 or MMP3 used in the digestive enzyme test; Cathepsin D(ng), Cathepsin L(ng), Cathepsin K(ng): an amount of cathepsin D, L or cathepsin K used in the digestive enzyme test; Ab-histidine: an amount of a peptide bound to an anti-histidine antibody; Ab-bigh3: an amount of a peptide bound to an anti-Bigh3 antibody; normalized ratio (histidine/big-h3): an amount of histidine/an amount of big-h3).
Figure 12B:
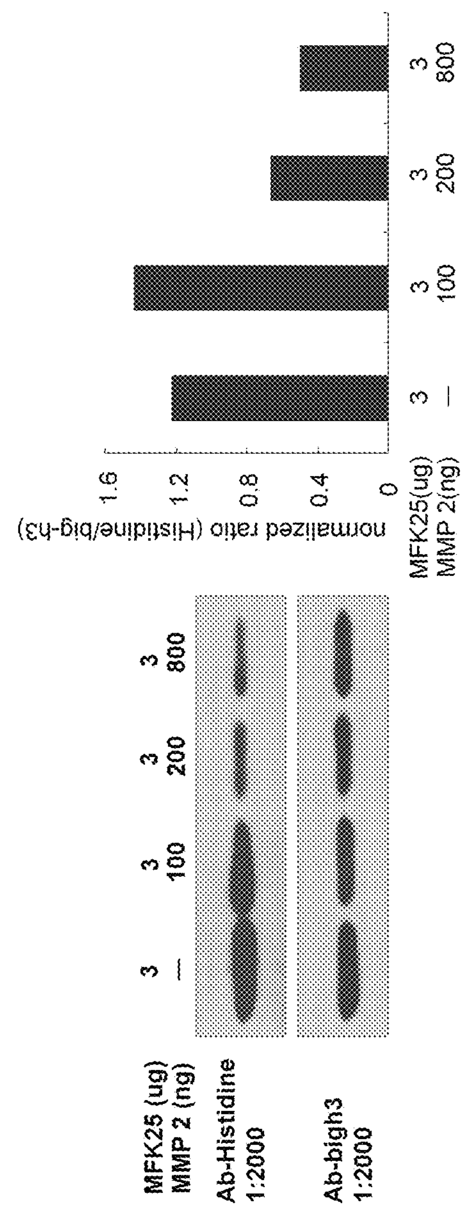
Figure 12C:
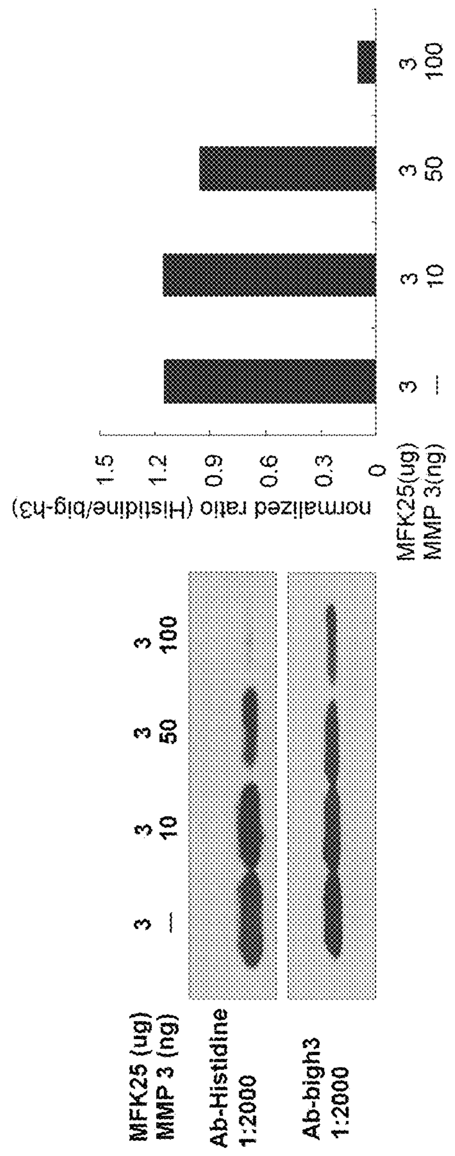
Figure 12D:
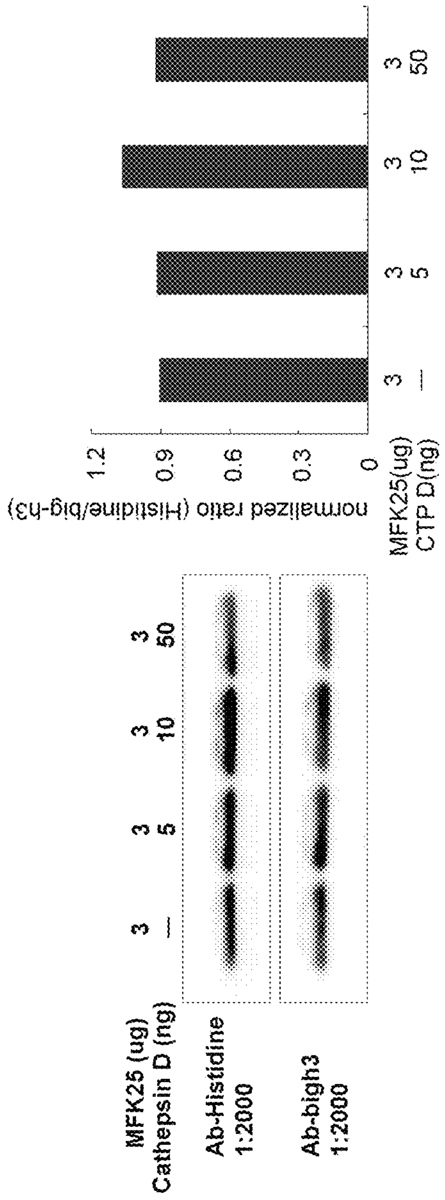
Figure 12E:
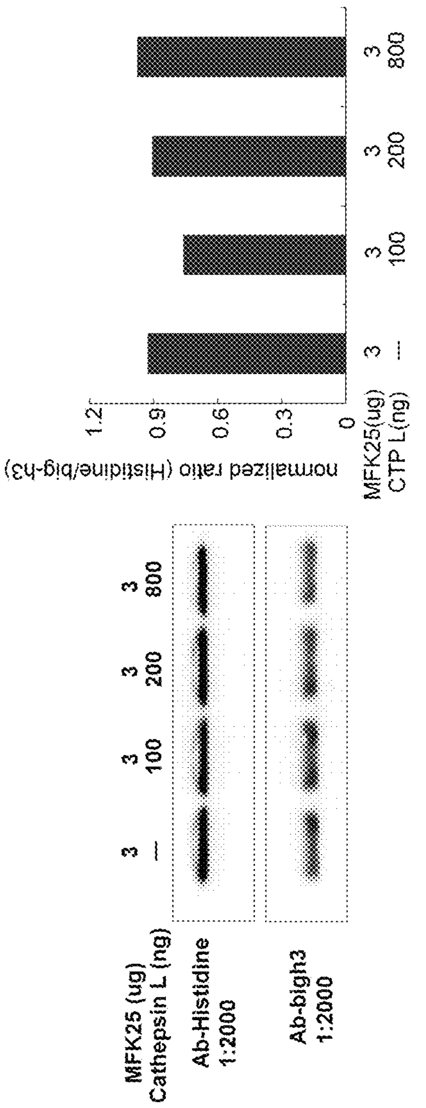
Figure 12F:
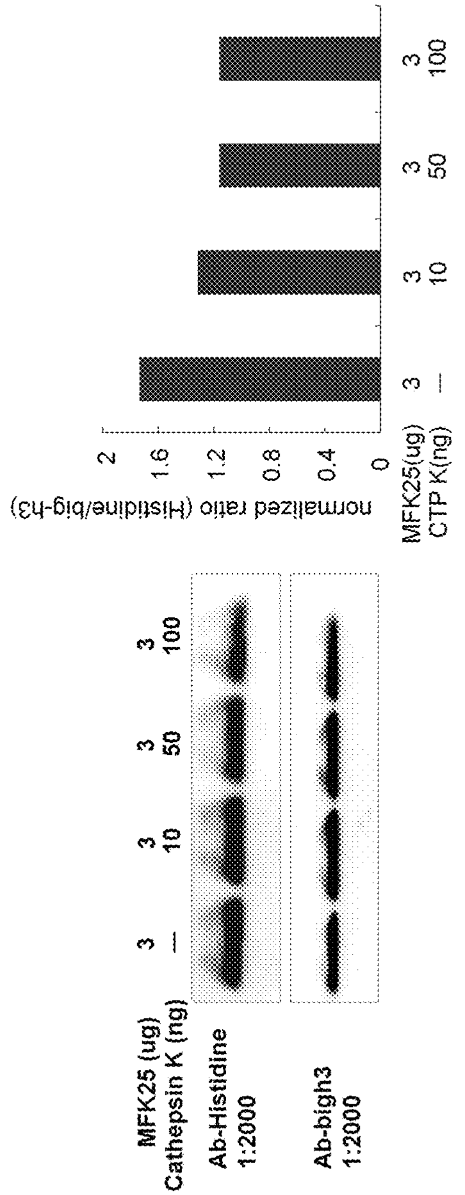

<1-1> Preparation and Separation I of mdhFas-1-MMPsubstrate-RGD Structural Peptide An mdhFas-1-MMPsubstrate-RGD structural peptide was cloned into a pET29b expression vector, and then transformed into *E. coli* BL21(DE3), BL21(DE3)pLyss or Rosetta(DE3). The transformed *E. coli* was cultured so as to express an mdhFas-1-MMPsubstrate-RGD structural peptide. A peptide having mdhFas-1 (as a basic structure) linked to an MMP2 substrate peptide and a QERGDSLA (SEQ ID NO: 10) peptide was referred to as an 'MFK23 peptide' (see FIG. 7) and a peptide having mdhFas-1 (as a basic structure) linked to an MMPI substrate peptide and a QERGDSLA (SEQ ID NO: 10) peptide was referred to as an 'MFK24 peptide' (see FIG. 8), and a peptide having mdhFas-1 (as a basic structure) linked to an MMP consensus substrate peptide and a QERGDSLA (SEQ ID NO: 10)peptide was referred to as an 'MFK25 peptide' (see FIG. 9).

A gene, which encodes a peptide prepared by removing H1 and H2 regions from the fourth fas-1 domain of mouse βig-h3 (that is, mdhFas-1), was PCR amplified by using mouse βig-h3 (NM_009369) as a template, and primers (forward 5'-tatcatatgcaagccatgcc-3' (SEQ ID NO: 27), reverse 5'-tcaccgaattccatgatgtc-3'(SEQ ID NO: 28)).

The amplified product was cloned into pET 29b expression vector by using restriction enzymes Nde I and EcoR I, and primers for an MMP substrate sequence (primers for an MMP1 substrate: forward 5'-AATTCGGACCACAAGGAATAGCAGGAG -3' (SEQ ID NO: 31), reverse 5'-TCGACTCCTGCTATTCCTTGTGGTCCG-3' (SEQ ID NO: 32); primers for an MMP2 substrate: forward 5'-AATTCGGACCACTGGGAGTCCGAGGAG-3' (SEQ ID NO: 33), reverse 5'-TCGACTCCTCGGACTCCCAGTGGTCCG-3 (SEQ ID NO: 34); primers for a consensus substrate: forward 5'-AATTCGGACCACTGGGAATAGCAGGAG-3',(SEQ ID NO: 35) reverse 5'-TCGACTCCTGCTATTCCCAGTGGTCCG-3' (SEQ ID NO: 36)) were complimentarily bound to the template and then, inserted into restriction enzymes EcoR I and Sal I on pET29b expression vector containing dhFas-1.

Also, in a QERGDSLA (SEQ ID NO: 10) peptide, primers (forward 5'-TCGACCAAGAACGAGGAGATTCTCTGGCAC-3', (SEQ ID NO: 37) reverse 5'-TCGAGTGCCAGAGAATCTCCTCGTTCTTGG-3'(SEQ ID NO: 38)) were complimentarily bound to the template and then, inserted into restriction enzymes Sal I and Xho I on pET 29b expression vector containing dhFas-1-MMP substrate sequence. Then, the vector was transformed into *E. coli* BL21DE.

TABLE 2

| Primers for vector | | |
|---|---|---|
| Name of Primer | SEQ ID NO: | sequence (5'-3') |
| mdhFas-1-forward | 27 | tatcatatgcaagccatgcc |
| mdhFas-1-reverse | 28 | tcaccgaattccatgatgtc |
| MMP1 substrate-forward | 31 | AATTCGGACCACAAGGAATA GCAGGAG |
| MMP1 substrate-reverse | 32 | TCGACTCCTGCTATTCCTTG TGGTCCG |
| MMP2 substrate-forward | 33 | AATTCGGACCACTGGGAGTC CGAGGAG |
| MMP2 substrate-reverse | 34 | TCGACTCCTCGGACTCCCAG TGGTCCG |
| MMP consensus substrate-forward | 35 | AATTCGGACCACTGGGAATA GCAGGAG |
| MMP consensus substrate-reverse | 36 | TCGACTCCTGCTATTCCCAG TGGTCCG |
| QERGDSLA (SEQ ID NO: 10)-forward | 37 | TCGACCAAGAACGAGGAGAT TCTCTGGCAC |
| QERGDSLA (SEQ ID NO: 10)-reverse | 38 | TCGAGTGCCAGAGAATCTCC TCGTTCTTGG |

<1-2> Preparation and Separation II of mdhFas-1-MMPsubstrate-RGD Structural Peptide An mdhFas-1-MMPsubstrate-RGD structural peptide was cloned into a pET29b expression vector, and then transformed into *E. coli* BL21(DE3), BL21(DE3)pLyss or Rosetta(DE3). The transformed *E. coli* was cultured so as to express an mdhFas-1-MMPsubstrate-RGD structural peptide. A peptide having mdhFas-1 (as a basic structure) linked to an MMP 3 substrate peptide and a QERGDSLA (SEQ ID NO: 10) peptide was referred to as an 'MFK27 peptide' (see FIG. 28).

In order to improve the expression of mdhFas-1-MMP3 substrate-RGD structural peptide in *E. coli*, a signal peptide sequence of mouse βig-h3 was PCR amplified by using mouse βig-h3(NM_009369) as a template, and primers (forward 5'-AGTACATATGATGGCGCTCCT-3' (SEQ ID NO: 39), reverse 5' -AGTAGATCTCTGCAAGGGTCCC (SEQ ID NO: 3'). The amplified product was cloned into pET 29b expression vector by using restriction enzymes Nde I and Bgl II.

A gene, which encodes a peptide prepared by removing H1 and H2 regions from the fourth fas-1 domain of mouse βig-h3(that is, mdhFas-1), was PCR amplified by using mouse βig-h3(NM_009369) as a template, and primers (forward 5'-ACAGATCTCAAGCCATGCCT-3' (SEQ ID NO: 41), reverse 5'-ACGAATTCCATGATGTCGGT-3' (SEQ ID NO: 42)). The amplified product was cloned into the pET 29b expression vector containing the signal peptide sequence by using restriction enzymes Bgl II and EcoR I.

Primers for an MMP3 substrate (forward 5'-AATTCGGACCACTGGGACTGTGGGCAAGAGGAG-3', (SEQ ID NO: 43) reverse 5'-TCGACTCCTCTTGCCCACAGTCCCAGTGGTCCG-3' (SEQ ID NO: 44)) were complimentarily bound to the template, and inserted into restriction enzymes EcoR I and Sal I on the pET29b expression vector containing the signal peptide sequence and the dhFas-1.

Also, in a QERGDSLA (SEQ ID NO: 10) peptide, primers (forward 5'-TCGACCAAGAACGAGGAGATTCTCTGGCAC-3',(SEQ ID NO: 37) reverse 5'-TCGAGTGCCAGAGAATCTCCTCGTTCTTGG-3' (SEQ ID NO: 38)) were complimentarily bound to the template, and then inserted into restriction enzymes Sal I and Xho I on the pET 29b expression vector containing the signal peptide sequence, the dhFas-1 and the MMP3 substrate sequence. Then, the vector was transformed into *E. coli* BL21DE.

tide. A peptide having hsdhFas-1 (as a basic structure) linked to an MMPI substrate peptide and a QERGDSLA (SEQ ID NO: 10) peptide was referred to as an 'hsFJ24 peptide' (see FIG. 29), and a peptide having hsdhFas-1 (as a basic structure) linked to an MMP consensus substrate peptide and a QERGDSLA (SEQ ID NO: 10) peptide was referred to as an 'hsFJ25 peptide' (see FIG. 30).

A gene, which encodes a peptide prepared by removing H1 and H2 regions from the fourth fas-1 domain of human βig-h3 (that is, hsdhFas-1), was PCR amplified by using human βig-h3(M77349) as a template, and primers (forward 5'-TATATCATATGCGAGCCCTG-3' (SEQ ID NO:45), reverse 5'-TATATCATATGCGAGCCCTG-3' (SEQ ID NO:46)). The amplified product was cloned into the pET 29b expression vector by using restriction enzymes Nde I and EcoR I. Then, primers for an MMP substrate sequence (primers for an MMPI substrate: forward 5'-AATTCGGACCACAAGGAATAGCAGGAG (SEQ ID NO: 31) -3', reverse 5'-TCGACTCCTGCTATTCCTTGTGGTCCG-3' (SEQ ID NO: 32); primers for an MMP3 substrate: forward 5'-AATTCGGACCACTGGGACTGTGGGCAAGAGGAG-3' (SEQ ID NO: 43), reverse 5'-TCGACTCCTCTTGCCCACAGTCCCAGTGGTCCG-3' (SEQ ID NO: 44); primers for a consensus substrate: forward 5'-AATTCGGACCACTGGGAATAGCAGGAG -3' (SEQ ID NO: 35), reverse 5'-TCGACTCCTGCTATTCCCAGTGGTCCG-3' (SEQ ID NO: 36)) were complimentarily bound to the template, and then inserted into restriction enzymes EcoR I and Sal I of the pET29b expression vector containing dhFas-1.

Also, in a QERGDSLA (SEQ ID NO: 10) peptide, primers (forward 5'-TCGACCAAGAACGAGGAGATTCTCTGGCAC-3' (SEQ ID NO: 37), reverse 5'-TCGAGTGCCAGAGAATCTCCTCGTTCTTGG-3' (SEQ ID NO: 38)) were complimentarily bound to the template, and then inserted into restriction enzymes Sal I and Xho I on pET 29b expression vector containing dhFas-1-MMP substrate sequence. Then, the vector was transformed into *E. coli* BL21DE.

TABLE 3

| Primers for vector | | |
|---|---|---|
| Name of Primer | SEQ ID NO: | sequence (5'-3') |
| mouse signal peptide-forward | 39 | AGTACATATGATGGCGCTCCT |
| mouse signal peptide-reverse | 40 | AGTAGATCTCTGCAAGGGTCCC |
| mdhFas-1-forward | 41 | ACAGATCTCAAGCCATGCCT |
| mdhFas-1-reverse | 42 | ACGAATTCCATGATGTCGGT |
| MMP3 substrate-forward | 43 | AATTCGGACCACTGGGACTGTGGGCAAGAGGAG |
| MMP3 substrate-reverse | 44 | TCGACTCCTCTTGCCCACAGTCCCAGTGGTCCG |
| QERGDSLA (SEQ ID NO: 10)-forward | 37 | TCGACCAAGAACGAGGAGATTCTCTGGCAC |
| QERGDSLA (SEQ ID NO: 10)-reverse | 38 | TCGAGTGCCAGAGAATCTCCTCGTTCTTGG |

<1-3> Preparation and Separation I of mdhFas-1-MMPsubstrate-RGD Structural Peptide hsdhFas-1-MMPsubstrate-RGD Structural Peptide An hsdhFas-1-MMPsubstrate-RGD structural peptide was cloned into a pET29b expression vector, and then transformed into *E. coli* BL21(DE3), BL21(DE3)pLyss or Rosetta(DE3). The transformed *E. coli* was cultured so as to express an hsdhFas-1-MMPsubstrate-RGD structural pep-

TABLE 4

| Primers for vector | | |
|---|---|---|
| Name of Primer | SEQ ID NO: | sequence (5'-3') |
| hsdhFas-1-forward | 45 | TATATCATATGCGAGCCCTG |
| hsdhFas-1-reverse | 46 | TATATCATATGCGAGCCCTG |
| MMP1 substrate-forward | 31 | AATTCGGACCACAAGGAATA GCAGGAG |
| MMP1 substrate-reverse | 32 | TCGACTCCTGCTATTCCTTG TGGTCCG |
| MMP consensus substrate-forward | 35 | AATTCGGACCACTGGGAATA GCAGGAG |
| MMP consensus substrate-reverse | 36 | TCGACTCCTGCTATTCCCAG TGGTCCG |
| QERGDSLA (SEQ ID NO: 10)-forward | 37 | TCGACCAAGAACGAGGAGAT TCTCTGGCAC |
| QERGDSLA (SEQ ID NO: 10)-reverse | 38 | TCGAGTGCCAGAGAATCTCC TCGTTCTTGG |

<1-4> Preparation and Separation II of hsdhFas-1-MMP-substrate-RGD Structural Peptide An hsdhFas-1-MMPsubstrate-RGD structural peptide was cloned into a pET29b expression vector, and then transformed into *E. coli* BL21(DE3), BL21(DE3)pLyss or Rosetta(DE3). The transformed *E. coli* was cultured so as to express an hsdhFas-1-MMPsubstrate-RGD structural peptide. a peptide having hsdhFas-1 (as a basic structure) linked to an MMP 3 substrate peptide was referred to as an 'hsFJ27 peptide' (see FIG. 31).

In order to improve the expression of hsdhFas-1-MMP3 substrate-RGD structural peptide in *E. coli*, a signal peptide sequence of human βig-h3 was PCR amplified by using human βig-h3(M77349) as a template, and primers (forward 5'-ATGCATATGATGGCGCTCTTC-3' (SEQ ID NO: 47), reverse 5'-AGTAGATCTCTGCAAGGGTCCC3' (SEQ ID NO: 48)). The amplified product was cloned into pET 29b expression vector by using restriction enzymes Nde I and Bgl II.

A gene, which encodes a peptide prepared by removing H1 and H2 regions from the fourth fas-1 domain of human βig-h3 (that is, hsdhFas-1), was PCR amplified by using human βig-h3(M77349) as a template, and primers (forward 5'-AAGATCTTTCCGAGCCCTG-3' (SEQ ID NO: 49, reverse 5'-ACCGAATTCCATGATGTCAGG-3' (SEQ ID NO: 50)). The amplified product was cloned into the pET 29b expression vector containing the signal peptide sequence by using restriction enzymes Bgl II and EcoR I.

Primers for an MMP3 substrate (forward 5'-AATTCG-GACCACTGGGACTGTGGGCAAGAGGAG-3' (SEQ ID NO: 43), reverse 5'-TCGACTCCTCTTGCCCACAGTC-CCAGTGGTCCG-3'(SEQ ID NO: 44)) were complimentarily bound to the template, and inserted into restriction enzymes EcoR I and Sal I of the pET 29b expression vector containing the signal peptide sequence and the dhFas-1.

Also, in a QERGDSLA (SEQ ID NO: 10) peptide, primers (forward 5'-TCGACCAAGAACGAGGAGAT-TCTCTGGCAC-3' (SEQ ID NO: 37), reverse 5'-TCGAGT-GCCAGAGAATCTCCTCGTTCTTGG-3' (SEQ ID NO: 38)) were complimentarily bound to the template, and then inserted into restriction enzymes Sal I and Xho I on the pET 29b expression vector containing the signal peptide sequence, the dhFas-1 and the MMP3 substrate sequence. Then, the vector was transformed into *E. coli* BL21DE.

TABLE 5

| Primers for Vector | | |
|---|---|---|
| Name of Primer | SEQ ID NO: | sequence (5'-3') |
| human signal peptide-forward | 47 | ATGCATATGATGGCGCTCTTC |
| human signal peptide-reverse | 48 | AGTAGATCTCTGCAAGGGTCCC |
| hsdhFas-1-forward | 49 | AAGATCTTTCCGAGCCCTG |
| hsdhFas-1-reverse | 50 | ACCGAATTCCATGATGTCAGG |
| MMP3 substrate-forward | 43 | AATTCGGACCACTGGGACTGTG GGCAAGAGGAG |
| MMP3 substrate-reverse | 44 | TCGACTCCTCTTGCCCACAGTC CCAGTGGTCCG |
| QERGDSLA (SEQ ID NO: 10)-forward | 37 | TCGACCAAGAACGAGGAGATTC TCTGGCAC |
| QERGDSLA (SEQ ID NO: 10)-reverse | 38 | TCGAGTGCCAGAGAATCTCCTC GTTCTTGG |

TABLE 6

| dhFas-1-MMP substrate-RGD structural peptide | | |
|---|---|---|
| Name | structure | characteristics |
| MFK23 | mdhFas-1-GPLGVRG (SEQ ID NO: 5)-QERGDSLA (SEQ ID NO: 10) | insertion of MMP2 substrate sequence |
| MFK24 | mdhFas-1-GPQGIAG (SEQ ID NO: 6)-QERGDSLA (SEQ ID NO: 10) | insertion of MMP1 substrate sequence |
| MFK25 | mdhFas-1-GPLGIAG (SEQ ID NO: 7)-QERGDSLA (SEQ ID NO: 10) | insertion of consensus substrate sequence |
| MFK27 | mdhFas-1-GPLGLWARG (SEQ ID NO: 8)-QERGDSLA (SEQ ID NO: 10) | insertion of MMP3 substrate sequence |
| hsFJ24 | hsdhFas-1-GPQGIAG (SEQ ID NO: 6)-QERGDSLA (SEQ ID NO: 10) | insertion of MMP1 substrate sequence |
| hsFJ25 | hsdhFas-1-GPLGIAG (SEQ ID NO: 7)-QERGDSLA (SEQ ID NO: 10) | insertion of consensus substrate sequence |
| hsFJ27 | hsdhFas-1-GPLGLWARG (SEQ ID NO: 8)-QERGDSLA (SEQ ID NO: 10) | insertion of MMP3 substrate sequence |

<1-5> Separation and Identification of dhFas-1-MMPsubstrate-RGD Structural Peptide Through the culture of a strain transformed in Examples <1-1> to <1-4>, a dhFas-1-MMPsubstrate-RGD structural peptide was overexpressed and then separated and identified.

The culture medium obtained after overexpression was subjected to centrifugation (at 4° C., 2000 g) for 20 minutes. The supernatant was removed and only cells were collected. A lysis buffer (50 mM Tris-Cl (pH8.0), 500 mM NaCl, 0.5 mM EDTA, 1 mM PMSF, 1 mM DTT, 1% Triton X-114) was added in an amount of 4 ml with respect to 100 ml culture medium, to a cell pellet, and the mixture was stirred. Then, the cells were broken by ultrasonic waves. The broken cells were subjected to centrifugation (at 4° C., 13000 rpm) for 15 minutes, and the supernatant (50 ml) was transferred to a tube. Ni-NTA Agarose beads (QIAGEN) were well mixed, and 3 ml of them were transferred to a tube, and washed with binding buffer (50 mMTris-Cl (pH8.0), 500 mMNaCl, 5 mM Imidazole (pH 7.8) twice. The washed Ni-NTA Agarose beads in a state of 50% suspension were added with the supernatant, agitated at 4° C. by an agitator for 2 hours, and transferred to a column. Then, at 4° C., the Ni-NTA Agarose beads were added with and washed with washing buffer (50 mM Tris-Cl (pH8.0), 500 mMNaCl, 20 mM Imidazole (pH 7.8), 0.1% Triton X-114) in a volume 10 times larger with respect to the Agarose beads so as to remove non-specifically bound proteins. An elution buffer (50 mM Tris-Cl (pH8.0), 500 mM NaCl, 300 mM Imidazole (pH 7.8)) was used to extract the inventive peptide. In order to maintain 1 EU or less of LPS (Lipopolysaccharide) per mouse in the produced recombinant protein, Triton X-114 was used to remove LPS. Then, the LPS was removed again from the separated peptide by using an LPS removing column (Cambrex, Germany).

As a result, as shown in FIGS. 7 to 9 FIGS. 28 to 31, it was found that MFK23, MFK24, MFK25, MFK27, HsFJ24, HsFJ25 and HsFJ27 were over-expressed and separated through a purification process.

Example 2

An Enzymatic Digestion Test on mdhFas-1-MMPsubstrate-RGD Structural Peptide

In order to determine that MFK23, MFK24 and MFK25 were cleaved by specific MMPs, an enzyme analysis and a culture analysis were carried out.

<2-1> An Enzymatic Digestion Test on mdhFas-1-MMP-substrate-RGD Structural Peptide 3 ug of synthesized mdhFas-1-MMPsubstrate structure modified protein, together with MMP1 (5 ng, 10 ng and 50 ng), MMP2 (100 ng, 200 ng and 800 ng), MMP3 (10 ng, 50 ng and 100 ng), cathepsin D (5 ng, 10 ng and 50 ng), cathepsin L (100 ng, 200 ng and 800 ng), and cathepsin K (10 ng, 50 ng and 100 ng), was mixed with enzyme buffer (150 mM NaCl, 5 mM. CaCl2, 20 mM Tris-HCl pH7.5), and reacted at 37° C. for 4 hours. The resultant product was subjected to electrophoresis through 15% polyacrylamide gel, transferred to a Nitrocellulose Membrane (Schleicher & Schuell), blocked at room temperature for 1 hour with TBST solution containing 3% BSA (20 mmole/L Tris-HCl, 137 mmole//l NaCl, 0.1% Tween-20), washed TBST solution three times (each for 10 minutes), and reacted with primary antibody (anti-Histidine or anti-Bigh3) for 1 hour. The resultant product was washed with TBST solution three times (each for 10 minutes), reacted with a secondary antibody conjugated to horseradish peroxidase (HRP) for 1 hour, washed TBST solution three times (each for 10 minutes), and visualized by ECL (Amersham Biosciences, UK) so as to detect the change in the amount of mdhFas-1-MMPsubstrate-RGD structural peptide.

As a result, as shown in FIG. 10, it was found that MFK23 was concentration-dependently cleaved through treatment with MMP-2, and was not cleaved through treatment with other kinds of MMPs such as MMP-1 or MMP-3. Also, it was found that MFK23 was not cleaved through treatment with cathepsin K, L or D (cysteine protease).

Also, as shown in FIG. 11, it was found that MFK24 was concentration-dependently cleaved through treatment with MMP-1, and was not cleaved through treatment with other kinds of MMPs such as MMP-2 or MMP-3. or cathepsin K, L or D.

Also, as shown in FIG. 12, it was found that MFK25 was concentration-dependently cleaved through treatment with MMP-1, MMP-2 and MMP-3, and especially, well cleaved by MMP-1 and MMP-3. However, it was found that MFK25 was not cleaved through treatment with cathepsin K, L or D (cysteine protease).

<2-2> a Culture Analysis on the Enzymatic Digestion of mdhFas-1-MMPsubstrate-RGD Structural Peptide In order to determine if MFK24 is well adhered to cells and in actuality cleaved by MMP-1, human FLS (fibroblast-like synovicyte) was treated with IL-1β so as to amplify the expression of MMP-1. Then, MFK24 was added in a culture medium and cultured.

In a culture medium of DMEM+10% FBS (fetal bovine serum)+2% penicillin, streptomycin, a human Synovial membrane cell line was cultured for 2 days, added with 0.1 ng/ml IL-1β, and stimulated for 24 hours. The cell line was treated with mdhFas-1-MMPsubstrate-RGD structural peptide (1 uM), and stimulated for 3 hours and 6 hours. Then, by using an anti-βig-h3 antibody recognizing mdhfas-1, and an anti-histidine antibody recognizing C-terminal histidine-tag, the amount of peptide was determined.

Figure 13:
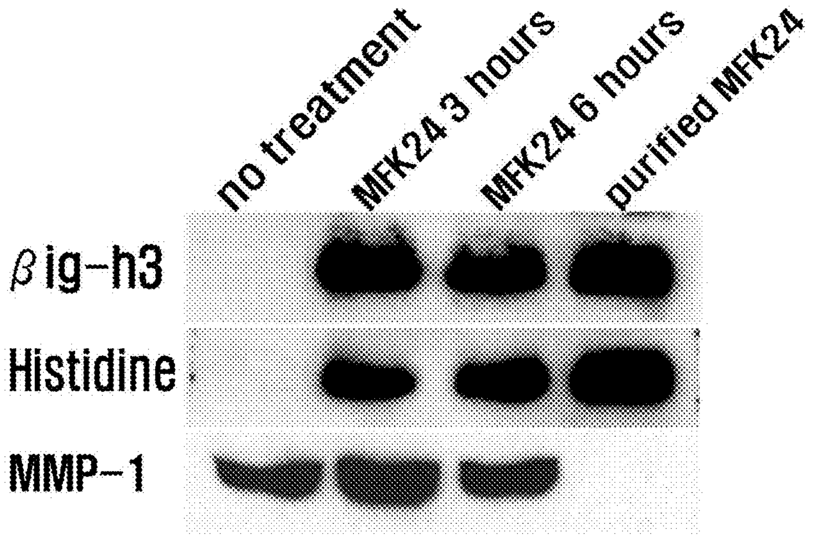
FIG. 13 is the result of an enzymatic digestion test on MFK24 peptide cleaved by MMP-1 secreted from a human Synovial membrane cell (βig-h3: an amount of peptide, measured by anti-βig-h3; Histidine: an amount of peptide, measured by anti-histidine; MMP-1: an amount of MMP-1; no treatment: not treated with MFK24; MFK24 3 hours: measured after 3 hours from treatment with MFK24; MFK24 6 hours: measured after 6 hours from treatment with MFK24; purified MFK24: purified MFK24 treated with anti-βig-h3, and anti-histidine).

As a result, it was found that as shown in FIG. 13, in the use of the anti-histidine antibody, MFK24 was measured in a smaller amount than that in the use of the anti-βig-h3 antibody. Accordingly, it was found that MFK24 was cleaved by MMP-1 secreted from a Synovial membrane cell.

Example 3

A Test of mdhFas-1-MMPsubstrate-RGD Structural Peptide' Function Modulation on a Cell Line <3-1> Cell Adhesion Test βig-h3 was introduced into a 96-well plate at a concentration of 5 ug/ml, and coated for 14 hours at 4° C. In DMEM+0.5% BSA (Bovine Serum Albumin) culture medium, mouse fibroblast (NIH3T3) was introduced, and MFK23, MFK24, MFK25 or MFK27 at concentrations was injected thereto, followed by mixing. The resultant mixture was cultured at 37° C. for 30 minutes, and plated on a coated well. It was cultured for 2 hours, and washed with PBS (phosphate buffered saline) so as to remove unattached cells, and then added with a substrate (4-Nitrophenyl N-acetyl-β-D-glucosaminide, Sigma, U.S.) to be activated by β-N-acetylglucosaminidase within the cell, followed by culturing at 37° C. for 1 hour. Then, a glycine EDTA solution (0.5M EDTA, 50 mM glycine, pH 10.4) was added thereto, and the coloring extent according to the number of attached cells was measured by absorbance.

Figure 14:
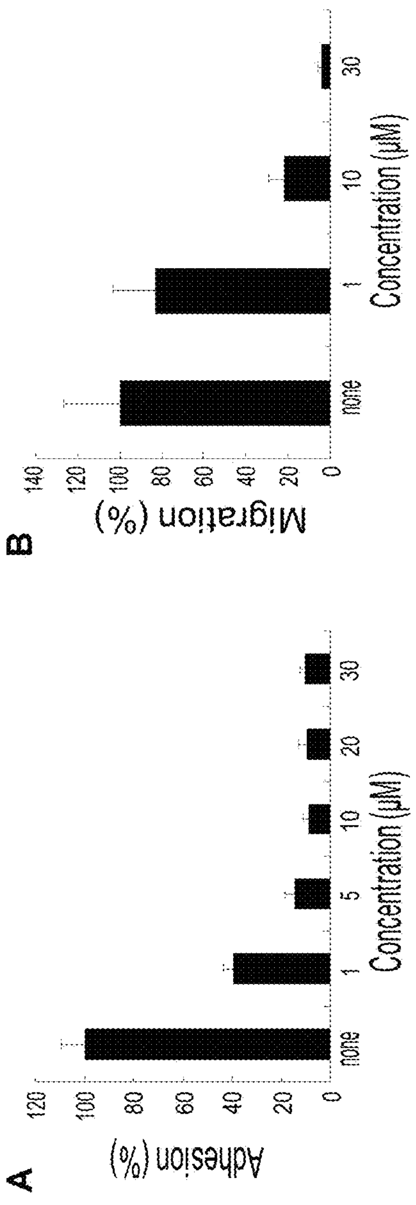
FIG. 14 is the result showing that adhesion (A) and migration (B) of βig-h3-mediated NIH3T3 cell line were concentration-dependently inhibited by MFK23 (Adhesion (%): cell adherence (relative adherence with respect to 100% of control group), Migration(%): cell migration (relative migration respect to 100% of control group), Concentration (uM): concentration of added peptide).

As a result, as shown in FIG. 14, it was found that the treatment of MFK23 at a concentration of 5 uM or more inhibited the adhesion.

Also, as shown in FIGS. 14, 15, 16 and 32, it was found that MFK23, MFK24, MFK25 and MFK27 even at a very low concentration can inhibit the cell adhesion. Specially, it was found that the treatment of MFK24 can inhibit the cell adhesion at very low concentration unlike the treatment of YH18 motif and mdhFas-1, alone or in combination.

mdhFas-1 and RGDSP (SEQ ID NO: 9)(peptide including an amino acid sequence of RGDSP (SEQ ID NO: 9)), alone or in combination, were used to carry out the same cell adhesion test, and the test result was compared to that by MFK24.

As a result, as shown in FIG. 15C, MFK24 at a concentration of 0.5uM showed a high adhesion inhibiting effect of 80% or more while mdhFas-1 and RGDSP (SEQ ID NO: 9), at the same concentration, showed adhesion inhibiting effects of 50% and 0%, respectively. Also, the treatment with both mdhFas-1 and RGDSP (SEQ ID NO: 9) showed an adhesion inhibiting effect of about 50%. Accordingly, it was found that MFK24 can more effectively inhibit the cell adhesion compared to mdhFas-1 and RGDSP(SEQ ID NO: 9).

Accordingly, it was determined that the mdhFas-1-MMP-substrate-RGD structural peptide shows a significantly high effect on rheumatoid arthritis compared to mdhFas-1, RGDSP (SEQ ID NO: 9), and YH18 motif.

<3-2> Cell Migration Test

In the lower compartment of a transwell filter having an 8 um hole size allowing cells to be migrated, βig-h3 was cultured at 4° C. for 12 to 14 hours and coated. In DMEM+0.5% BSA culture medium, NIH3T3 was introduced, and administered with MFK23, MFK24 or MFK25 at concentrations, followed by mixing. The resultant mixture was cultured at 37° C. for 30 minutes, inoculated into the upper chamber of the coated well, and cultured for 7 hours at 37° C. Then, the cells migrated to the lower compartment of the filter were fixed by paraformaldehyde, and strained by a crystal violet. The cells were not transferred to a sterilized cotton swab while the cells remaining in the upper chamber were wiped out and the number of cells migrated to the lower compartment was microscopically counted.

Figure 15:
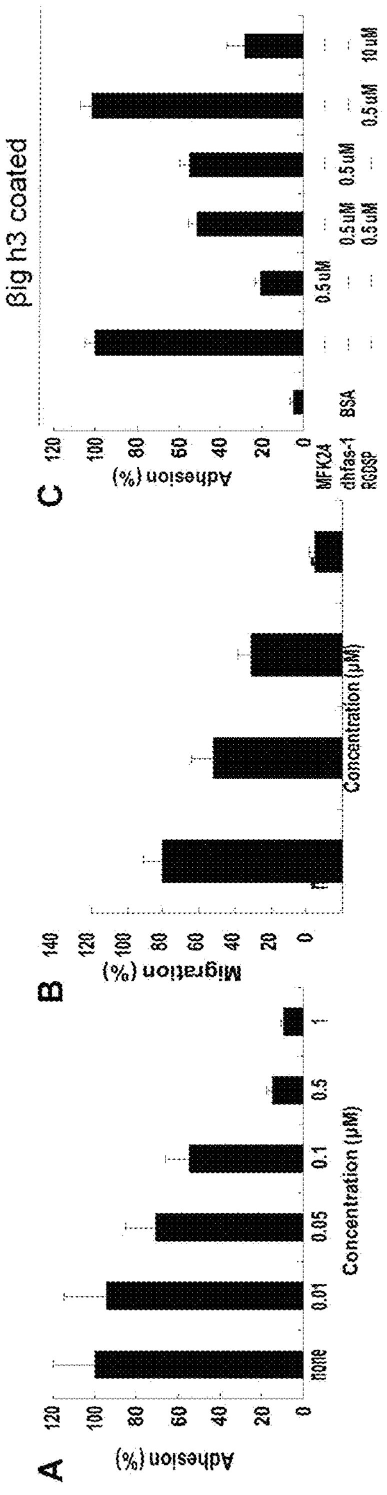
FIG. 15 is the result showing that adhesion (A) and migration (B) of βig-h3-mediated NIH3T3 cell line were concentration-dependently inhibited by MFK24.
Figure 16:
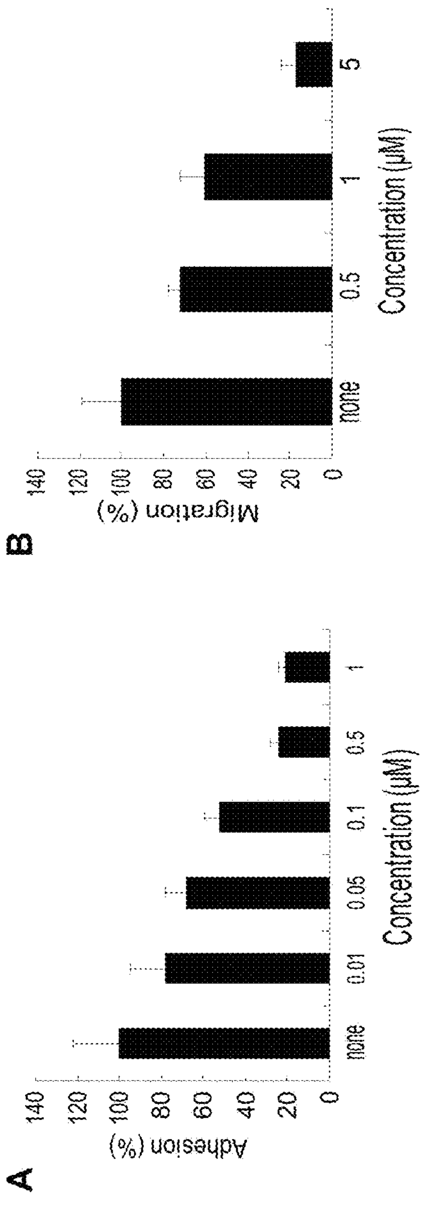
FIG. 16 is the result showing that adhesion (A) and migration (B) of βig-h3-mediated NIH3T3 cell line were concentration-dependently inhibited by MFK25 (Adhesion (%): cell adherence (relative adherence with respect to 100% of control group), Migration(%): cell migration (relative migration respect to 100% of control group), Concentration (uM): concentration of added peptide).

As shown in FIGS. 14, 15 and 16, it was found that MFK23, MFK24 and MFK25 inhibited the cell migration.

Example 4

A Test of hsdhFas-1-MMPsubstrate-RGD Structural Peptide' Function Modulation on a Cell Line <4-1> Cell Adhesion Test βig-h3 was introduced into a 96-well plate at a concentration of 5 ug/ml, and coated for 14 hours at 4° C. In DMEM+0.5% BSA (Bovine Serum Albumin) culture medium, human fibroblast-like synovicyte (FLS) was introduced, and HsFJ24, HsFJ25 or HsFJ27 at concentrations was injected thereto, followed by mixing. The resultant mixture was cultured at 37° C. for 30 minutes, and plated on a coated well. It was cultured for 2 hours, and washed with PBS (phosphate buffered saline) so as to remove unattached cells, and then added with a substrate (4-Nitrophenyl N-acetyl-β-D-glucosaminide, Sigma, U.S.) to be activated by β-N-acetylglucosaminidase within the cell, followed by culturing at 37° C. for 1 hour. Then, a glycine EDTA solution (0.5M EDTA, 50 mM glycine, pH 10.4) was added thereto, and the coloring extent according to the number of attached cells was measured by absorbance.

As a result, as shown in FIG. 33 to FIG. 35, it was found that the treatment of HsFJ24, HsFJ25 or HsFJ27 at a concentration of 5 uM or more inhibited the adhesion.

Example 5

Examination on an Arthritis Therapeutic Effect by mdhFas-1-MMPsubstrate-RGD Structural Peptide <5-1> Production of a Collagen-Induced Arthritis (CIA) Mouse Model A CIA mouse model having the similar characteristic to that of human rheumatoid arthritis was prepared according to the description in a known literature (Protocol for the successful induction of collagen-induced arthritis (CIA) and collagen antibody-induced arthritis (CAIA) in mice. Chondrex, Redmond, Wash.): Bovine type 2 collagen 100 ug was mixed with Freund's complete adjuvant, and hypodermically inoculated into the tail of the mouse. After 3 weeks, bovine type 2 collagen 100 ug was mixed with Freund's incomplete adjuvant, and inoculated again into the tail of the mouse. Then, the mouse was used in the experiment.

<5-2> A Test on an Arthritis Therapeutic Effect by mdhFas-1-MMPsubstrate-RGD Structural Peptide in a CIA Mouse By using a CIA mouse, an arthritis therapeutic effect by MFK23 and MFK24 was tested.

In order to find out the therapeutic effect of arthritis in a CIA model, for four weeks from the onset (the 23rd day) of arthritis following the second injection of the bovine type 2 collagen, MFK23 or MFK24 was daily injected into the abdominal cavity in doses of 0.1 mg/kg, 1 mg/kg, 10 mg/kg and 30 mg/kg. As a control group, the same amount of PBS was injected into the abdominal cavity. From the 23rd day to the 50th day, by using a Clinical arthritis index, the severity of arthritis was daily determined. The determination was based on the following data.

0; no symptom, 1; edema in one articulation or light edema, 2; severe edema in 2 or more articulations, 3; severe edema in most articulations, 4; severe edema in the whole of legs.

Figure 17A:
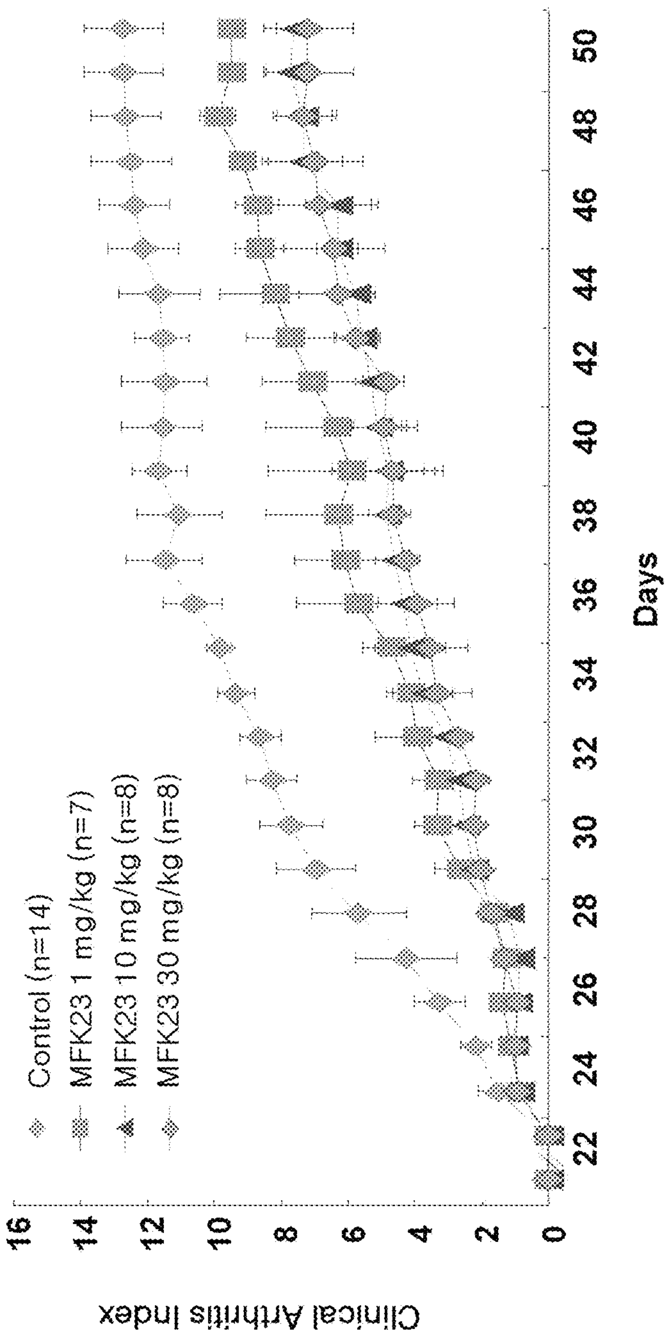
FIG. 17 shows the measurement result (A) of an arthritis inhibiting effect by MFK23 by a clinical arthritis index in a mouse CIA model, and the measurement result (B) of the weight of the experimental mouse (Clinical Arthritis Index: clinical arthritis index; Days: days since administration of collagen injection for arthritis induction; Control: control group administered with PBS instead of peptide; MFK23 1 mg/kg, MFK23 10 mg/kg, MFK23 30 mg/kg: groups administered with MFK23 in amounts of 1 mg/kg, 10 mg/kg, and 30 mg/kg per day; weight(g): body weight(g); before: before administration of peptide (on 22nd day); after: after administration of peptide (on 48th day)).
Figure 17B:
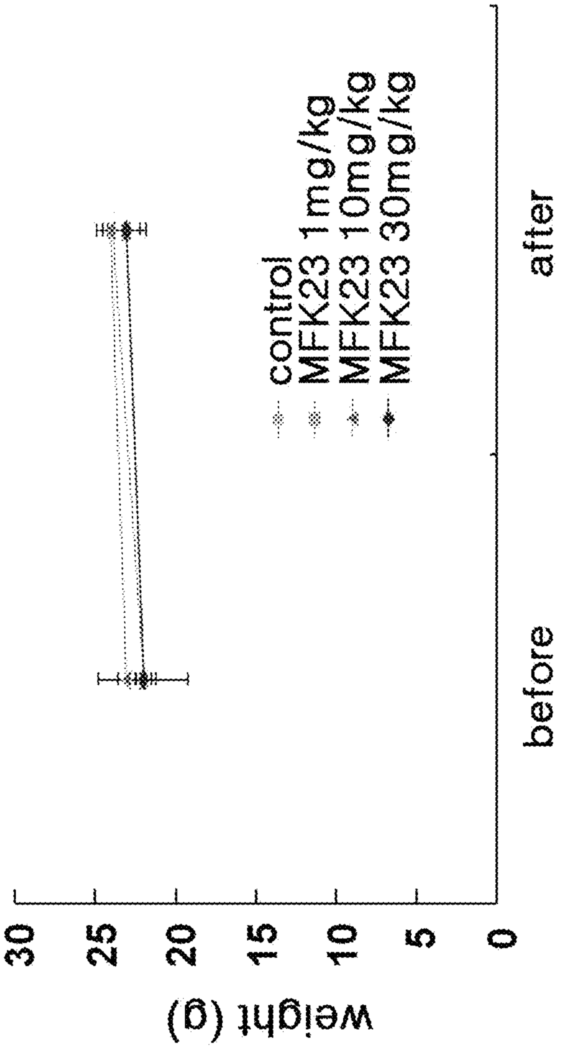

As a result, as shown in FIG. 17, it was found that MFK23 showed an excellent effect on arthritis.

Also, as shown in FIG. 19, it was found that MFK24 inhibited arthritis by about 70% even when administered in a dose of 0.1 mg/kg. Also, it was found that MFK24 even at a low concentration (1/100 of conventional mdhFas-1 or MFK12) shows a higher arthritis inhibiting effect than the conventional mdhFas-1 or MFK12 (see <Comparative Example 3> and <Comparative Example 4>).

<5-3> A Toxicity Test on mdhFas-1-MMPsubstrate-RGD Structural Peptide in a CIA Mouse In order to determine if mdhFas-1-MMPsubstrate-RGD structural peptide shows toxicity, in the CIA model, before the administration (on the 22nd day) and after the administration (on the 48th day), the mouse was weighed. On the 48th day, a serologic test and a blood test were carried out.

As a result, as noted in [table 7], it was found that as compared to a control group, MFK24 did not show abnormalities in the amounts of erythrocytes, leukocytes, and platelets, and liver function values (AST and ALT). Also, it was found that there is no significant difference in bilirubin and creatine between the control group and the group treated with MFK24.

Also, the weight of the MFK24-treated group was maintained similarly to that of the control group (see FIG. 19B). Also, the weight of the MFK23-treated group was maintained similarly to that of the control group (see FIG. 17B).

No mouse died during the therapy period. Also, from the results of the serologic test and the blood test, and the weight comparison, it was found that the treatment with MFK23 and MFK24 show a low toxicity and a low dangerousness.

TABLE 7

| Bood test results after treating MFK24 peptide to CIA model for 4 weeks | | | | | | | |
|---|---|---|---|---|---|---|---|
| Animal ID | RBC ($\times 10^6$/ul) | WBC ($\times 10^3$/ul) | PLT ($\times 10^3$/ul) | AST (U/L) | ALT (U/L) | BUN (mg/dL) | Crea (mg/dL) |
| control | 11.4 ± 0.8 | 6.7 ± 3.0 | 1062.6 ± 261 | 272.8 ± 36 | 62.9 ± 11.9 | 22.7 ± 0.0 | 0.45 ± 0.00 |
| 0.1 mg/kg | 12.3 ± 0.7 | 5.0 ± 1.2 | 1280.2 ± 284 | 224.3 ± 13 | 37.8 ± 7.1 | 19.0 ± 3.3 | 0.54 ± 0.10 |
| 1 mg/kg | 10.9 ± 1.7 | 3.7 ± 0.5 | 1155.3 ± 184 | 270.5 ± 17 | 40.6 ± 7.2 | 21.2 ± 3.4 | 0.54 ± 0.14 |
| 10 mg/kg | 11.4 ± 1.5 | 5.0 ± 1.8 | 1050.1 ± 359 | 222.0 ± 25 | 43.6 ± 14.2 | 20.4 ± 4.4 | 0.54 ± 0.11 |
| 30 mg/kg | 12.4 ± 0.1 | 6.1 ± 1.1 | 674.7 ± 111 | 286.6 ± 48 | 28.9 ± 8.2 | 12.4 ± 4.8 | 0.33 ± 0.02 |

Example 6

Examination on an Arthritis Inhibiting Mechanism by mdhFas-1-MMPsubstrate-RGD Structural Peptide In order to determine the action mechanism of an arthritis therapeutic effect in a CIA model, on the 50th day following the second injection of the bovine type 2 collagen (after 4 weeks from the onset (the 23rd day) of arthritis following the second injection of the bovine type 2 collagen), foot tissues of treatment groups were separated and subjected to histologic analysis. Then, in the tissues, a change in the expression of inflammatory mediators was examined.

<6-1> A Histologic Test on a Foot Tissue of a Mouse Administered with mdhFas-1-MMPsubstrate-RGD Structural Peptide The groups administered with MFK23 and MFK24 were HE-stained.

A tissue sample was prepared by the following process. Skin on the foot tissue was removed. Then, the tissue was fixed in 10% formalin solution for 2 days, and demineralized in 10% EDTA solution. The demineralized tissue was subjected to a dehydrating process and a clearing process, paraffin-embedded, and was made into a fragment with a thickness of 3 um by a microtome. The tissue fragment was deparaffinized and re-dehydrated by 100% xylene and ethanol, and then non-specific peroxidase within the tissue was blocked by a solution of 0.3% hydrogen peroxide dissolved in 100% methanol.

In order to carry out an immunohistochemistry test, binding of non-specific protein was blocked by 5% BSA. Then, the tissue was cultured, together with each primary antibody (as endothelial cell markers, an antibody to CD31, and an antibody to ICAM-1 (intercellular adhesion molecule-1)), at 4° C. for 12 to 14 hours, and washed with washing buffer (0.1% BSA, 0.2% gelatin, 0.05% saponin). It was cultured together with a secondary antibody labeled with biotin at room temperature for 30 minutes, was washed, reacted with Vectastatin ABC kit (Vector Laboratories, U.S.), and was mounted with Eukitt mounting media (Fluka, Germany) for observation.

Figure 18:
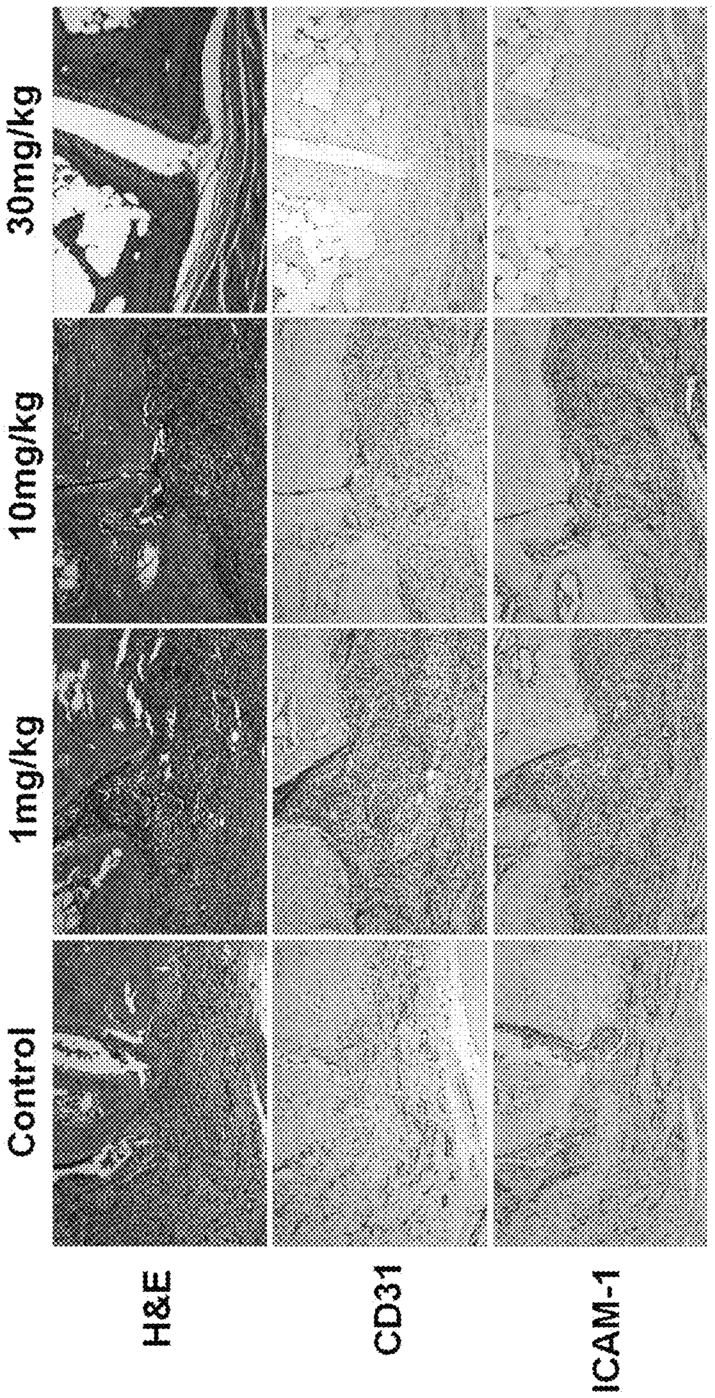
FIG. 18 shows a Synovial membrane tissue of a CIA mouse model treated with MFK23, which was observed through HE stain (control: control group administered with PBS instead of peptide; 1 mg/kg, 10 mg/kg, 30 mg/kg.

It was found that as shown in FIGS. 18 and 20, in groups treated with MFK23 and groups treated with MFK24, we found that they inhibited the proliferation of a Synovial membrane cell, and reduced the deformation of cartilage and bones.

<6-2> Examination of the Change in Inflammatory Mediators in a Foot Tissue of a Mouse Administered with mdhFas-1-MMPsubstrate-RGD Structural Peptide The distribution of inflammation in the foot tissue may be somewhat differently observed according to the regions, and its quantitative research is difficult. Thus, in the hind leg of a mouse CIA model treated with MFK24, the change in inflammatory mediators according to the onset of arthritis was measured by a semiquantitative reverse transcription PCR method using a Taqman probe, as described below.

From a mouse CIA model, a foot tissue was separated, and its skin was removed. The remaining tissue was grinded by a tissue homogenizer, and an extraction reagent (Easy-spim™, Intron) was used to extract all RNAs. They were quantified, and for 7 μg of RNA, a reverse transcriptase reaction was carried out by using AMV reverse transcriptase (Roche, 0.5 ul), oligo dT (Roche, 1 ul), and 10 mM dNTP (Takara, 2 ul) RNase inhibitor (Roche, 0.1 ul). For TNF-a, RANKL, IL-1β, CCL-2, MMP-1, MMP-3, IL-6, VCAM-1 and 18S RNA of a mouse, semiquantitative PCR was performed by using primers (Bioneer, Daejeon) and a Taqman probe (Roche, Germany) in LC480 (Roche, Germany), so as to determine the number of transcripts. Quantitative analysis of the transcripts was performed through comparison with 18S RNA transcripts. The primer pairs for the semiquantitative PCR are noted in [table8].

TABLE 8

| Primer pairs for PCR | | |
|---|---|---|
| Name of Primer | SEQ ID NO: | Sequence(5'-3') |
| TNF-a-forward | 51 | ctgtagcccacgtcgtagc |
| TNF-a-reverse | 52 | ttgagatccatgccgttg |
| RANKL-forward | 53 | tgaagacacactacctgactcctg |
| RANKL-reverse | 54 | ccacaatgtgttgcagttcc |
| IL-1β-forward | 55 | tgtaatgaaagacggcacacc |
| IL-1β-reverse | 56 | tcttctttgggtattgcttgg |
| CCL-2-forward | 57 | catccacgtgttggctca |
| CCL-2-reverse | 58 | gatcatcttgctggtgaatgagt |
| MMP-1-forward | 59 | tgtgtttcacaacggagacc |
| MMP-1-reverse | 60 | gcccaagttgtagtagttttcca |
| MMP-3-forward | 61 | tgttctttgatgcagtcagc |
| MMP-3-reverse | 62 | gatttgcgccaaaagtgc |
| IL-6-forward | 63 | gagaaaagagttgtgcaatggc |
| IL-6-reverse | 64 | ccagtttggtagcatccatca |
| VCAM-1-forward | 65 | tggtgaaatggaatctgaacc |
| VCAM-1-reverse | 66 | cccagatggtggtttcctt |
| 18S-forward | 67 | aaatcagttatggttcctttggtc |

TABLE 8-continued

| Primer pairs for PCR | | |
|---|---|---|
| Name of Primer | SEQ ID NO: | Sequence(5'-3') |
| 18S-reverse | 68 | gctctagaattaccacagttatcc aa |

It was found that as shown in FIG. 21, in the MFK24-administered group, the number of transcripts of inflammatory mediators was significantly reduced compared to that in an arthritis control group, and also, according to doses, the expression of ICAM-1 and RANKL in the inflammatory region was reduced. Especially, it was found that when MFK24 was administered in a low dose of 0.1 mg/kg, the high efficacy was maintained (see FIG. 22).

Comparative Example 3

Examination on an Arthritis Therapeutic Effect by mdhFas-1 Peptide

By using mdhFas-1 peptide prepared from <Comparative Example 1>, in a CIA mouse model, an arthritis therapeutic effect was measured in the same manner as described in Example 4.

As a result, when mdhFas-1 peptide was used, as shown in FIG. 23, arthritis was concentration-dependently inhibited, and also abnormal findings in the weight change were not observed compared to in a control group mouse. It was found that the treatment in a dose of 10 mg/kg inhibited arthritis by about 32%, and the treatment in a dose of 30 mg/kg inhibited arthritis by about 69%.

Comparative Example 4

Examination on an Arthritis Therapeutic Effect by MFK12 Peptide

By using MFK12 peptide prepared from <Comparative Example 2>, in a CIA mouse model, an arthritis therapeutic effect was measured in the same manner as described in Examples 4 and 5.

As a result, when MFK12 peptide was used, as shown in FIG. 24, arthritis was concentration-dependently inhibited, and also abnormal findings in the weight change were not observed compared to in a control group mouse. It was found that the treatment in a dose of 10 mg/kg inhibited arthritis by about 27%, and the treatment in a dose of 30 mg/kg inhibited arthritis by about 60%.

Also, as shown in FIG. 25, it was found that on the 50th day after 4 weeks from second immunization, in the group treated in a dose of 10 mg/kg, the articulation region was destroyed, Synovial membrane tissue cells were hyperproliferated, the vascularization induction and the cell adhesion protein expression were increased as much as that in the control group. Meanwhile, in the group treated in a dose of 30 mg/kg, the proliferation of Synovial membrane tissue cells was inhibited compared to that in the control group, vascularization induction and adhesion protein expression were reduced, and the shape of the foot tissue seemed to be nearly normal. Thus, it was found that the treatment of MFK12 in a dose of 30 mg/kg shows a therapeutic effect.

As shown in [FIG. 26] and [FIG. 27], it was found that through the measurement of the change in inflammatory mediators, the group treated in a dose of 10 mg/kg showed similar expression levels of TNF-a, IL-6, IL-1β, ICAM-1, and RANKL to the arthritis control group, while the group treated in a dose of 30 mg/kg showed reduced levels compared to the arthritis control group. Also, it was found that the group treated in a dose of 10 mg/kg showed similar expression levels of ICAM-1 and RANKL to the arthritis control group, while the group treated in a dose of 30 mg/kg showed reduced levels compared to the arthritis control group.

As can be seen foregoing, the fusion peptide of the present invention inhibits expension of rheumatoid arthritis by adhesion and migration of sinoviocytes and may be used for preventing or treating inflammatory disease by inhibiting infiltration of immune cells.

The invention claimed is:

1. A fusion peptide, comprising a) a dhFas-1 domain which is the fourth fascilin (fas-1) domain of TGF-β inducible gene-h3 (βig-h3) lacking H1 and H2 regions;

b) a Matrix metalloproteinase (MMP) substrate; and c) a peptide comprising RGD motif, wherein the dhFas-1 domain consists of SEQ ID NO:1 or 3, the MMP substrate consists of SEQ ID NO:5 to 8, and the peptide comprising RGD motif consists of SEQ ID NO: 9 or 10; and, a), b), and c) are sequentially linked.

2. The peptide of claim 1, further comprising a linker peptide between a) the dhFas-1 domain and b) the MMP substrate, wherein the linker peptide consists of 1 to 5 amino acids.

3. The peptide of claim 1, further comprising a linker peptide between b) the MMP substrate and c) the peptide comprising RGD motif, wherein the linker peptide consists of 1 to 5 amino acids.

4. The peptide of claim 1, wherein the peptide comprises an amino acid sequence selected from the group consisting of SEQ ID NO:11, SEQ ID NO:12, SEQ ID NO:13, SEQ ID NO:14, SEQ ID NO:15, SEQ ID NO:16, and SEQ ID NO:17.

5. The peptide of claim 3, wherein the linker peptide is LE or EF.

6. The peptide of claim 2, wherein the linker peptide is VD or VDG.

7. A pharmaceutical composition comprising the peptide of claim 1 as an active ingredient.

8. A method for treating rheumatoid arthritis comprising administering to a subject in need thereof an effective amount of the peptide of claim 1.

* * * * *

SEQUENCE LISTING

```
<160> NUMBER OF SEQ ID NOS: 72

<210> SEQ ID NO 1
<211> LENGTH: 72
<212> TYPE: PRT
<213> ORGANISM: Artificial Sequence
<220> FEATURE:
<223> OTHER INFORMATION: mdhFas-1

<400> SEQUENCE: 1

Gln Ala Met Pro Pro Glu Glu Leu Asn Lys Leu Leu Ala Asn Ala Lys
1               5                   10                  15

Glu Leu Thr Asn Ile Leu Lys Tyr His Ile Gly Asp Glu Ile Leu Val
            20                  25                  30

Ser Gly Gly Ile Gly Ala Leu Val Arg Leu Lys Ser Leu Gln Gly Asp
        35                  40                  45

Lys Leu Glu Val Ser Ser Lys Asn Asn Val Val Ser Val Asn Lys Glu
    50                  55                  60

Pro Val Ala Glu Thr Asp Ile Met
```

65 70

<210> SEQ ID NO 2
<211> LENGTH: 216
<212> TYPE: DNA
<213> ORGANISM: Artificial Sequence
<220> FEATURE:
<223> OTHER INFORMATION: mdhFas-1

<400> SEQUENCE: 2
caagccatgc ctccagaaga actgaacaaa ctcttggcaa atgccaagga acttaccaac 60
atcctgaagt accacattgg tgatgaaatc ctggttagcg ggggcatcgg ggccctggtg 120
cggctgaagt ctctccaagg ggacaaactg gaagtcagct cgaaaaacaa tgtagtgagt 180
gtcaataagg agcctgttgc cgaaaccgac atcatg 216

<210> SEQ ID NO 3
<211> LENGTH: 72
<212> TYPE: PRT
<213> ORGANISM: Artificial Sequence
<220> FEATURE:
<223> OTHER INFORMATION: hsdhFas-1

<400> SEQUENCE: 3

Arg Ala Leu Pro Pro Arg Glu Arg Ser Arg Leu Leu Gly Asp Ala Lys
1 5 10 15

Glu Leu Ala Asn Ile Leu Lys Tyr His Ile Gly Asp Glu Ile Leu Val
20 25 30

Ser Gly Gly Ile Gly Ala Leu Val Arg Leu Lys Ser Leu Gln Gly Asp
35 40 45

Lys Leu Glu Val Ser Leu Lys Asn Asn Val Val Ser Val Asn Lys Glu
50 55 60

Pro Val Ala Glu Pro Asp Ile Met
65 70

<210> SEQ ID NO 4
<211> LENGTH: 216
<212> TYPE: DNA
<213> ORGANISM: Artificial Sequence
<220> FEATURE:
<223> OTHER INFORMATION: hsdhFas-1

<400> SEQUENCE: 4
cgagccctgc caccaagaga acggagcaga ctcttgggag atgccaagga acttgccaac 60
atcctgaaat accacattgg tgatgaaatc ctggttagcg gaggcatcgg ggccctggtg 120
cggctaaagt ctctccaagg tgacaagctg gaagtcagct tgaaaaacaa tgtggtgagt 180
gtcaacaagg agcctgttgc cgagcctgac atcatg 216

<210> SEQ ID NO 5
<211> LENGTH: 7
<212> TYPE: PRT
<213> ORGANISM: Artificial Sequence
<220> FEATURE:
<223> OTHER INFORMATION: MMP2 Substrate

<400> SEQUENCE: 5

Gly Pro Leu Gly Val Arg Gly
1 5

<210> SEQ ID NO 6
<211> LENGTH: 7

<212> TYPE: PRT
<213> ORGANISM: Artificial Sequence
<220> FEATURE:
<223> OTHER INFORMATION: MMP1 substrate

<400> SEQUENCE: 6

Gly Pro Gln Gly Ile Ala Gly
1 5

<210> SEQ ID NO 7
<211> LENGTH: 7
<212> TYPE: PRT
<213> ORGANISM: Artificial Sequence
<220> FEATURE:
<223> OTHER INFORMATION: MMP consensus substrate

<400> SEQUENCE: 7

Gly Pro Leu Gly Ile Ala Gly
1 5

<210> SEQ ID NO 8
<211> LENGTH: 9
<212> TYPE: PRT
<213> ORGANISM: Artificial Sequence
<220> FEATURE:
<223> OTHER INFORMATION: MMp3 substrate

<400> SEQUENCE: 8

Gly Pro Leu Gly Leu Trp Ala Arg Gly
1 5

<210> SEQ ID NO 9
<211> LENGTH: 5
<212> TYPE: PRT
<213> ORGANISM: Artificial Sequence
<220> FEATURE:
<223> OTHER INFORMATION: amino acid chain comprising 'RGD'

<400> SEQUENCE: 9

Arg Gly Asp Ser Pro
1 5

<210> SEQ ID NO 10
<211> LENGTH: 8
<212> TYPE: PRT
<213> ORGANISM: Artificial Sequence
<220> FEATURE:
<223> OTHER INFORMATION: amino acid chain comprising 'RGD'

<400> SEQUENCE: 10

Gln Glu Arg Gly Asp Ser Leu Ala
1 5

<210> SEQ ID NO 11
<211> LENGTH: 95
<212> TYPE: PRT
<213> ORGANISM: Artificial Sequence
<220> FEATURE:
<223> OTHER INFORMATION: MFK23

<400> SEQUENCE: 11

Gln Ala Met Pro Pro Glu Glu Leu Asn Lys Leu Leu Ala Asn Ala Lys
1 5 10 15

Glu Leu Thr Asn Ile Leu Lys Tyr His Ile Gly Asp Glu Ile Leu Val
20 25 30

Ser Gly Gly Ile Gly Ala Leu Val Arg Leu Lys Ser Leu Gln Gly Asp

-continued

```
        35                  40                  45

Lys Leu Glu Val Ser Ser Lys Asn Asn Val Val Ser Val Asn Lys Glu
    50                  55                  60

Pro Val Ala Glu Thr Asp Ile Met Glu Phe Gly Pro Leu Gly Val Arg
65                  70                  75                  80

Gly Val Asp Gly Gln Glu Arg Gly Asp Ser Leu Ala Gly Leu Glu
                85                  90                  95


<210> SEQ ID NO 12
<211> LENGTH: 95
<212> TYPE: PRT
<213> ORGANISM: Artificial Sequence
<220> FEATURE:
<223> OTHER INFORMATION: MFK24

<400> SEQUENCE: 12

Gln Ala Met Pro Pro Glu Glu Leu Asn Lys Leu Leu Ala Asn Ala Lys
1               5                   10                  15

Glu Leu Thr Asn Ile Leu Lys Tyr His Ile Gly Asp Glu Ile Leu Val
            20                  25                  30

Ser Gly Gly Ile Gly Ala Leu Val Arg Leu Lys Ser Leu Gln Gly Asp
        35                  40                  45

Lys Leu Glu Val Ser Ser Lys Asn Asn Val Val Ser Val Asn Lys Glu
    50                  55                  60

Pro Val Ala Glu Thr Asp Ile Met Glu Phe Gly Pro Gln Gly Ile Ala
65                  70                  75                  80

Gly Val Asp Gly Gln Glu Arg Gly Asp Ser Leu Ala Gly Leu Glu
                85                  90                  95


<210> SEQ ID NO 13
<211> LENGTH: 95
<212> TYPE: PRT
<213> ORGANISM: Artificial Sequence
<220> FEATURE:
<223> OTHER INFORMATION: MFK25

<400> SEQUENCE: 13

Gln Ala Met Pro Pro Glu Glu Leu Asn Lys Leu Leu Ala Asn Ala Lys
1               5                   10                  15

Glu Leu Thr Asn Ile Leu Lys Tyr His Ile Gly Asp Glu Ile Leu Val
            20                  25                  30

Ser Gly Gly Ile Gly Ala Leu Val Arg Leu Lys Ser Leu Gln Gly Asp
        35                  40                  45

Lys Leu Glu Val Ser Ser Lys Asn Asn Val Val Ser Val Asn Lys Glu
    50                  55                  60

Pro Val Ala Glu Thr Asp Ile Met Glu Phe Gly Pro Leu Gly Ile Ala
65                  70                  75                  80

Gly Val Asp Gly Gln Glu Arg Gly Asp Ser Leu Ala Gly Leu Glu
                85                  90                  95


<210> SEQ ID NO 14
<211> LENGTH: 121
<212> TYPE: PRT
<213> ORGANISM: Artificial Sequence
<220> FEATURE:
<223> OTHER INFORMATION: MFK27

<400> SEQUENCE: 14

Met Ala Leu Leu Met Arg Leu Leu Thr Leu Ala Leu Ala Leu Ser Val
1               5                   10                  15
```

```
Gly Pro Ala Gly Thr Leu Ala Arg Ser Gln Ala Met Pro Pro Glu Glu
            20                  25                  30

Leu Asn Lys Leu Leu Ala Asn Ala Lys Glu Leu Thr Asn Ile Leu Lys
        35                  40                  45

Tyr His Ile Gly Asp Glu Ile Leu Val Ser Gly Gly Ile Gly Ala Leu
    50                  55                  60

Val Arg Leu Lys Ser Leu Gln Gly Asp Lys Leu Glu Val Ser Ser Lys
65                  70                  75                  80

Asn Asn Val Val Ser Val Asn Lys Glu Pro Val Ala Glu Thr Asp Ile
                85                  90                  95

Met Glu Phe Gly Pro Leu Gly Leu Trp Ala Arg Gly Val Asp Gln Glu
            100                 105                 110

Arg Gly Asp Ser Leu Ala Gly Leu Glu
        115                 120


<210> SEQ ID NO 15
<211> LENGTH: 95
<212> TYPE: PRT
<213> ORGANISM: Artificial Sequence
<220> FEATURE:
<223> OTHER INFORMATION: hsFJ24

<400> SEQUENCE: 15

Arg Ala Leu Pro Pro Arg Glu Arg Ser Arg Leu Leu Gly Asp Ala Lys
1               5                   10                  15

Glu Leu Ala Asn Ile Leu Lys Tyr His Ile Gly Asp Glu Ile Leu Val
            20                  25                  30

Ser Gly Gly Ile Gly Ala Leu Val Arg Leu Lys Ser Leu Gln Gly Asp
        35                  40                  45

Lys Leu Glu Val Ser Leu Lys Asn Asn Val Val Ser Val Asn Lys Glu
    50                  55                  60

Pro Val Ala Glu Pro Asp Ile Met Glu Phe Gly Pro Gln Gly Ile Ala
65                  70                  75                  80

Gly Val Asp Gly Gln Glu Arg Gly Asp Ser Leu Ala Gly Leu Glu
                85                  90                  95


<210> SEQ ID NO 16
<211> LENGTH: 95
<212> TYPE: PRT
<213> ORGANISM: Artificial Sequence
<220> FEATURE:
<223> OTHER INFORMATION: hsFj25

<400> SEQUENCE: 16

Arg Ala Leu Pro Pro Arg Glu Arg Ser Arg Leu Leu Gly Asp Ala Lys
1               5                   10                  15

Glu Leu Ala Asn Ile Leu Lys Tyr His Ile Gly Asp Glu Ile Leu Val
            20                  25                  30

Ser Gly Gly Ile Gly Ala Leu Val Arg Leu Lys Ser Leu Gln Gly Asp
        35                  40                  45

Lys Leu Glu Val Ser Leu Lys Asn Asn Val Val Ser Val Asn Lys Glu
    50                  55                  60

Pro Val Ala Glu Pro Asp Ile Met Glu Phe Gly Pro Leu Gly Ile Ala
65                  70                  75                  80

Gly Val Asp Gly Gln Glu Arg Gly Asp Ser Leu Ala Gly Leu Glu
                85                  90                  95
```

-continued

<210> SEQ ID NO 17
<211> LENGTH: 122
<212> TYPE: PRT
<213> ORGANISM: Artificial Sequence
<220> FEATURE:
<223> OTHER INFORMATION: hsFJ27

<400> SEQUENCE: 17

```
Met Ala Leu Phe Val Arg Leu Leu Ala Leu Ala Leu Ala Leu Ala Leu
1               5                   10                  15

Gly Pro Ala Ala Thr Leu Ala Arg Ser Phe Arg Ala Leu Pro Pro Arg
            20                  25                  30

Glu Arg Ser Arg Leu Leu Gly Asp Ala Lys Glu Leu Ala Asn Ile Leu
        35                  40                  45

Lys Tyr His Ile Gly Asp Glu Ile Leu Val Ser Gly Gly Ile Gly Ala
    50                  55                  60

Leu Val Arg Leu Lys Ser Leu Gln Gly Asp Lys Leu Glu Val Ser Leu
65                  70                  75                  80

Lys Asn Asn Val Val Ser Val Asn Lys Glu Pro Val Ala Glu Pro Asp
                85                  90                  95

Ile Met Glu Phe Gly Pro Leu Gly Leu Trp Ala Arg Gly Val Asp Gln
            100                 105                 110

Glu Arg Gly Asp Ser Leu Ala Gly Leu Glu
        115                 120
```

<210> SEQ ID NO 18
<211> LENGTH: 285
<212> TYPE: DNA
<213> ORGANISM: Artificial Sequence
<220> FEATURE:
<223> OTHER INFORMATION: MFK23

<400> SEQUENCE: 18

```
caagccatgc ctccagaaga actgaacaaa ctcttggcaa atgccaagga acttaccaac      60

atcctgaagt accacattgg tgatgaaatc ctggttagcg ggggcatcgg ggccctggtg     120

cggctgaagt ctctccaagg ggacaaactg gaagtcagct cgaaaaacaa tgtagtgagt     180

gtcaataagg agcctgttgc cgaaaccgac atcatggaat tcggaccact gggagtccga     240

ggagtcgacg gacaagaacg aggagattct ctggcaggac tcgag                     285
```

<210> SEQ ID NO 19
<211> LENGTH: 285
<212> TYPE: DNA
<213> ORGANISM: Artificial Sequence
<220> FEATURE:
<223> OTHER INFORMATION: MFK24

<400> SEQUENCE: 19

```
caagccatgc ctccagaaga actgaacaaa ctcttggcaa atgccaagga acttaccaac      60

atcctgaagt accacattgg tgatgaaatc ctggttagcg ggggcatcgg ggccctggtg     120

cggctgaagt ctctccaagg ggacaaactg gaagtcagct cgaaaaacaa tgtagtgagt     180

gtcaataagg agcctgttgc cgaaaccgac atcatggaat tcggaccaca aggaatagca     240

ggagtcgacg gacaagaacg aggagattct ctggcaggac tcgag                     285
```

<210> SEQ ID NO 20
<211> LENGTH: 285
<212> TYPE: DNA
<213> ORGANISM: Artificial Sequence
<220> FEATURE:

<223> OTHER INFORMATION: MFK25

<400> SEQUENCE: 20
caagccatgc ctccagaaga actgaacaaa ctcttggcaa atgccaagga acttaccaac 60
atcctgaagt accacattgg tgatgaaatc ctggttagcg ggggcatcgg ggccctggtg 120
cggctgaagt ctctccaagg ggacaaactg gaagtcagct cgaaaaacaa tgtagtgagt 180
gtcaataagg agcctgttgc cgaaaccgac atcatggaat tcggaccact gggaatagca 240
ggagtcgacg gacaagaacg aggagattct ctggcaggac tcgag 285

<210> SEQ ID NO 21
<211> LENGTH: 363
<212> TYPE: DNA
<213> ORGANISM: Artificial Sequence
<220> FEATURE:
<223> OTHER INFORMATION: MFK27

<400> SEQUENCE: 21
atggcgctcc tcatgcgact gctgaccctc gctctggcac tgtctgtggg ccccgctggg 60
acccttgcaa gatctcaagc catgcctcca gaagaactga acaaactctt ggcaaatgcc 120
aaggaactta ccaacatcct gaagtaccac attggtgatg aaatcctggt tagcggaggc 180
atcggggccc tggtgcggct gaagtctctc caaggggaca aactggaagt cagctcgaaa 240
aacaatgtag tgagtgtcaa taaggagcct gttgccgaaa ccgacatcat ggaattcgga 300
ccactgggac tgtgggcaag aggagtcgac caagaacgag gagattctct ggcaggactc 360
gag 363

<210> SEQ ID NO 22
<211> LENGTH: 285
<212> TYPE: DNA
<213> ORGANISM: Artificial Sequence
<220> FEATURE:
<223> OTHER INFORMATION: hsFJ24

<400> SEQUENCE: 22
cgagccctgc caccaagaga acggagcaga ctcttgggag atgccaagga acttgccaac 60
atcctgaaat accacattgg tgatgaaatc ctggttagcg gaggcatcgg ggccctggtg 120
cggctaaagt ctctccaagg tgacaagctg gaagtcagct tgaaaaacaa tgtggtgagt 180
gtcaacaagg agcctgttgc cgagcctgac atcatggaat tcggaccaca aggaatagca 240
ggagtcgacg gacaagaacg aggagattct ctggcaggac tcgag 285

<210> SEQ ID NO 23
<211> LENGTH: 285
<212> TYPE: DNA
<213> ORGANISM: Artificial Sequence
<220> FEATURE:
<223> OTHER INFORMATION: hsFJ25

<400> SEQUENCE: 23
cgagccctgc caccaagaga acggagcaga ctcttgggag atgccaagga acttgccaac 60
atcctgaaat accacattgg tgatgaaatc ctggttagcg gaggcatcgg ggccctggtg 120
cggctaaagt ctctccaagg tgacaagctg gaagtcagct tgaaaaacaa tgtggtgagt 180
gtcaacaagg agcctgttgc cgagcctgac atcatggaat tcggaccact gggaatagca 240
ggagtcgacg gacaagaacg aggagattct ctggcaggac tcgag 285

<210> SEQ ID NO 24
<211> LENGTH: 366
<212> TYPE: DNA
<213> ORGANISM: Artificial Sequence
<220> FEATURE:
<223> OTHER INFORMATION: hsFJ27

<400> SEQUENCE: 24
atggcgctct tcgtgcggct gctggctctc gccctggctc tggccctggg ccccgccgcg 60
accctggcga gatctttccg agccctgcca ccaagagaac ggagcagact cttgggagat 120
gccaaggaac ttgccaacat cctgaaatac cacattggtg atgaaatcct ggttagcgga 180
ggcatcgggg ccctggtgcg gctaaagtct ctccaaggtg acaagctgga agtcagcttg 240
aaaaacaatg tggtgagtgt caacaaggag cctgttgccg agcctgacat catggaattc 300
ggaccactgg gactgtgggc aagaggagtc gaccaagaac gaggagattc tctggcagga 360
ctcgag 366

<210> SEQ ID NO 25
<211> LENGTH: 88
<212> TYPE: PRT
<213> ORGANISM: Artificial Sequence
<220> FEATURE:
<223> OTHER INFORMATION: MFK12

<400> SEQUENCE: 25

Gln Ala Met Pro Pro Glu Glu Leu Asn Lys Leu Leu Ala Asn Ala Lys
1 5 10 15

Glu Leu Thr Asn Ile Leu Lys Tyr His Ile Gly Asp Glu Ile Leu Val
20 25 30

Ser Gly Gly Ile Gly Ala Leu Val Arg Leu Lys Ser Leu Gln Gly Asp
35 40 45

Lys Leu Glu Val Ser Ser Lys Asn Asn Val Val Ser Val Asn Lys Glu
50 55 60

Pro Val Ala Glu Thr Asp Ile Met Glu Phe Gly Gly Arg Gly Asp Ser
65 70 75 80

Pro Asp Asp Asp Asp Asp Leu Glu
85

<210> SEQ ID NO 26
<211> LENGTH: 264
<212> TYPE: DNA
<213> ORGANISM: Artificial Sequence
<220> FEATURE:
<223> OTHER INFORMATION: MFK12

<400> SEQUENCE: 26
caagccatgc ctccagaaga actgaacaaa ctcttggcaa atgccaagga acttaccaac 60
atcctgaagt accacattgg tgatgaaatc ctggttagcg ggggcatcgg ggccctggtg 120
cggctgaagt ctctccaagg ggacaaactg gaagtcagct cgaaaaacaa tgtagtgagt 180
gtcaataagg agcctgttgc cgaaaccgac atcatggaat tcggaggacg aggagattca 240
cccgatgatg atgatgatct cgag 264

<210> SEQ ID NO 27
<211> LENGTH: 20
<212> TYPE: DNA
<213> ORGANISM: Artificial Sequence
<220> FEATURE:
<223> OTHER INFORMATION: primer for mdhFas-1-forward

<400> SEQUENCE: 27
tatcatatgc aagccatgcc 20

<210> SEQ ID NO 28
<211> LENGTH: 20
<212> TYPE: DNA
<213> ORGANISM: Artificial Sequence
<220> FEATURE:
<223> OTHER INFORMATION: primer for mdhFas-1-reverse

<400> SEQUENCE: 28
tcaccgaatt ccatgatgtc 20

<210> SEQ ID NO 29
<211> LENGTH: 42
<212> TYPE: DNA
<213> ORGANISM: Artificial Sequence
<220> FEATURE:
<223> OTHER INFORMATION: primer for RGDSP-forward

<400> SEQUENCE: 29
aattcggagg acgaggagat tcacccgatg atgatgatga tc 42

<210> SEQ ID NO 30
<211> LENGTH: 42
<212> TYPE: DNA
<213> ORGANISM: Artificial Sequence
<220> FEATURE:
<223> OTHER INFORMATION: primer for RGDSP-reverse

<400> SEQUENCE: 30
tcgagatcat catcatcatc gggtgaatct cctcgtcctc cg 42

<210> SEQ ID NO 31
<211> LENGTH: 27
<212> TYPE: DNA
<213> ORGANISM: Artificial Sequence
<220> FEATURE:
<223> OTHER INFORMATION: primer for MMP1 substrate-forward

<400> SEQUENCE: 31
aattcggacc acaaggaata gcaggag 27

<210> SEQ ID NO 32
<211> LENGTH: 27
<212> TYPE: DNA
<213> ORGANISM: Artificial Sequence
<220> FEATURE:
<223> OTHER INFORMATION: primer for MMP1 substrate-reverse

<400> SEQUENCE: 32
tcgactcctg ctattccttg tggtccg 27

<210> SEQ ID NO 33
<211> LENGTH: 27
<212> TYPE: DNA
<213> ORGANISM: Artificial Sequence
<220> FEATURE:
<223> OTHER INFORMATION: primer for MMP2 substrate-forward

<400> SEQUENCE: 33
aattcggacc actgggagtc cgaggag 27

<210> SEQ ID NO 34
<211> LENGTH: 27

-continued

<212> TYPE: DNA
<213> ORGANISM: Artificial Sequence
<220> FEATURE:
<223> OTHER INFORMATION: primer for MMP2 substrate-reverse

<400> SEQUENCE: 34
tcgactcctc ggactcccag tggtccg 27

<210> SEQ ID NO 35
<211> LENGTH: 27
<212> TYPE: DNA
<213> ORGANISM: Artificial Sequence
<220> FEATURE:
<223> OTHER INFORMATION: primer for MMP consensus substrate-forward

<400> SEQUENCE: 35
aattcggacc actgggaata gcaggag 27

<210> SEQ ID NO 36
<211> LENGTH: 27
<212> TYPE: DNA
<213> ORGANISM: Artificial Sequence
<220> FEATURE:
<223> OTHER INFORMATION: primer for MMP consensus substrate-reverse

<400> SEQUENCE: 36
tcgactcctg ctattcccag tggtccg 27

<210> SEQ ID NO 37
<211> LENGTH: 30
<212> TYPE: DNA
<213> ORGANISM: Artificial Sequence
<220> FEATURE:
<223> OTHER INFORMATION: primer for QERGDSLA-forward

<400> SEQUENCE: 37
tcgaccaaga acgaggagat tctctggcac 30

<210> SEQ ID NO 38
<211> LENGTH: 30
<212> TYPE: DNA
<213> ORGANISM: Artificial Sequence
<220> FEATURE:
<223> OTHER INFORMATION: primer for QERGDSLA-reverse

<400> SEQUENCE: 38
tcgagtgcca gagaatctcc tcgttcttgg 30

<210> SEQ ID NO 39
<211> LENGTH: 21
<212> TYPE: DNA
<213> ORGANISM: Artificial Sequence
<220> FEATURE:
<223> OTHER INFORMATION: primer for mouse signal peptide-forward

<400> SEQUENCE: 39
agtacatatg atggcgctcc t 21

<210> SEQ ID NO 40
<211> LENGTH: 22
<212> TYPE: DNA
<213> ORGANISM: Artificial Sequence
<220> FEATURE:
<223> OTHER INFORMATION: primer for mouse signal peptide-reverse

<400> SEQUENCE: 40

-continued agtagatctc tgcaagggtc cc 22

<210> SEQ ID NO 41
<211> LENGTH: 20
<212> TYPE: DNA
<213> ORGANISM: Artificial Sequence
<220> FEATURE:
<223> OTHER INFORMATION: primer for mdhFas-1-forward

<400> SEQUENCE: 41
acagatctca agccatgcct 20

<210> SEQ ID NO 42
<211> LENGTH: 20
<212> TYPE: DNA
<213> ORGANISM: Artificial Sequence
<220> FEATURE:
<223> OTHER INFORMATION: primer for mdhFas-1-reverse

<400> SEQUENCE: 42
acgaattcca tgatgtcggt 20

<210> SEQ ID NO 43
<211> LENGTH: 33
<212> TYPE: DNA
<213> ORGANISM: Artificial Sequence
<220> FEATURE:
<223> OTHER INFORMATION: primer for MMP3 substrate-forward

<400> SEQUENCE: 43
aattcggacc actgggactg tgggcaagag gag 33

<210> SEQ ID NO 44
<211> LENGTH: 33
<212> TYPE: DNA
<213> ORGANISM: Artificial Sequence
<220> FEATURE:
<223> OTHER INFORMATION: primer for MMP3 substrate-reverse

<400> SEQUENCE: 44
tcgactcctc ttgcccacag tcccagtggt ccg 33

<210> SEQ ID NO 45
<211> LENGTH: 20
<212> TYPE: DNA
<213> ORGANISM: Artificial Sequence
<220> FEATURE:
<223> OTHER INFORMATION: primer for hsdhFas-1-forward

<400> SEQUENCE: 45
tatatcatat gcgagccctg 20

<210> SEQ ID NO 46
<211> LENGTH: 20
<212> TYPE: DNA
<213> ORGANISM: Artificial Sequence
<220> FEATURE:
<223> OTHER INFORMATION: primer for hsdhFas-1-reverse

<400> SEQUENCE: 46
tatatcatat gcgagccctg 20

<210> SEQ ID NO 47
<211> LENGTH: 21
<212> TYPE: DNA
<213> ORGANISM: Artificial Sequence
<220> FEATURE:
<223> OTHER INFORMATION: primer for human signal peptide-forward

<400> SEQUENCE: 47
atgcatatga tggcgctctt c 21

<210> SEQ ID NO 48
<211> LENGTH: 22
<212> TYPE: DNA
<213> ORGANISM: Artificial Sequence
<220> FEATURE:
<223> OTHER INFORMATION: primer for human signal peptide-reverse

<400> SEQUENCE: 48
agtagatctc tgcaagggtc cc 22

<210> SEQ ID NO 49
<211> LENGTH: 19
<212> TYPE: DNA
<213> ORGANISM: Artificial Sequence
<220> FEATURE:
<223> OTHER INFORMATION: primer for hsdhFas-1-forward

<400> SEQUENCE: 49
aagatctttc cgagccctg 19

<210> SEQ ID NO 50
<211> LENGTH: 21
<212> TYPE: DNA
<213> ORGANISM: Artificial Sequence
<220> FEATURE:
<223> OTHER INFORMATION: primer for hsdhFas-1-reverse

<400> SEQUENCE: 50
accgaattcc atgatgtcag g 21

<210> SEQ ID NO 51
<211> LENGTH: 19
<212> TYPE: DNA
<213> ORGANISM: Artificial Sequence
<220> FEATURE:
<223> OTHER INFORMATION: primer for TNF-alpha-forward

<400> SEQUENCE: 51
ctgtagccca cgtcgtagc 19

<210> SEQ ID NO 52
<211> LENGTH: 18
<212> TYPE: DNA
<213> ORGANISM: Artificial Sequence
<220> FEATURE:
<223> OTHER INFORMATION: primer for TNF-alpha-reverse

<400> SEQUENCE: 52
ttgagatcca tgccgttg 18

<210> SEQ ID NO 53
<211> LENGTH: 24
<212> TYPE: DNA
<213> ORGANISM: Artificial Sequence
<220> FEATURE:
<223> OTHER INFORMATION: primer for RANKL-forward

<400> SEQUENCE: 53
tgaagacaca ctacctgact cctg 24

<210> SEQ ID NO 54
<211> LENGTH: 20
<212> TYPE: DNA
<213> ORGANISM: Artificial Sequence
<220> FEATURE:
<223> OTHER INFORMATION: primer for RANKL-reverse

<400> SEQUENCE: 54
ccacaatgtg ttgcagttcc 20

<210> SEQ ID NO 55
<211> LENGTH: 21
<212> TYPE: DNA
<213> ORGANISM: Artificial Sequence
<220> FEATURE:
<223> OTHER INFORMATION: primer for IL-1beta-forward

<400> SEQUENCE: 55
tgtaatgaaa gacggcacac c 21

<210> SEQ ID NO 56
<211> LENGTH: 21
<212> TYPE: DNA
<213> ORGANISM: Artificial Sequence
<220> FEATURE:
<223> OTHER INFORMATION: primer for IL-1beta-reverse

<400> SEQUENCE: 56
tcttctttgg gtattgcttg g 21

<210> SEQ ID NO 57
<211> LENGTH: 18
<212> TYPE: DNA
<213> ORGANISM: Artificial Sequence
<220> FEATURE:
<223> OTHER INFORMATION: primer for CCL-2-forward

<400> SEQUENCE: 57
catccacgtg ttggctca 18

<210> SEQ ID NO 58
<211> LENGTH: 23
<212> TYPE: DNA
<213> ORGANISM: Artificial Sequence
<220> FEATURE:
<223> OTHER INFORMATION: primer for CCL-2-reverse

<400> SEQUENCE: 58
gatcatcttg ctggtgaatg agt 23

<210> SEQ ID NO 59
<211> LENGTH: 20
<212> TYPE: DNA
<213> ORGANISM: Artificial Sequence
<220> FEATURE:
<223> OTHER INFORMATION: primer for MMP-1-forward

<400> SEQUENCE: 59
tgtgtttcac aacggagacc 20

<210> SEQ ID NO 60
<211> LENGTH: 23
<212> TYPE: DNA
<213> ORGANISM: Artificial Sequence
<220> FEATURE:
<223> OTHER INFORMATION: primer for MMP-1-reverse

<400> SEQUENCE: 60
gcccaagttg tagtagtttt cca 23

<210> SEQ ID NO 61
<211> LENGTH: 20
<212> TYPE: DNA
<213> ORGANISM: Artificial Sequence
<220> FEATURE:
<223> OTHER INFORMATION: primer for MMP-3-forward

<400> SEQUENCE: 61
tgttctttga tgcagtcagc 20

<210> SEQ ID NO 62
<211> LENGTH: 18
<212> TYPE: DNA
<213> ORGANISM: Artificial Sequence
<220> FEATURE:
<223> OTHER INFORMATION: primer for MMP-3-reverse

<400> SEQUENCE: 62
gatttgcgcc aaaagtgc 18

<210> SEQ ID NO 63
<211> LENGTH: 22
<212> TYPE: DNA
<213> ORGANISM: Artificial Sequence
<220> FEATURE:
<223> OTHER INFORMATION: primer for IL-6-forward

<400> SEQUENCE: 63
gagaaaagag ttgtgcaatg gc 22

<210> SEQ ID NO 64
<211> LENGTH: 21
<212> TYPE: DNA
<213> ORGANISM: Artificial Sequence
<220> FEATURE:
<223> OTHER INFORMATION: primer for IL-6-reverse

<400> SEQUENCE: 64
ccagtttggt agcatccatc a 21

<210> SEQ ID NO 65
<211> LENGTH: 21
<212> TYPE: DNA
<213> ORGANISM: Artificial Sequence
<220> FEATURE:
<223> OTHER INFORMATION: primer for VCAM-1-forward

<400> SEQUENCE: 65
tggtgaaatg gaatctgaac c 21

<210> SEQ ID NO 66
<211> LENGTH: 19
<212> TYPE: DNA
<213> ORGANISM: Artificial Sequence
<220> FEATURE:
<223> OTHER INFORMATION: primer for VCAM-1-reverse

<400> SEQUENCE: 66
cccagatggt ggtttcctt 19

<210> SEQ ID NO 67

-continued

<211> LENGTH: 24
<212> TYPE: DNA
<213> ORGANISM: Artificial Sequence
<220> FEATURE:
<223> OTHER INFORMATION: primer for 18S-forward

<400> SEQUENCE: 67
aaatcagtta tggttccttt ggtc 24

<210> SEQ ID NO 68
<211> LENGTH: 26
<212> TYPE: DNA
<213> ORGANISM: Artificial Sequence
<220> FEATURE:
<223> OTHER INFORMATION: primer for 18S-reverse

<400> SEQUENCE: 68
gctctagaat taccacagtt atccaa 26

<210> SEQ ID NO 69
<211> LENGTH: 4
<212> TYPE: PRT
<213> ORGANISM: Artificial Sequence
<220> FEATURE:
<223> OTHER INFORMATION: LGVR

<400> SEQUENCE: 69

Leu Gly Val Arg
1

<210> SEQ ID NO 70
<211> LENGTH: 4
<212> TYPE: PRT
<213> ORGANISM: Artificial Sequence
<220> FEATURE:
<223> OTHER INFORMATION: QGIA

<400> SEQUENCE: 70

Gln Gly Ile Ala
1

<210> SEQ ID NO 71
<211> LENGTH: 4
<212> TYPE: PRT
<213> ORGANISM: Artificial Sequence
<220> FEATURE:
<223> OTHER INFORMATION: LGLW

<400> SEQUENCE: 71

Leu Gly Leu Trp
1

<210> SEQ ID NO 72
<211> LENGTH: 4
<212> TYPE: PRT
<213> ORGANISM: Artificial Sequence
<220> FEATURE:
<223> OTHER INFORMATION: LGIA

<400> SEQUENCE: 72

Leu Gly Ile Ala
1